(12) United States Patent
Mc Gowan et al.

(10) Patent No.: US 8,357,687 B2
(45) Date of Patent: Jan. 22, 2013

(54) MACROCYCLIC INDOLE DERIVATIVES USEFUL AS HEPATITIS C VIRUS INHIBITORS

(75) Inventors: David Craig Mc Gowan, Mechelen (BE); Sandrine Marie Helene Vendeville, Mechelen (BE); Pierre Jean-Marie Bernard Raboisson, Mechelen (BE); Abdellah Tahri, Anderlecht (BE)

(73) Assignee: Tibotec Pharmaceuticals, Little Island, Co. Cork (IE)

( * ) Notice: Subject to any disclaimer, the term of this patent is extended or adjusted under 35 U.S.C. 154(b) by 0 days.

(21) Appl. No.: 13/058,990

(22) PCT Filed: Aug. 14, 2009

(86) PCT No.: PCT/EP2009/060580
§ 371 (c)(1),
(2), (4) Date: Feb. 14, 2011

(87) PCT Pub. No.: WO2010/018233
PCT Pub. Date: Feb. 18, 2010

(65) Prior Publication Data
US 2011/0152279 A1     Jun. 23, 2011

(30) Foreign Application Priority Data
Aug. 14, 2008  (EP) .................................. 08162435

(51) Int. Cl.
*C07D 515/08*   (2006.01)
*A61K 31/407*   (2006.01)

(52) U.S. Cl. ........................ 514/250; 514/410; 540/458
(58) Field of Classification Search .................. 540/458; 514/250, 410
See application file for complete search history.

(56) References Cited

U.S. PATENT DOCUMENTS

| | | |
|---|---|---|
| 5,807,876 A | 9/1998 | Armistead et al. |
| 6,054,472 A | 4/2000 | Armistead et al. |
| 6,344,465 B1 | 2/2002 | Armistead et al. |
| 6,498,178 B2 | 12/2002 | Stamos et al. |
| 2008/0146537 A1 | 6/2008 | Bender et al. |

FOREIGN PATENT DOCUMENTS

| | | |
|---|---|---|
| WO | 9740028 A1 | 10/1997 |
| WO | 9840381 A1 | 9/1998 |
| WO | 0056331 A1 | 9/2000 |
| WO | 0219369 A2 | 3/2002 |
| WO | 03010140 A2 | 2/2003 |
| WO | 2006029912 A1 | 3/2006 |
| WO | 2007092000 A1 | 8/2007 |
| WO | 2008075103 A1 | 6/2008 |

OTHER PUBLICATIONS

Dierynck, et al., Dec. 15, 2007, Binding Kinetics of Darunavir to Human Immunodeficiency Virus Type 1 Protease Explain the Potent Antiviral Activity and High Genetic Barrier, Journal of Virology, vol. 81, No. 24, pp. 13845-13851.
Harper, et al., 2005, Development and Preliminary Optimization of Indole-N-Acetamide Inhibitors of Hepatitis C Virus NS5B Polymerase, Journal of Medicinal Chemistry, vol. 48, No. 5, pp. 1314-1317.
Kim et al, 2002, The Burden of Hepatitis C in the United States, Hepatology, vol. 36, No. 5, s1, S30-S34.
Koutsoudakis, et al., Jan. 15, 2007, The Level of CD81 Cell Surface Expression is a Key Determinant for Productive Entry of Hepatitis C Virus into Host Cells, Journal of Virology, vol. 81, No. 2, pp. 588-598.
Krieger, et al, May 1, 2001, Enhancement of Hepatitis C Virus RNA Replication by Cell Culture, Journal of Virology, 75-10, 4614-1624, DE.
Lohmann, et al., 1999, Replication of Subgenomic Hepatitis C Virus RNAs in a Hepatoma Cell Line, Science, vol. 285, pp. 110-113.
Unknown, Jun. 2002, National Insttutes of Health Consensus Development Conference Statement: Management of Hepatitis C: 2002, Hepatology, vol. 36, No. 5, S3-S20.

*Primary Examiner* — Bruck Kifle
(74) *Attorney, Agent, or Firm* — Andrea Jo Kamage

(57) ABSTRACT

Inhibitors of HCV replication of formula (I) including stereochemically isomeric forms, and salts, hydrates, solvates thereof, wherein Y, $R_1$, $R_2$, $R_4$ and n have the meaning defined in the claims. The present invention also relates to processes for preparing said compounds, pharmaceutical compositions containing them and their use in HCV therapy.

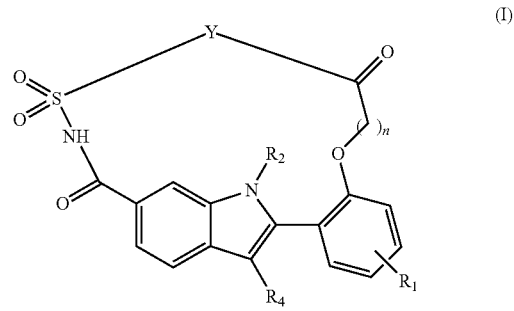

10 Claims, No Drawings

MACROCYCLIC INDOLE DERIVATIVES USEFUL AS HEPATITIS C VIRUS INHIBITORS

FIELD OF THE INVENTION

The present invention is concerned with macrocyclic indole derivatives having inhibitory activity on the replication of the hepatitis C virus (HCV). It further concerns compositions comprising these compounds as active ingredients as well as processes for preparing these compounds and compositions.

BACKGROUND OF THE INVENTION

Hepatitis C virus is the leading cause of chronic liver disease worldwide and has become a focus of considerable medical research. HCV is a member of the Flaviviridae family of viruses in the hepacivirus genus, and is closely related to the flavivirus genus, which includes a number of viruses implicated in human disease, such as dengue virus and yellow fever virus, and to the animal pestivirus family, which includes bovine viral diarrhoea virus (BVDV). HCV is a positive-sense, single-stranded RNA virus, with a genome of around 9,600 bases. The genome comprises both 5' and 3' untranslated regions that adopt RNA secondary structures, and a central open reading frame that encodes a single polyprotein of around 3,010-3,030 amino acids. The polyprotein encodes ten gene products, which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

HCV replicates preferentially in hepatocytes but is not directly cytopathic, leading to persistent infection. In particular, the lack of a vigorous T-lymphocyte response and the high propensity of the virus to mutate appear to promote a high rate of chronic infection. There are 6 major HCV genotypes and more than 50 subtypes, which are differently distributed geographically. HCV type 1 is the predominant genotype in the US and Europe. For instance, HCV type 1 accounts for 70 to 75 percent of all HCV infections in the United States. The extensive genetic heterogeneity of HCV has important diagnostic and clinical implications, perhaps explaining difficulties in vaccine development and the lack of response to therapy. An estimated 170 million persons worldwide are infected with hepatitis C virus. Following the initial acute infection, a majority of infected individuals develops chronic hepatitis, which can progress to liver fibrosis leading to cirrhosis, end-stage liver disease, and HCC (hepatocellular carcinoma) (National Institutes of Health Consensus Development Conference Statement: Management of Hepatitis C. *Hepatology*, 36, 5 Suppl. S3-S20, 2002). Liver cirrhosis due to HCV infection is responsible for about 10,000 deaths per year in the U.S.A. alone, and is the leading cause for liver transplantations. Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades (Kim, W. R. *Hepatology*, 36, 5 Suppl. S30-S34, 2002).

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, combination therapy has significant side effects and is poorly tolerated in many patients. For instance, in registration trials of pegylated interferon and ribavirin, significant side effects resulted in discontinuation of treatment in approximately 10 to 14 percent of patients. Major side effects of combination therapy include influenza-like symptoms, hematologic abnormalities, and neuropsychiatric symptoms. The development of more effective, convenient and tolerated treatments is a major public health objective. Thus, the treatment of this chronic disease is an unmet clinical need, since current therapy is only partially effective and limited by undesirable side effects.

One area of particular focus has been the search for inhibitors of the NS5b RNA-dependent RNA polymerase (RdRp). Close structural homologs of this polymerase do not exist within the uninfected host cell and the finding of inhibitors of said polymerase would provide a more specific mode of action. Inhibitors that are currently under investigation can be classified as either nucleoside inhibitors (NIs) or non-nucleoside inhibitors (NNIs). NIs directly compete with nucleotide substrates for binding to highly conserved active sites. Greater specificity may be achieved by NNIs, which may interact outside of the highly conserved active site at a unique allosteric site common only to structurally related polymerases.

Indole derivatives have been described for HCV inhibitory activity. WO 2007/092000 discloses tetracyclic indole derivatives as HCV NS5B inhibitors for the treatment and/or prevention of HCV virus infection. US 2008/0146537 discloses cyclopropyl fused indolobenzazepine HCV NS5B inhibitors. WO 2008/075103 discloses macrocyclic indole derivatives useful for the treatment or prevention of infection by hepatitis C virus.

To date, preliminary clinical trials have resulted in a high failure rate, thereby highlighting the need to pursue the search for novel NS5b inhibitors. There is a high medical need for safe and effective anti-HCV treatment. Such HCV inhibitors may overcome the disadvantages of current HCV therapy such as side effects, limited efficacy, the emergence of resistance, and compliance failures, as well as improve the sustained viral response. In particular wherein the therapeutic compounds have good bioavailability and a favorable pharmacokinetic and metabolic profile.

SUMMARY OF THE INVENTION

It has been found that certain macrocyclic indole derivatives exhibit antiviral activity in subjects infected with HCV with useful properties regarding one or more of the following parameters: antiviral efficacy, favorable mutant profile, lack of toxicity, favorable pharmacokinetic and metabolic profile, and ease of formulation and administration. These compounds are therefore useful in treating or combating HCV infections.

The present invention concerns inhibitors of HCV replication, which can be represented by formula (I),

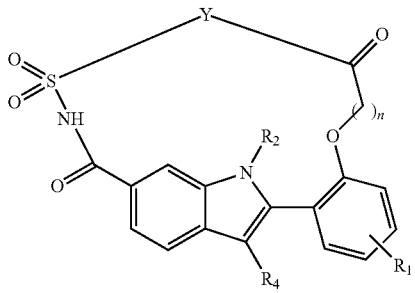

including stereochemically isomeric forms, and salts, hydrates, and solvates thereof, wherein:
$R_1$ is selected from hydrogen, halo and $C_{1-4}$alkoxy;
$R_2$ is selected from $C_{1-4}$alkyl and $C_{3-6}$cycloalkyl;
$R_4$ is $C_{3-7}$cycloalkyl optionally substituted with halo;
n is 1 or 2;
Y is selected from

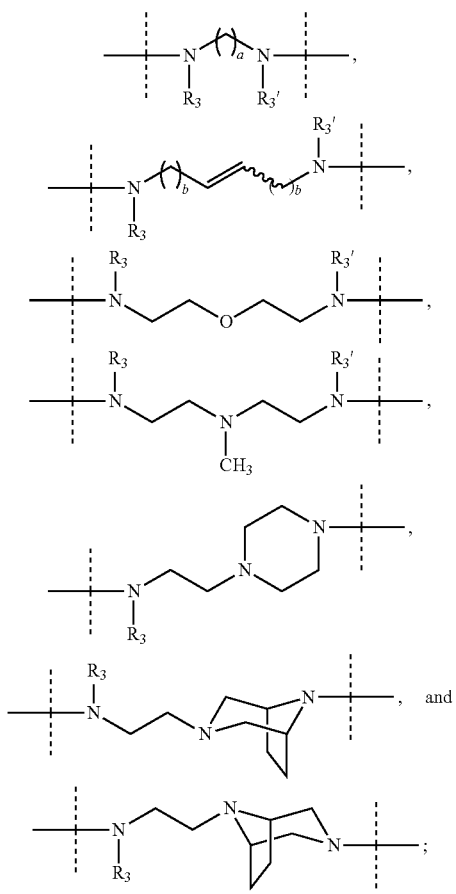

a is 2, 3, 4 or 5;
each b is independently 1 or 2;
$R_3$ and $R_3'$ are independently selected from hydrogen, $C_{1-6}$alkyl and $C_{3-6}$cycloalkyl.
The invention further relates to methods for the preparation of the compounds of formula (I), including stereochemically isomeric forms, and salts, hydrates or solvates thereof, their intermediates, and the use of the intermediates in the preparation of the compounds of formula (I).

The invention relates to the compounds of formula (I) per se, including stereochemically isomeric forms, and salts, hydrates or solvates thereof, for use as a medicament. The invention relates to the compounds of formula (I) per se, including stereochemically isomeric forms, and salts, hydrates or solvates thereof, for treating hepatitis C. The invention further relates to pharmaceutical compositions comprising a carrier and an anti-virally effective amount of a compound of formula (I) as specified herein. The pharmaceutical compositions may comprise combinations of the aforementioned compounds with other anti-HCV agents. The invention also relates to the aforementioned pharmaceutical compositions for administration to a subject suffering from HCV infection. The pharmaceutical compositions may further comprise combinations of the aforementioned compounds or pharmaceutical compositions with anti-HIV agents. The invention thus also relates to the aforementioned pharmaceutical compositions for administration to a subject suffering from HCV/HIV co-infection.

The invention also relates to the use of a compound of formula (I), including stereochemically isomeric forms, or salts, hydrates or solvates thereof, for the manufacture of a medicament for inhibiting HCV replication. The invention also relates to the use of a compound of formula (I), including stereochemically isomeric forms, or salts, hydrates or solvates thereof, for the manufacture of a medicament for preventing or treating conditions associated with HCV. The invention also relates to a method of inhibiting HCV replication in a warm-blooded animal said method comprising the administration of an effective amount of a compound of formula (I), including stereochemically isomeric forms, or salts, hydrates or solvates thereof. The invention also relates to a method for preventing or treating conditions associated with HCV in a warm-blooded animal said method comprising the administration of an effective amount of a compound of formula (I), including stereochemically isomeric forms, or salts, hydrates or solvates thereof. The invention further relates to a method for preventing or treating HCV/HIV co-infection in a warm-blooded animal said method comprising the administration of an effective amount of a compound of formula (I), including stereochemically isomeric forms, or salts, hydrates or solvates thereof.

DETAILED DESCRIPTION

The present invention will now be further described. In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous to formulate a particular embodiment.

As used in the foregoing and hereinafter, the following definitions apply unless otherwise noted.

For the purpose of the present invention, the terms "subject" or "infected subject" or "patient" refers to an individual infected with HCV, in need of treatment.

The term "halo" or "halogen" is generic to fluoro, chloro, bromo and iodo.

As used herein "$C_{1-4}$alkyl" as a group or part of a group defines straight or branched chain saturated hydrocarbon radicals having from 1 to 4 carbon atoms such as for example methyl, ethyl, prop-1-yl, prop-2-yl, but-1-yl, but-2-yl, isobutyl, 2-methyl-prop-1-yl; "$C_{1-3}$alkyl" as a group or part of a group defines straight or branched chain saturated hydrocarbon radicals having from 1 to 3 carbon atoms such as for example methyl, ethyl, prop-1-yl, prop-2-yl. "$C_{1-6}$alkyl" encompasses $C_{1-3}$alkyl and $C_{1-4}$alkyl radicals and the higher homologues thereof having 5 or 6 carbon atoms such as, for example, pent-1-yl, pent-2-yl, pent-3-yl, hex-1-yl, hex-2-yl, 2-methylbut-1-yl, 2-methylpent-1-yl, 2-ethylbut-1-yl, 3-methylpent-2-yl, and the like. Of interest amongst $C_{1-6}$alkyl is $C_{1-4}$alkyl and $C_{1-3}$alkyl.

The term "$C_{1-6}$alkylene" as a group or part of a group refers to $C_{1-6}$alkyl groups that are divalent, i.e., with two single bonds for attachment to two other groups. Non-limiting examples of alkylene groups includes methylene, ethylene, methylmethylene, propylene, ethylethylene, 1-methylethylene and 1,2-dimethylethylene.

"$C_{3-7}$cycloalkyl" is generic to cyclopropyl, cyclobutyl, cyclopentyl, cyclohexyl and cycloheptyl. The term "$C_{3-6}$cycloalkyl" is meant to comprise cyclopropyl, cyclobutyl, cyclopentyl and cyclohexyl. The term "$C_{3-5}$cycloalkyl" is meant to comprise cyclopropyl, cyclobutyl and cyclopentyl.

The term "$C_{1-4}$alkoxy" or "$C_{1-4}$alkyloxy" as a group or part of a group refers to a radical having the Formula —$OR^a$ wherein $R^a$ is $C_{1-4}$alkyl as defined above. Non-limiting examples of suitable $C_{1-4}$alkoxy include methoxy, ethoxy, propoxy, isopropoxy, butoxy, isobutoxy, sec-butoxy and tert-butoxy.

It should be noted that the radical positions on any molecular moiety used in the definitions may be anywhere on such moiety as long as it is chemically stable.

Radicals used in the definitions of the variables include all possible isomers unless otherwise indicated. For instance, piperidinyl includes piperidin-1-yl, piperidin-2-yl, piperidin-3-yl, and piperidin-4-yl; pentyl includes pent-1-yl, pent-2-yl and pent-3-yl.

When any variable occurs more than one time in any constituent, each definition is independent.

Whenever used hereinafter, the term "compounds of formula (I)", or "the present compounds" or similar terms, it is meant to include the compounds of formula (I), including stereochemically isomeric forms, and salts, hydrates or solvates thereof. One embodiment comprises the compounds of formula (I) or any subgroup thereof specified herein, including the possible stereochemically isomeric forms, as well as salts, hydrates and solvates thereof. Another embodiment comprises the compounds of formula (I) or any subgroups thereof specified herein, including the possible stereochemically isomeric forms, as well as the salts, hydrates and solvates thereof.

Whenever used hereinafter, the term "optionally substituted" is meant to include unsubstituted as well as substituted with at least one of the specified substituting radicals. For the purpose of example, "$C_{1-4}$alkyl optionally substituted with chloro" is meant to include unsubstituted $C_{1-4}$alkyl as well as $C_{1-4}$alkyl substituted with chloro.

The compounds of formula (I) may have one or more centers of chirality and may exist as stereochemically isomeric forms. The term "stereochemically isomeric forms" as used herein defines all the possible compounds made up of the same atoms bonded by the same sequence of bonds but having different three-dimensional structures, which the compounds of formula (I) may possess.

With reference to the instances where (R) or (S) is used to designate the absolute configuration of a chiral atom within a substituent, the designation is done taking into consideration the whole compound and not the substituent in isolation.

In one aspect, the present invention provides compounds of formula (I)

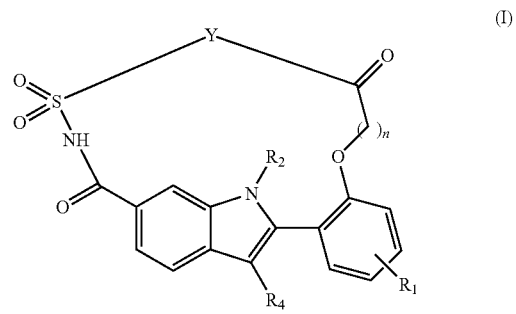

including stereochemically isomeric forms, and N-oxides, salts, hydrates, and solvates thereof, wherein Y, $R_1$, $R_2$, $R_4$ and n have the same meaning as defined herein.

Particular subgroups of compounds of formula (I) are compounds of formula (II), (III), (IV), (V), (VI) and (VII)

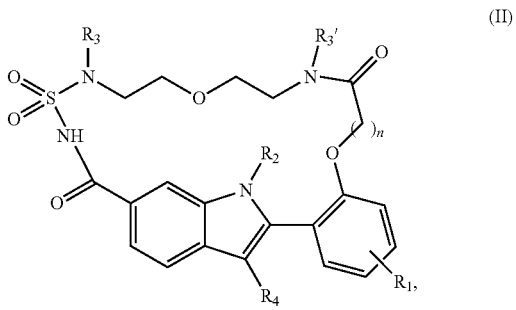

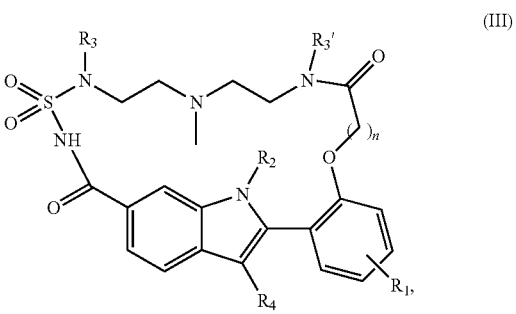

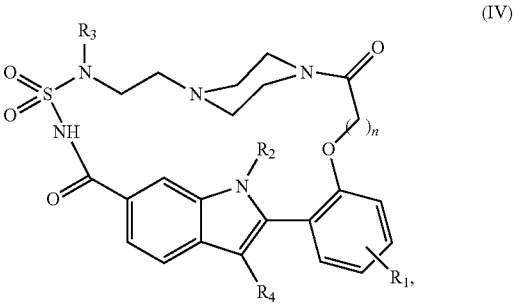

-continued

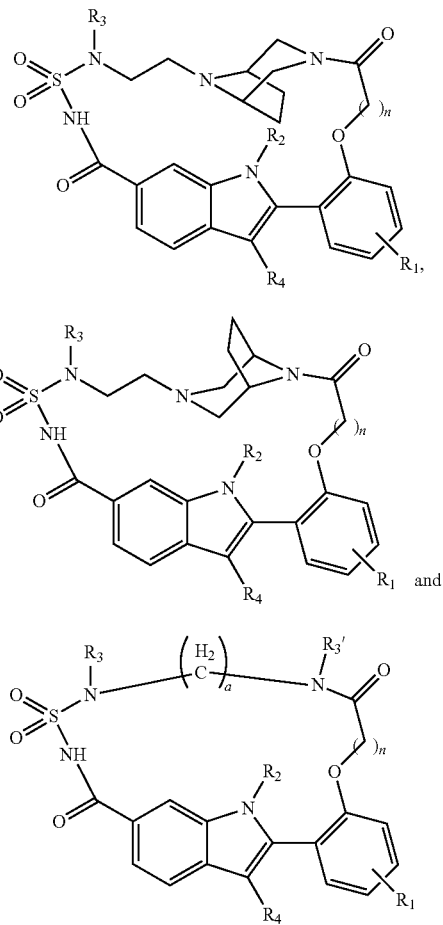

wherein Y, $R_1$, $R_2$, $R_3$, $R_3'$, $R_4$, a and n have the same meaning as defined for compounds of formula (I) or independently any of the embodiments thereof as defined herein.

When Y is according to formula

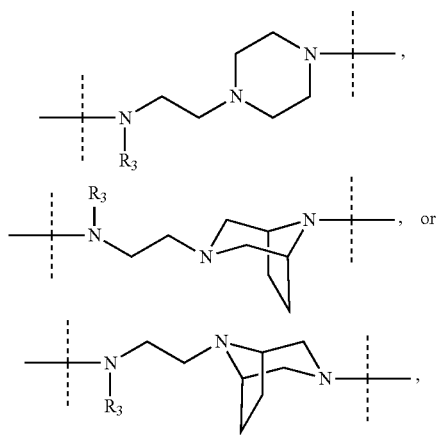

it is understood Y may be oriented in two directions, i.e. the piperazinyl or 3,8-diaza-bicyclo[3.2.1]octane moiety may be connected to the sulfonamide group while the aliphatic amine is connected to the carbonyl group, or, the piperazinyl or 3,8-diaza-bicyclo[3.2.1]octane moiety is connected to the carbonyl group and the aliphatic amine is connected to the sulfonamide group.

Embodiments of the present invention concern compounds of formula (I), or any particular subgroup thereof as defined herein, wherein one or more of the following restrictions apply:

Y is selected from —$N(R_3)$—$(CH_2)_4$—$N(R_3)$—,

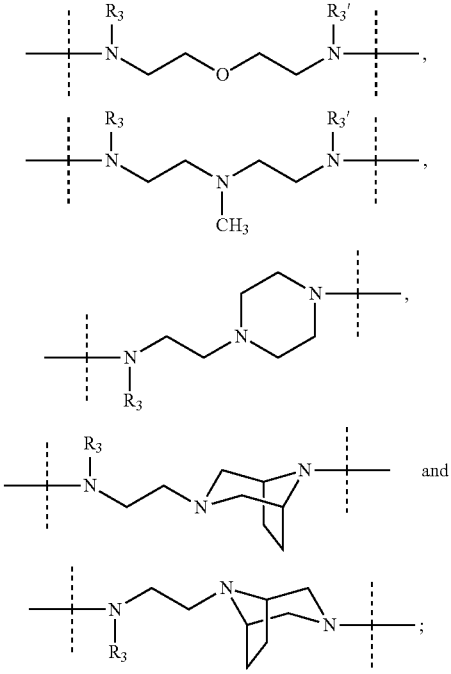

Y is selected from —$N(R_3)$—$(CH_2)_a$—$N(R_3)$— wherein a is 4 or 5,

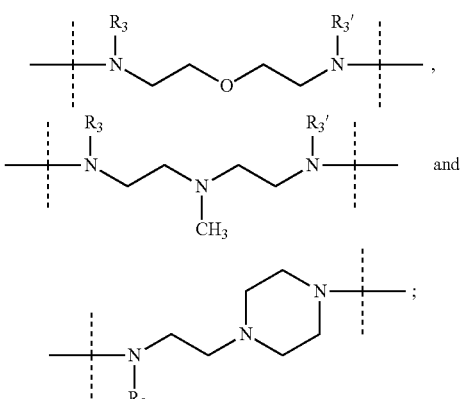

Y is selected from —$N(CH_3)$—$(CH_2)_4$—$N(CH_3)$—,

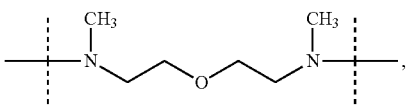

-continued

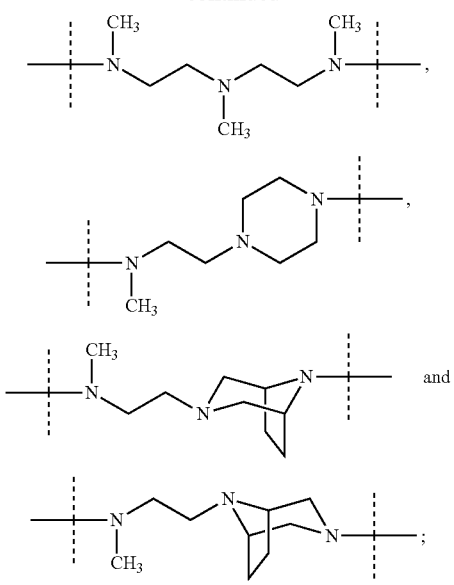

Y is selected from

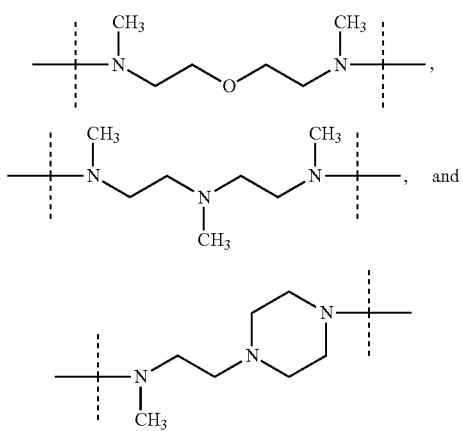

wherein the piperazine moiety is connected to the carbonyl and the aliphatic amine to the sulphonyl;

Y is selected from —N(R$_3$)—(CH$_2$)$_5$—N(R$_3$)— and

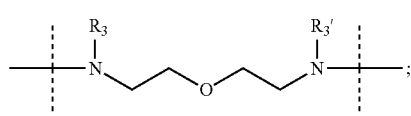

Y is

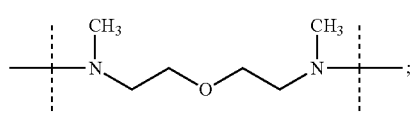

Y is

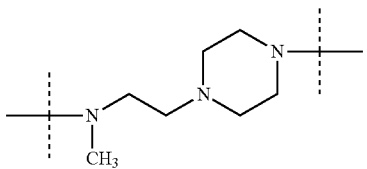

wherein the piperazine moiety is connected to the carbonyl and the aliphatic amine to the sulphonyl;

Y has a chain length of 7 atoms;
R$_3$ and R$_3$' are independently selected from the group consisting of hydrogen, methyl, ethyl, isopropyl and cyclopropyl;
R$_3$ and R$_3$' are independently selected from the group consisting of hydrogen and methyl;
R$_3$ and R$_3$' are methyl;
R$_1$ is selected from the group comprising hydrogen, chloro, fluoro or methoxy;
R$_1$ is hydrogen or methoxy or fluoro;
R$_1$ is hydrogen
R$_1$ is positioned on the benzene ring in meta or para with respect to the bond linking the benzene to the indole group;
R$_1$ is positioned on the benzene ring in para with respect to the bond linking this benzene to the indole group;
R$_2$ is selected from methyl, ethyl, iso-propyl, cyclopentyl and cyclopropyl;
R$_2$ is methyl or iso-propyl;
R$_2$ is methyl;
R$_4$ is selected from cyclopentyl, cyclohexyl, and fluorocyclohexyl, in particular, 2-fluorocyclohexyl;
R$_4$ is cyclohexyl;
n is 1;
a is 4 or 5;
In another particular embodiment when Y can be

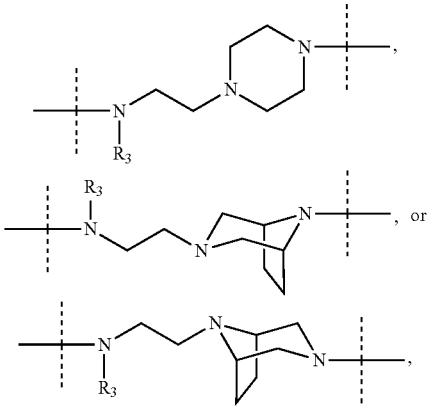

the piperazinyl or 3,8-Diaza-bicyclo[3.2.1]octane moiety is connected to the carbonyl group and the aliphatic amine is connected to the sulfonamide group.

In one embodiment, the invention provides compounds of, independently, formula (II), (III), (IV), (V), (VI) or (VII) wherein R$_4$ is cyclohexyl or 2-fluorocyclohexyl.

In another embodiment, the invention provides compounds of formula (II), (III), (IV), (V), (VI) or (VII) wherein R$_1$ is hydrogen, methoxy, chloro or fluoro.

In another embodiment, the invention provides compounds of formula (II), (III), (IV), (V), (VI) or (VII) wherein R₂ is methyl, ethyl or isopropyl.
In another embodiment, the invention provides compounds of formula (II), (III), (IV), (V), (VI) or (VII) wherein n is 1.
In a particular embodiment, the invention provides compounds of formula (I) selected from the group comprising:
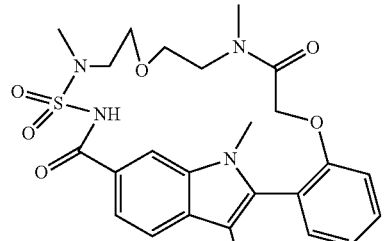
,
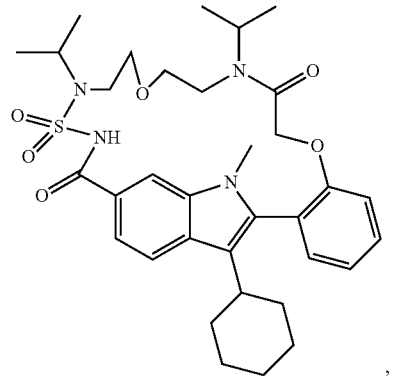
,
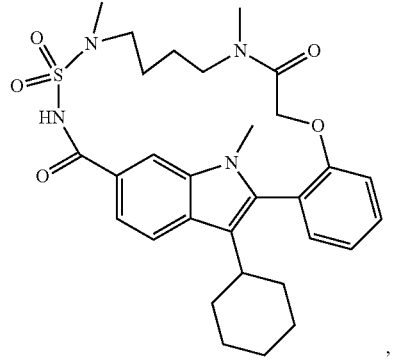
,
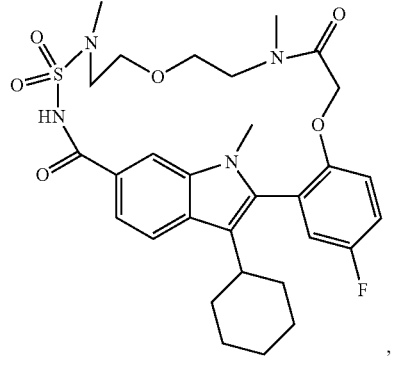 [SMILES: CN1CCN(C)C(=O)COc2ccccc2-c2c(C3CCCCC3)c3ccc(cc3n2C)C(=O)NS(=O)(=O)N(C)CC1]
,
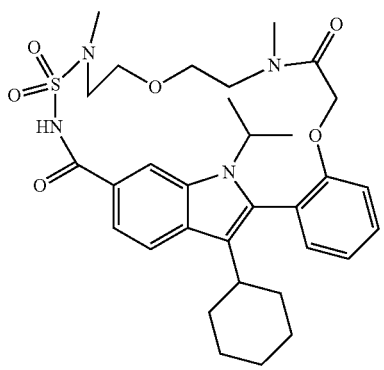
,
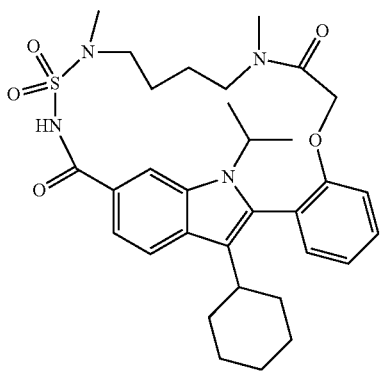
,
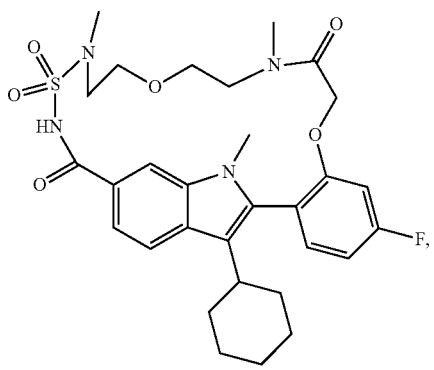
,
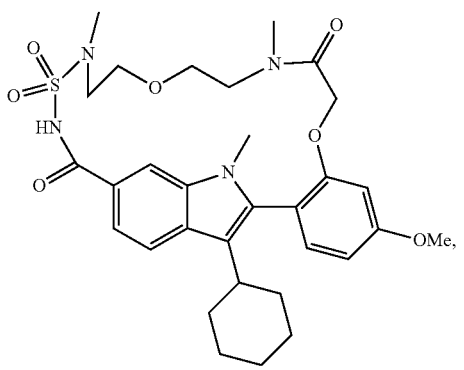

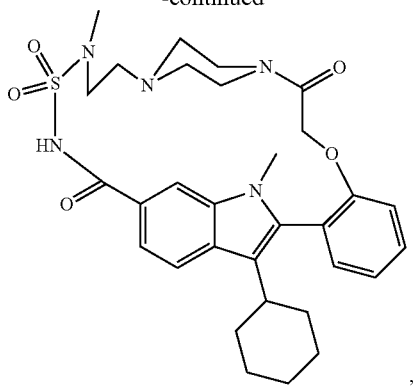

,

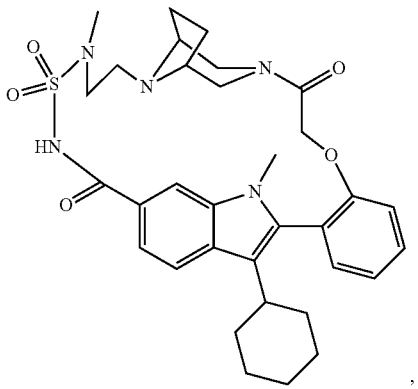

,

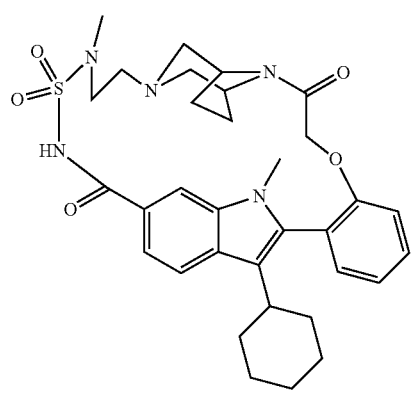

,

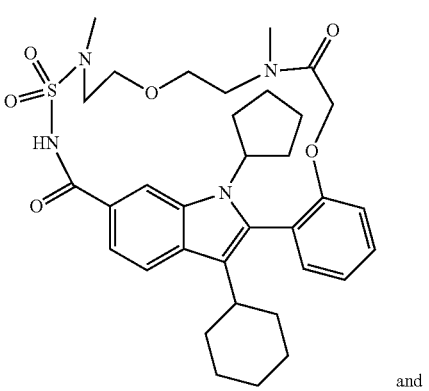

and

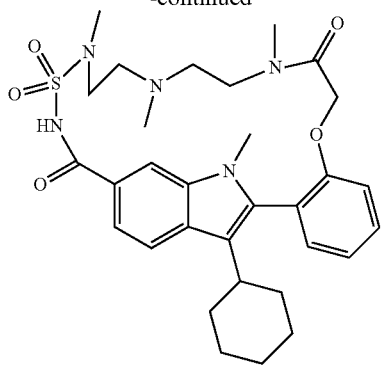

, including stereochemically isomeric forms, and salts, solvates or hydrates thereof.

Unless otherwise mentioned or indicated, the chemical designation of a compound encompasses the mixture of some or all, possible stereochemically isomeric forms, which said compound might possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided the reaction occurs stereospecifically. In particular, if a specific stereoisomer is desired, said compound is synthesized by stereospecific methods of preparation. These methods will advantageously employ enantiomerically pure starting materials.

The diastereomeric racemates of the compounds of formula (I) or any subgroup thereof, can be obtained separately by conventional methods. Appropriate physical separation methods that may advantageously be employed are, for example, selective crystallization and chromatography, e.g. column chromatography.

For some of the compounds of formula (I), their N-oxides, salts, hydrates, or solvates, and the intermediates used in the preparation thereof, the absolute stereochemical configuration was not experimentally determined. A person skilled in the art is able to determine the absolute configuration of such compounds using art-known methods such as, for example, X-ray diffraction.

However, those compounds of formula (I) that lack a chiral or stereogenic center in their chemical structure may have the advantage of facilitating the industrial scale up of the synthesis and/or an improved cost efficiency of synthesis.

Particular subgroups of compounds of formula (I) are compounds of formula (IA) and (IB).

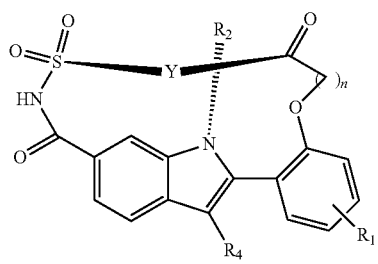

(IA)

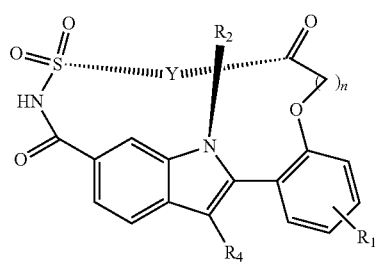

(IB)

Compounds of formula (IA) and (IB) are isomers and depending on the length of the bivalent linker Y and on $R_2$ (for example when $R_2$ is isopropyl), the compounds of formula (IA) and (IB) may not be in equilibrium but locked in their respective conformation, i.e. are stable in their respective conformations. The conformation of compounds of formula (I), e.g. (IA) or (IB), affects the compounds' characteristics including its metabolic stability, pharmacokinetics and biological activities.

Particular embodiments of compounds of formula (IA) and (IB), are compounds of formula (IA-1) and (IB-1).

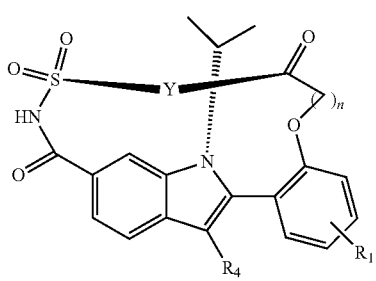

(IA-1)

-continued

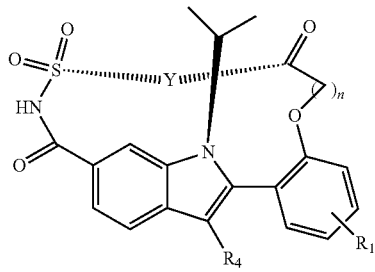

(IB-1)

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counter-ion is pharmaceutically acceptable. However, salts of acids and bases, which are non-pharmaceutically acceptable, may also find use, for example, in the preparation or purification of a pharmaceutically acceptable compound. All salts, whether pharmaceutically acceptable or not are included within the ambit of the present invention.

The pharmaceutically acceptable acid and base salts as mentioned hereinabove are meant to comprise the therapeutically active non-toxic acid and base addition salt forms that the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-amino-salicylic, pamoic and the like acids.

Conversely, said salt forms can be converted by treatment with an appropriate base into the free base form.

The compounds of formula (I) or any subgroup thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The N-oxide forms of the present compounds are the compounds of formula (I) or any subgroup thereof wherein one or several nitrogen atoms are oxidized to the so-called N-oxide. Such N-oxides may typically be formed after administration of the compound of formula (I) to a subject, upon metabolisation in the body. Alternatively, such N-oxides may be chemically synthesised using methods known in the art.

Some of the compounds of formula (I) or any subgroup thereof and intermediates may also exist in one or more tautomeric form. Such forms although not explicitly indicated in the above formula are intended to be included within the scope of the present invention. Accordingly, the compounds and intermediates may be present as a mixture of tautomers or as an individual tautomer.

In the invention, particular preference is given to compounds of Formula I or any subgroup thereof, that in the inhibition assays described below have an inhibition value of less than 100 µM, in particular less than 50 µM, more in particular less than 10 µM, in particular less than 5 µM, even more in particular less than 1 µM, preferably less than 100 nM, and in particular less than 50 nM, as determined by a suitable assay, such as the assays used in the Examples below.

It is to be understood that the above defined subgroups of compounds of formula (I) as well as any other subgroup defined herein, are meant to include stereochemically isomeric forms, and any salts, hydrates and solvates of such compounds.

Preparation of the Compounds of Formula (I)
General Synthetic Schemes

Compounds of formula (I) may be prepared following the different methods B, C, D, E, F, described below, from indole derivatives A-6, synthesized as described in method A,

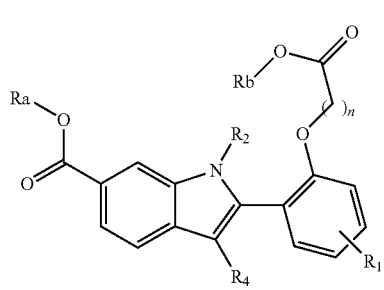

wherein $R_1$, $R_2$, $R_4$, n are as defined for compounds of formula (I) or subgroups thereof, and Ra is selected from methyl and tert-butyl and Rb is selected from methyl or tert-butyl. The synthesis of A-1 is described in WO 2003/010140A2, *Journal of Medicinal Chemistry* 2005, vol. 48(5), pages 1314-1317, and WO 2006/029912A1.

Method A

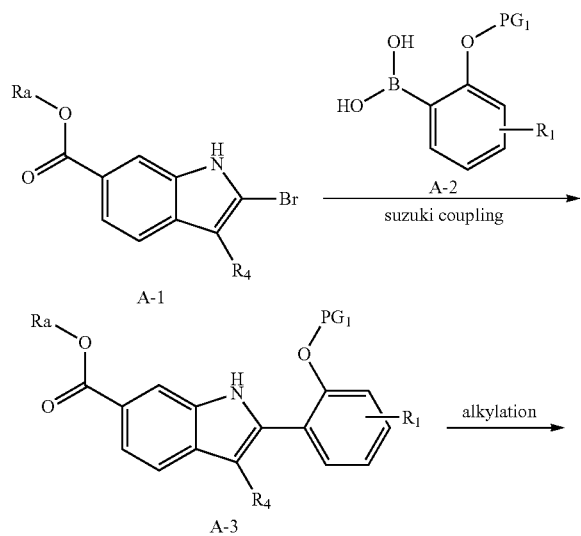

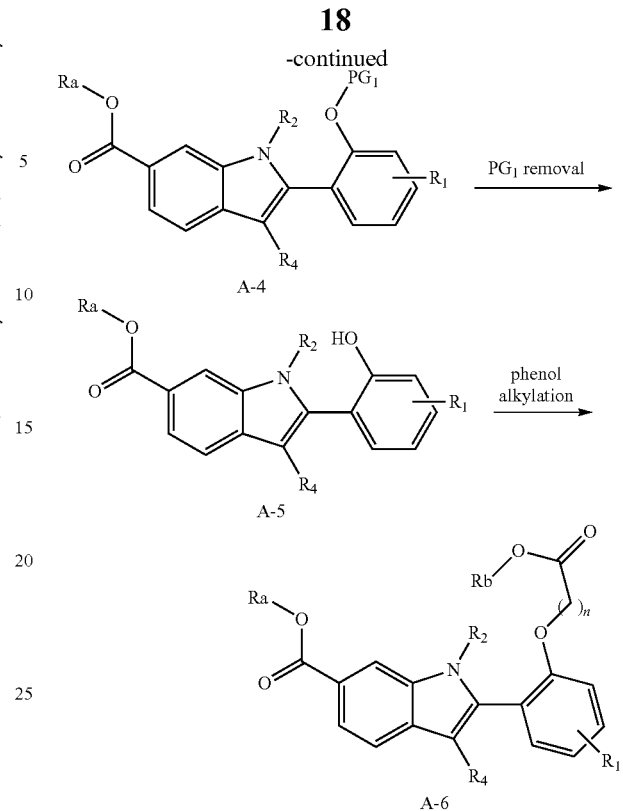

Compounds of formula A-3 may be obtained by a Suzuki cross-coupling reaction, between compounds A-1 bearing a $R_4$ substituent and a methyl or tert-butylester, and a boronic acid derivative A-2, bearing a $R_1$ substituent and a hydroxyl protected by a suitable protecting group $PG_1$, such as a benzyl group. Further appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987). This reaction may be performed in the presence of a palladium catalyst, such as diCl-bis(triphenylphosphino)-Pd(II), and a base, such as potassium carbonate, and in a suitable solvent such as a mixture of dimethoxyethane/water, or toluene/ethanol/water, under an inert atmosphere.

Compounds A-4 may be obtained by alkylation of compounds A-3, using an alkyl halide derivative, for example methyliodide, in the presence of a base such as sodium hydride, potassium carbonate, cesium carbonate and the like, in the presence of a suitable solvent such as DMF, THF, acetonitrile and the like.

Compounds A-5 may be obtained by removal of the phenol protecting group $PG_1$ by methods known in the art. Appropriate deprotection methods for the $PG_1$ used are described by Greene, "Protective Groups in Organic Chemistry", John Wiley & Sons, New York (1999) and "The Peptides: Analysis, Synthesis, Biology", Vol. 3, Academic Press, New York (1987). For example, the benzyl protecting group can be removed by catalytic hydrogenation using a palladium catalyst in a suitable solvent such as methanol.

Compounds A-6 may be obtained by an alkylation reaction of the phenol, using for example a halo acetate derivative of formula X—CH$_2$—CO—O—Rb wherein X is halo. The alkylation reaction may be performed in the presence of a base such as potassium carbonate, cesium carbonate and the like, in a suitable solvent such as DMF, THF, acetonitrile and the like. The Rb substituent may be a methyl when Ra is a methyl or a tert-butyl, or a tert-butyl when Ra is a methyl.

Method B

A schematic overview for the synthesis of the compounds of formula (I) is given in scheme 2. The method starts from a compound of formula A-6.

Compounds of formula B-1 may be prepared by the regioselective hydrolysis of the ester bearing the Rb group. For those compounds A-6 wherein Rb is a methyl group and Ra is a tert-butyl group or a methyl group, the regioselective hydrolysis of the Rb ester may be performed under basic conditions, using a hydroxide such as LiOH or NaOH, in polar solvents such as water, an alcohol such as methanol or ethanol, tetrahydrofurane (THF), or a mixture thereof. Alternatively, when Rb is a tert-butyl group, the regioselective hydrolysis of the ester bearing the Rb group may be performed under acidic conditions, using for example TFA in a suitable solvent, like DCM.

A monoprotected bifunctional Y derived reagent of formula $PG_2$-Y—H wherein Y is as defined for formula (I) or subgroups thereof, may then be coupled to the carboxylic acid of compounds B-1 to form an amide bond, leading to compounds B-2. "$PG_2$", as used herein, is a suitable amine protecting group, chosen from the ones known in the art. Appropriate protecting groups that can be used as $PG_2$ are listed for example in Greene, "Protective Groups in Organic Chemistry", John Wiley & Sons, New York (1999). In particular, $PG_2$ is a tert-butyloxycarbonyl (Boc) protecting group or a 2-nitrobenzenesulfonyl (nosyl) group.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

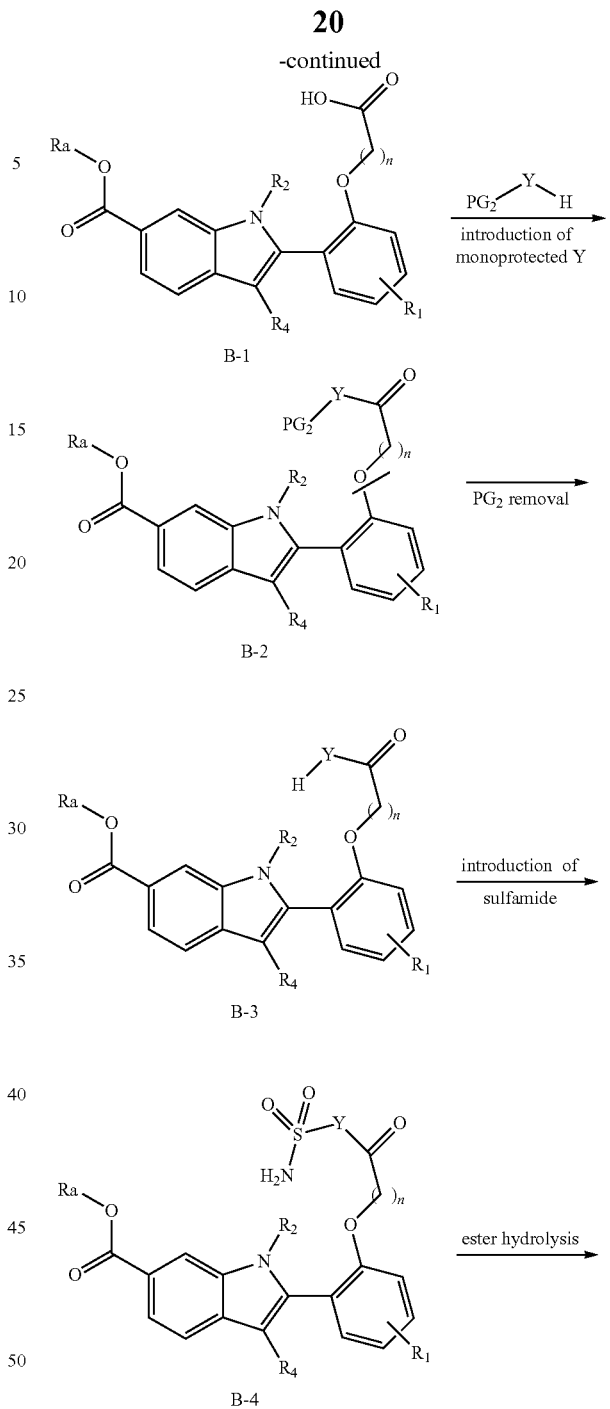

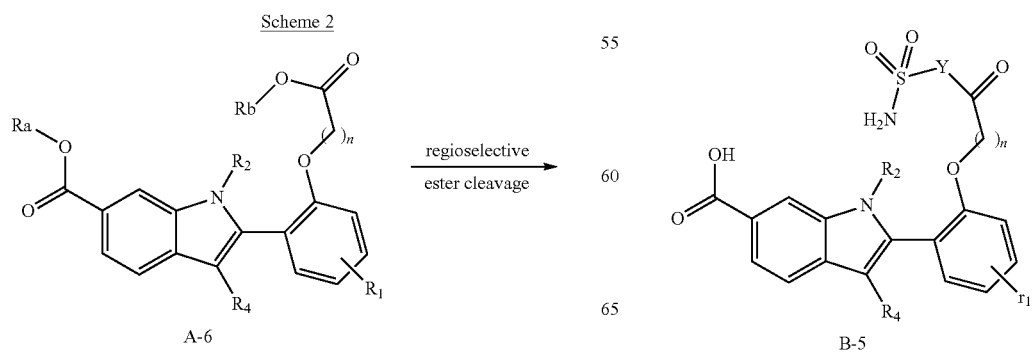

Scheme 2

-continued

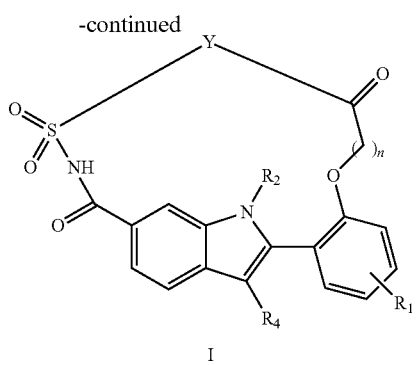

I

Examples of coupling reactions with amide bond formation include the azide method, mixed carbonic-carboxylic acid anhydride (isobutyl chloroformate) method, the carbodiimide (dicyclohexylcarbodiimide (DCC), diisopropylcarbodiimide (DIC), or water-soluble carbodiimide such as N-ethyl-N'-[3-(dimethylamino)propyl]carbodiimide (EDC)) method, the active ester method (e.g. p-nitrophenyl, p-chlorophenyl, trichlorophenyl, pentachlorophenyl, pentafluorophenyl, N-hydroxysuccinic imido and the like esters), the Woodward reagent K-method, the 1,1-carbonyldiimidazole (CDI or N,N'-carbonyldiimidazole) method, the phosphorus reagents or oxidation-reduction methods. Some of these methods can be enhanced by adding suitable catalysts, e.g. in the carbodiimide method by adding 1-hydroxybenzotriazole, or 4-dimethylaminopyridine (4-DMAP). Further coupling agents are (benzotriazol-1-yloxy)-tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed either in solution (liquid phase) or on solid phase.

The coupling reactions in particular are conducted in an inert solvent, such as halogenated hydrocarbons, e.g. dichloromethane (DCM), chloroform, dipolar aprotic solvents such as acetonitrile, dimethylformamide (DMF), dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicyclo[5.4.0]undec-7-ene (DBU). The reaction temperature may range between 0° C. and 50° C. and the reaction time may range between 15 min and 24 h.

Removal of the protecting group $PG_2$ following methods known in the art may lead to compounds B-3. For example, when $PG_2$ is a Boc-protecting group, $PG_2$ may be removed by treating compounds B-2 with trifluoro acetic acid (TFA) in a suitable solvent such as DCM. When $PG_2$ is a nosyl group, $PG_2$ may be removed by treating compounds B-2 with a thiol like mercapto acetic acid or thiophenol, in solution or in solid phase, in the presence of a base, such as cesium carbonate or LiOH, in a suitable solvent, such as DMF, THF. When Ra is a tert-butyl group and $PG_2$ is a Boc-protecting group, removal of $PG_2$ as described above, may lead to a compound B-3, with Ra being OH.

In the next step, for the introduction of a sulfamide, compounds B-3 may be reacted with sulfamide, in a suitable solvent, for example dioxane, under heating conditions, e.g. about 100° C. This reaction may take place under microwave irradiation and lead to compounds B-4. Alternatively, the sulfamide moiety may be introduced by reaction of compound B-3 with aminosulfonylchloride, in the presence of a suitable base, such as triethylamine, DIPEA, or pyridine, in a suitable solvent, such as a chlorinated solvent like DCM, or DMF, THF.

The remaining ester function of compounds B-4, i.e. —CO—O—Ra, may then be hydrolyzed, using conditions known in the art, and including the saponification in basic media as described above, leading to compounds B-5. Heating may be required to complete this reaction. Acidic conditions may also be used to hydrolyze the ester function of compounds B-4, for example TFA in a suitable solvent like DCM, when Ra is a tent-butyl group.

Compounds (I) may be obtained by macrocyclisation by forming the intramolecular acylsulfamide bond, in the presence of coupling agents, such as CDI that converts the carboxylic acid group to a reactive species acylimidazole, under heating. This acylimidazole may then be purified before adding a suitable base such as DBU, in order to perform the ring closure, which may take place under heating conditions. Solvents used for these reactions may include acetonitrile or THF. Other coupling agents or conditions, such as those known in the art or described herein above, may also be used to achieve the ring closure.

Method C

Scheme 3

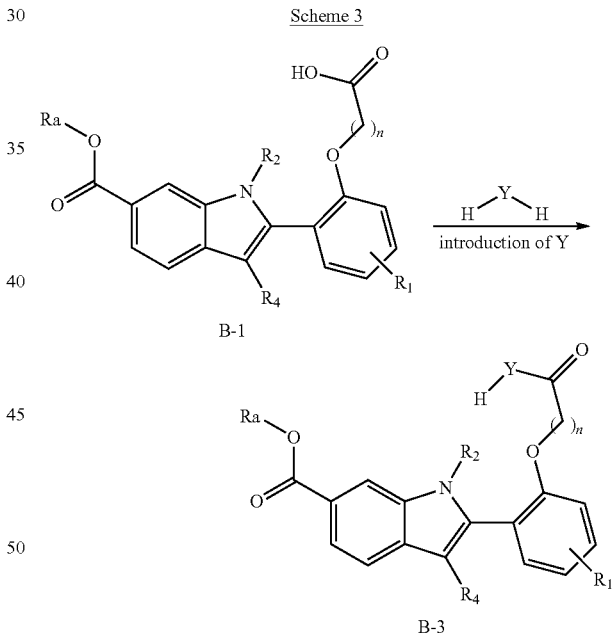

An alternative method leading to compounds B-3 as illustrated in scheme 3, may be the formation of an amide bond between compounds B-1 and a symmetrical bivalent chain Y, used in excess compared to compounds B-1. This amide bond may be synthesized as described above, in particular using a coupling agent such as [dimethylamino-([1,2,3]triazolo[4,5-b]pyridin-3-yloxy)-methylene]-dimethyl-ammonium hexafluorophosphate (HATU), in the presence of a base such as DIPEA and in a suitable solvent like DCM, DMF, or more in particular THF. Compounds B-3 may then be reacted as described above in method B in order to prepare compounds (I).

Method D

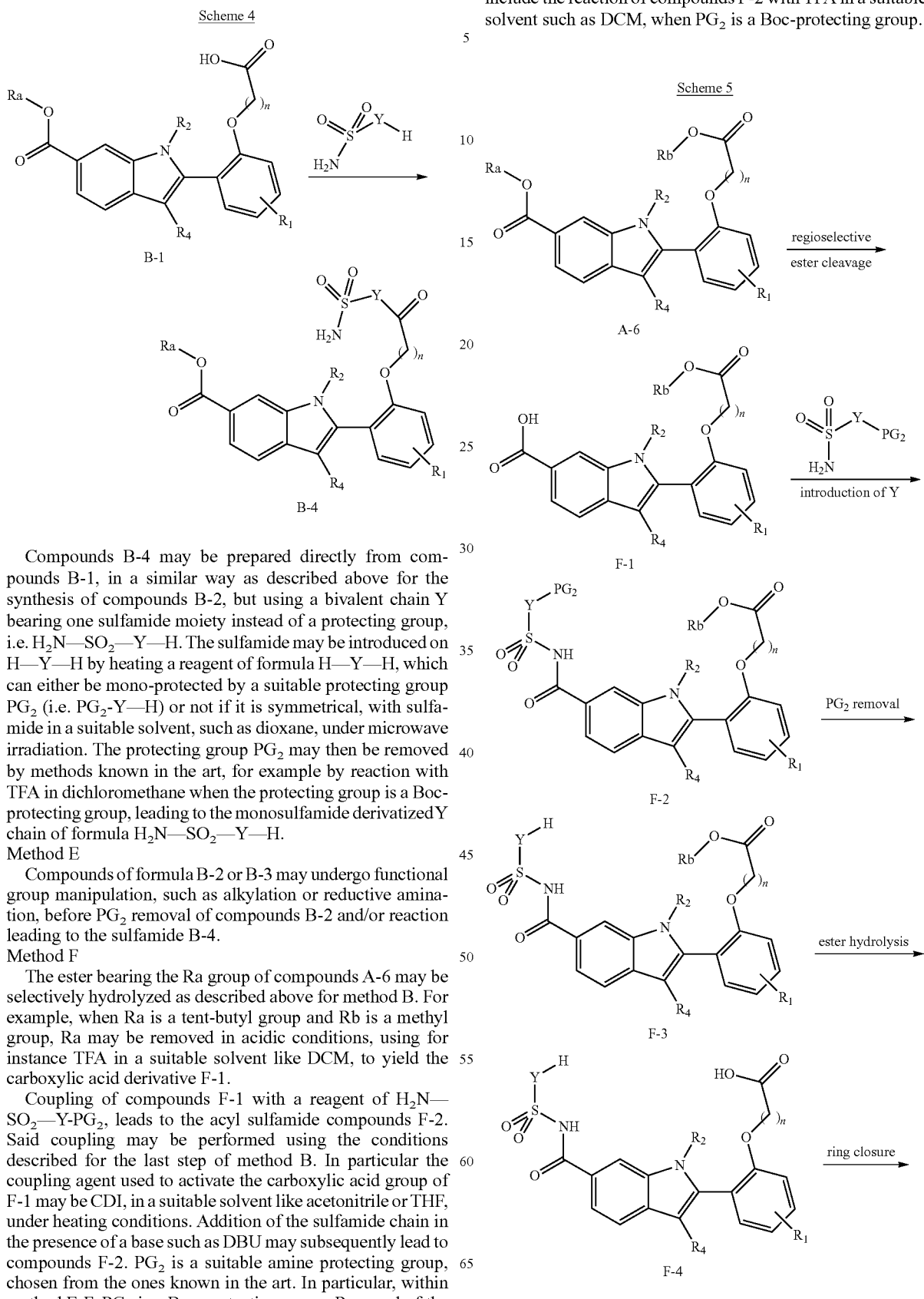

Compounds B-4 may be prepared directly from compounds B-1, in a similar way as described above for the synthesis of compounds B-2, but using a bivalent chain Y bearing one sulfamide moiety instead of a protecting group, i.e. $H_2N—SO_2—Y—H$. The sulfamide may be introduced on H—Y—H by heating a reagent of formula H—Y—H, which can either be mono-protected by a suitable protecting group $PG_2$ (i.e. $PG_2$-Y—H) or not if it is symmetrical, with sulfamide in a suitable solvent, such as dioxane, under microwave irradiation. The protecting group $PG_2$ may then be removed by methods known in the art, for example by reaction with TFA in dichloromethane when the protecting group is a Boc-protecting group, leading to the monosulfamide derivatized Y chain of formula $H_2N—SO_2—Y—H$.

Method E

Compounds of formula B-2 or B-3 may undergo functional group manipulation, such as alkylation or reductive amination, before $PG_2$ removal of compounds B-2 and/or reaction leading to the sulfamide B-4.

Method F

The ester bearing the Ra group of compounds A-6 may be selectively hydrolyzed as described above for method B. For example, when Ra is a tent-butyl group and Rb is a methyl group, Ra may be removed in acidic conditions, using for instance TFA in a suitable solvent like DCM, to yield the carboxylic acid derivative F-1.

Coupling of compounds F-1 with a reagent of $H_2N—SO_2—Y-PG_2$, leads to the acyl sulfamide compounds F-2. Said coupling may be performed using the conditions described for the last step of method B. In particular the coupling agent used to activate the carboxylic acid group of F-1 may be CDI, in a suitable solvent like acetonitrile or THF, under heating conditions. Addition of the sulfamide chain in the presence of a base such as DBU may subsequently lead to compounds F-2. $PG_2$ is a suitable amine protecting group, chosen from the ones known in the art. In particular, within method E-F, $PG_2$ is a Boc-protecting group. Removal of the protecting group $PG_2$ of compounds F-2 following methods known in the art may lead to compounds F-3. These methods include the reaction of compounds F-2 with TFA in a suitable solvent such as DCM, when $PG_2$ is a Boc-protecting group.

-continued

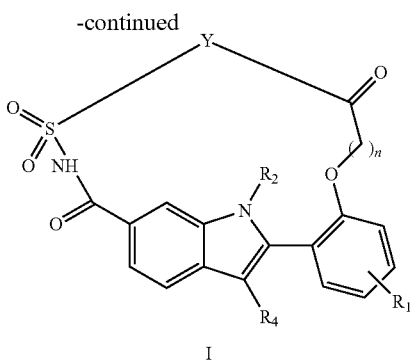

I

The ester function of compounds F-3 (wherein Rb is a methyl group) may then be hydrolyzed, using conditions known in the art, including the saponification in basic media as described above, leading to compounds F-4.

Alternatively, compounds F-2 may undergo the saponification reaction in basic media to hydrolyze the ester bearing Rb, prior to the removal of the amine protecting group $PG_2$ using the conditions described above, and leading to compounds F-4.

Compounds (I) may be obtained by macrocyclisation of compounds F-4 by forming the intramolecular amide bond, in the presence of coupling agents, as described in method B. In particular this amide formation step may be performed under high dilution conditions.

Pure stereochemically isomeric forms of the compounds of formula (I) or any subgroups thereof may be obtained by the application of art-known procedures. Diastereomers may be separated by physical methods such as selective crystallization and chromatographic techniques, e.g., counter-current distribution, liquid chromatography and the like.

The compounds of formula (I) or any subgroups thereof may be obtained as racemic mixtures of enantiomers, which can be separated from one another following art-known resolution procedures. The racemic compounds of formula (I) or any subgroups thereof, which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) or any subgroups thereof involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. In particular if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) or any subgroups thereof, as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I) or any subgroups thereof, as specified herein.

Therefore, according to an embodiment of the present invention, the compounds of formula (I) or any subgroup thereof may be formulated into various pharmaceutical forms for administration purposes. It is understood that all compositions usually employed for systemically administering drugs are included as appropriate compositions. To prepare the pharmaceutical compositions of this invention, an effective amount of the particular compound, optionally in salt form or a metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

It has been found that compounds of the present invention display a favourable pharmacokinetic prophile after oral administration, i.e. high liver concentration and high liver-to-plasma ratio. It is advantageous for compounds that inhibit HCV replication to display high liver concentrations as HCV replicates in the liver. A high liver-to-plasma ratio may reduce the side effect and/or lower the minimum dosage.

Thus, the present invention also provides a pharmaceutical composition adapted for administration by inhalation or insufflation through the mouth comprising a compound of formula (I) or any subgroups thereof and a pharmaceutically acceptable carrier. In particular, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) and any subgroup thereof show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis.

However, compounds of the invention may also be particularly attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

Due to their antiviral properties, particularly their anti-HCV properties, the compounds of formula (I) or any subgroup thereof, including stereochemically isomeric forms, and their N-oxides, salts, hydrates and solvates, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to virally infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), or any subgroups thereof, as specified herein.

The present invention also concerns combinations of a compound of formula (I) or any subgroup thereof, as specified herein with other anti-HCV agents. In an embodiment, the invention concerns combination of a compound of Formula (I) or any subgroup thereof with at least one anti-HCV agent. In a particular embodiment, the invention concerns combination of a compound of Formula (I) or any subgroup thereof with at least two anti-HCV agents. In a particular embodiment, the invention concerns combination of a compound of Formula (I) or any subgroup thereof with at least three anti-HCV agents. In a particular embodiment, the invention concerns combination of a compound of Formula (I) or any subgroup thereof with at least four anti-HCV agents.

The combination of previously known anti-HCV compound, such as interferon-α (IFN-α), pegylated interferon-α, ribavirin or a combination thereof, and, a compound of formula (I) or any subgroup thereof can be used as a medicine in a combination therapy. In an embodiment, the term "combination therapy" relates to a product containing mandatory (a) a compound of formula (I), and (b) at least one other anti-HCV compound, as a combined preparation for simultaneous, separate or sequential use in treatment of HCV infections, in particular, in the treatment of infections with HCV.

Anti-HCV compounds encompass agents selected from HCV polymerase inhibitors, R-7128, MK-0608, ABT-33, VCH759, PF-868554, GS9190, NM283, valopicitabine, PSI-6130, XTL-2125, NM-107, R7128 (R4048), GSK625433, R803, R-1626, BILB-1941, HCV-796, JTK-109 and JTK-003, ANA-598, IDX-184, MK-3281, MK-1220, benzimidazole derivatives, benzo-1,2,4-thiadiazine derivatives, phenylalanine derivatives, A-831 and A-689; HCV proteases (NS2-NS3 and NS3-NS4A) inhibitors, the compounds of WO02/18369 (see, e.g., page 273, lines 9-22 and page 274, line 4 to page 276, line 11), BI-1335, TMC435350, MK7009, ITMN-191, BILN-2061, VX-950, BILN-2065, BMS-605339, VX-500, SCH 503034; inhibitors of other targets in the HCV life cycle, including helicase, and metalloprotease inhibitors, ISIS-14803; immunomodulatory agents such as, α-, β-, and γ-interferons such as rIFN-α 2b, rIFN-α 2ba, consensus IFN-α (infergen), feron, reaferon, intermax α, rIFN-β, infergen+actimmune, IFN-omega with DUROS, albuferon, locteron, Rebif, Oral IFN-α, IFN-α 2b XL, AVI-005, pegylated-infergen, pegylated derivatized interferon-α compounds such as pegylated rIFN-α 2b, pegylated rIFN-α 2a, pegylated IFN-β, compounds that stimulate the synthesis of interferon in cells, interleukins, Toll like receptor (TLR) agonists, compounds that enhance the development of type 1 helper T cell response, and thymosin; other antiviral agents such as ribavirin, ribavirin analogs such as rebetol, copegus and viramidine (taribavirin), amantadine, and telbivudine, inhibitors of internal ribosome entry, alpha-glucosidase 1 inhibitors such as MX-3253 (celgosivir) and UT-231B, hepatoprotectants such as IDN-6556, ME-3738, LB-84451 and MitoQ, broad-spectrum viral inhibitors, such as IMPDH inhibitors (e.g., compounds of U.S. Pat. Nos. 5,807,876, 6,498,178, 6,344,465, 6,054,472, WO97/40028, WO98/40381, WO00/56331, mycophenolic acid and derivatives thereof, and including, but not limited to VX-497, VX-148, and/or VX-944); and other drugs for treating HCV such as zadaxin, nitazoxanide, BIVN-401 (virostat), PYN-17 (altirex), KPE02003002, actilon (CPG-10101), KRN-7000, civacir, GI-5005, ANA-975, XTL-6865, ANA-971, NOV-205, tarvacin, EHC-18, NIM811, DEBIO-025, VGX-410C, EMZ-702, AVI 4065, Bavituximab, and Oglufanide; or combinations of any of the above.

Thus, to combat or treat HCV infections, the compounds of formula (I) or any subgroups thereof may be co-administered in combination with for instance, interferon-α (IFN-α), pegylated interferon-α, ribavirin or a combination thereof, as well as therapeutics based on antibodies targeted against HCV epitopes, small interfering RNA (si RNA), ribozymes, DNAzymes, antisense RNA, small molecule antagonists of for instance NS3 protease, NS3 helicase and NS5B polymerase.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy in particular comprising a compound of formula (I) and at least one other HCV inhibitory compound, e.g. IFN-α, pegylated IFN-α, ribavirin or a combination thereof.

Furthermore, it is known that a large percentage of patients infected with human immunodeficiency virus 1 (HIV) are also infected with HCV, i.e. they are HCV/HIV co-infected. HIV infection appears to adversely affect all stages of HCV infection, leading to increased viral persistence and accelerated progression of HCV-related liver disease. In turn, HCV infection may affect the management of HIV infection, increasing the incidence of liver toxicity caused by antiviral medications.

The present invention therefore also concerns combinations of a compound of Formula (I) or any subgroup thereof with anti-HIV agents. Also, the combination of one or more additional anti-HIV compounds and a compound of Formula (I) or any subgroups thereof can be used as a medicine. In particular, said combination can be used for inhibition HCV and HIV replication.

The term "combination therapy" also encompasses a product comprising (a) a compound of Formula (I) or any subgroup thereof, and (b) at least one anti-HIV compound, and (c) optionally at least one other anti-HCV compound, as a combined preparation for simultaneous, separate or sequential use in treatment of HCV and HIV infections, in particular, in the treatment of infections with HCV and HIV, or for preventing or treating conditions associated with HCV and HIV.

Thus, the present invention also relates to a product containing (a) at least one compound of Formula (I) or any subgroup thereof, and (b) one or more additional anti-HIV compounds, as a combined preparation for simultaneous, separate or sequential use in anti-HCV and anti-HIV treatment. The different drugs may be combined in a single preparation together with pharmaceutically acceptable carriers. Said anti-HIV compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126,443), AVX 754 ((−)-dOTC), fozivudine tidoxil (FZT), phosphazide, HDP-990003, KP-1461, MIV-210, racivir (PSI-5004), UC-781 and the like; non-nucleoside reverse transcriptase inhibitors (NNRTIs) such as delavirdine (DLV), efavirenz (EFV), nevirapine (NVP), dapivirine (TMC120), etravirine (TMC125), rilpivirine (TMC278), DPC-082, (+)-Calanolide A, BILR-355, and the like; nucleotide reverse transcriptase inhibitors (NtRTIs), e.g. tenofovir ((R)-PMPA) and tenofovir disoproxil fumarate (TDF), and the like; nucleotide-competing reverse transcriptase inhibitors (NcRTIs), e.g. NcRTI-1 and the like; inhibitors of trans-activating proteins, such as TAT-inhibitors, e.g. RO-5-3335, BI-201, and the like; REV inhibitors; protease inhibitors e.g. ritonavir (RTV), saquinavir (SQV), lopinavir (ABT-378 or LPV), indinavir (IDV), amprenavir (VX-478), TMC126, nelfinavir (AG-1343), atazanavir (BMS 232, 632), darunavir (TMC114), fosamprenavir (GW433908 or VX-175), brecanavir (GW-640385, VX-385), P-1946, PL-337, PL-100, tipranavir (PNU-140690), AG-1859, AG-1776, Ro-0334649 and the like; entry inhibitors, which comprise fusion inhibitors (e.g. enfuvirtide (T-20)), attachment inhibitors and co-receptor inhibitors, the latter comprise the CCR5 antagonists (e.g. ancriviroc, CCR5 mAb004, maraviroc (UK-427,857), PRO-140, TAK-220, TAK-652, vicriviroc (SCH-D, SCH-417,690)) and CXR4 antagonists (e.g. AMD-070, KRH-27315), examples of entry inhibitors are PRO-542, TNX-355, BMS-488043, BlockAide/CR™, FP 21399, hNM01, nonakine, VGV-1; a maturation inhibitor for example is PA-457; inhibitors of the viral integrase e.g. raltegravir (MK-0518), elvitegravir (JTK-303, GS-9137), BMS-538158; ribozymes; immunomodulators; monoclonal antibodies; gene therapy; vaccines; siRNAs; antisense RNAs; microbicides; Zinc-finger inhibitors.

Therefore, HCV infected patients also suffering from conditions associated with HIV or even other pathogenic retroviruses, such as AIDS, AIDS-related complex (ARC), progressive generalized lymphadenopathy (PGL), as well as chronic CNS diseases caused by retroviruses, such as, for example HIV mediated dementia and multiple sclerosis, can conveniently be treated with the present composition.

The compositions may be formulated into suitable pharmaceutical dosage forms such as the dosage forms described above. Each of the active ingredients may be formulated separately and the formulations may be co-administered or one formulation containing both and if desired further active ingredients may be provided.

As used herein, the term "composition" is intended to encompass a product comprising the specified ingredients, as well as any product that results, directly or indirectly, from the combination of the specified ingredients.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers as well to combinations comprising two or more agents, the "therapeutically effective amount" in the context of combinations is also that amount of the agents taken together so that the combined effect elicits the desired biological or medicinal response. For example, the therapeutically effective amount of a composition comprising (a) the compound of formula (I) and (b) another anti-HCV agent, would be the amount of the compound of formula (I) and the amount of the other anti-HCV agent that when taken together have a combined effect that is therapeutically effective.

In general, it is contemplated that an antiviral effective daily amount would be from 0.01 mg/kg to 500 mg/kg body weight, more in particular from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

In one embodiment of the present invention there is provided an article of manufacture comprising a composition effective to treat an HCV infection or to inhibit the NS5B polymerase of HCV; and packaging material comprising a label which indicates that the composition can be used to treat infection by the hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, in an amount effective for use as a standard or reagent in a test or assay for determining the ability of potential pharmaceuticals to inhibit HCV NS5B polymerase, HCV growth, or both. This aspect of the invention may find its use in pharmaceutical research programs.

The compounds and combinations of the present invention can be used in high-throughput target-analyte assays such as those for measuring the efficacy of said combination in HCV treatment.

EXAMPLES

The following examples are intended to illustrate the present invention and not to limit it thereto. Unless otherwise indicated, purification of the synthesized compounds by column chromatography or flash chromatography is performed a silica gel column.

Unless otherwise indicated, the final products were characterized by LCMS analysis using a SunFire C18 3.5μ 4.6×100 mm column and two mobile phases: mobile phase A (10 mM ammonium formiate (NH$_4$OOCH)+0.1% HCOOH in H$_2$O) and mobile phase B (CH$_3$CN). The temperature of the column was 50° C., the flow 2 mL/min and the gradient of mobile phase A and mobile phase B was characterized as it follows:

| time(min)      | 0  | 5.4 | 7.2 | 7.3 | 9  |
|----------------|----|-----|-----|-----|-----|
| % mobile phase A | 95 | 5   | 5   | 95  | 95 |
| % mobile phase B | 5  | 95  | 95  | 5   | 5  |

Characterizing data generated by the LCMS analysis are the HPLC retention time (Rt) and confirmation on the molecular mass (m/z).

Example 1

Synthesis of 25-cyclohexyl-4,10,19-trimethyl-5,6,9,10-tetrahydro-2H,8H-14,18:17,20-di(metheno)-1,7,11,4,10,12,19-benzodioxathiatetraazacyclodocosine-3,13 (4H,12H,19H)-dione 11,11-dioxide 10

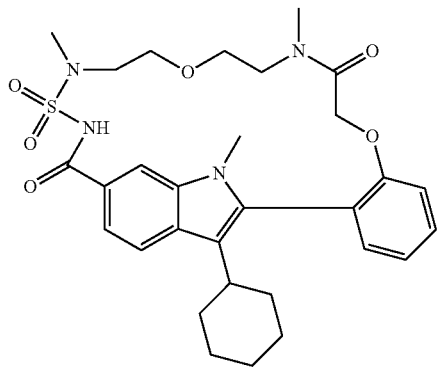

Step 1

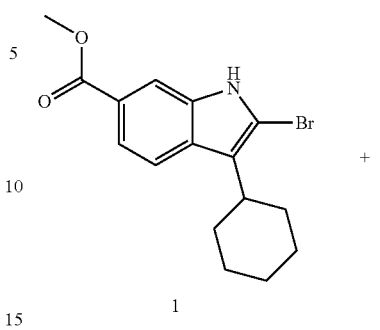

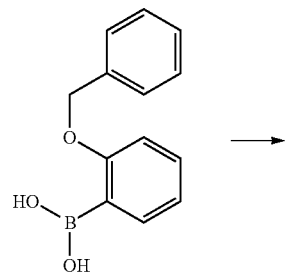

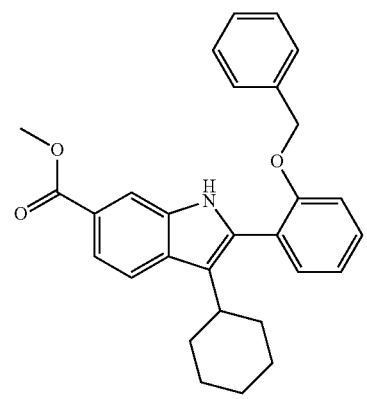

A solution of methyl 2-bromo-3-cyclohexyl-1H-indole-6-carboxylate (1, 6.14 g, 18.3 mmol), 2-(benzyloxy)phenylboronic acid (5.00 g, 21.9 mmol) and potassium carbonate (5.80 g, 42 mmol) in 450 mL of 1,2-dimethoxyethane/water (4:1) was thoroughly flushed with argon. Then trans-BIS(triphenylphosphine)palladium(II) chloride (0.641 g, 0.91 mmol) was added and the reaction was heated at 70° C. under argon for 12 h. The reaction mixture was cooled to room temperature, diluted with water and extracted with ethylacetate (AcOEt). Combined organic layers were washed with a saturated solution of NaHCO$_3$ and brine, dried over anhydrous Na$_2$SO$_4$ and filtered. The filtered solution was concentrated under vacuum to give methyl 2-[2-(benzyloxy)phenyl]-3-cyclohexyl-1H-indole-6-carboxylate 2: m/z=440 (M+H)$^+$.

Step 2

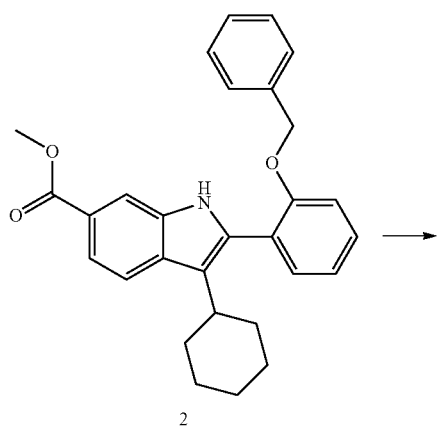
2

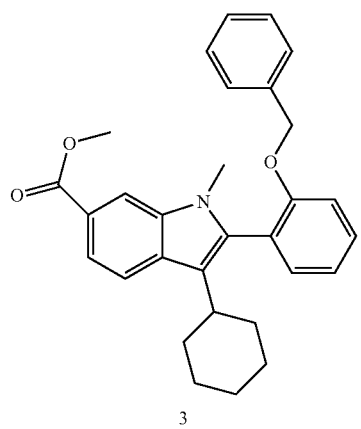
3

NaH (810 mg, 32.1 mmol) was added to a solution of intermediate 2 (9.4 g, 21.4 mmol) in dry DMF. Then, iodomethane (3.64 g, 25.7 mmol) was added at room temperature. After 12 h, the reaction mixture was partitioned between water (pH 6) and AcOEt. Organic layer was dried over anhydrous Na$_2$SO$_4$, filtered and then evaporated. The residue was purified by silica column chromatography (gradient heptane/AcOEt 1:0 to 80:20) to yield 7.8 g (80%) of methyl 2-[2-(benzyloxy)phenyl]-3-cyclohexyl-1-methyl-1H-indole-6-carboxylate 3: m/z=454 (M+H)$^+$.

Step 3

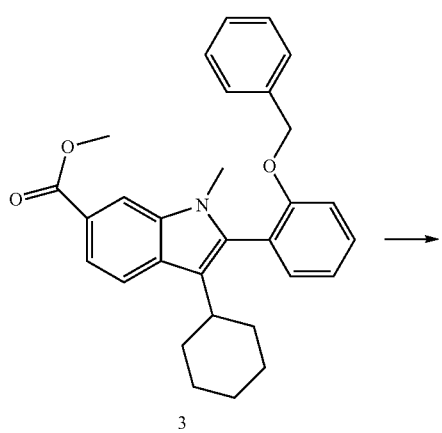
3

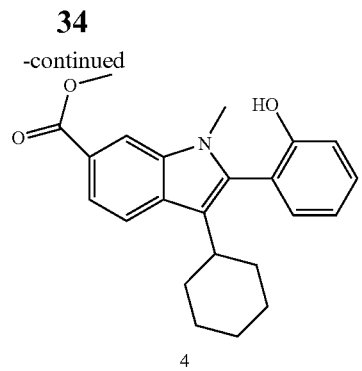
4

A solution of intermediate 3 (4.00 g) in MeOH (36 mL) and AcOH (4 mL) was hydrogenated in presence of palladium hydroxide as catalyst. After 12 h, the reaction mixture was filtered and the filtrate was evaporated to give methyl 3-cyclohexyl-2-(2-hydroxyphenyl)-1-methyl-1H-indole-6-carboxylate 4: m/z=364 (M+H)$^+$.

Step 4

4

5

A solution of intermediate 4 (4.00 g, 11.0 mmol), tent-butyl 2-bromoacetate (2.36 g, 12.1 mmol) and potassium carbonate (3.04 g, 22.0 mmol) was stirred at room temperature. After 72 h, the reaction mixture was concentrated under vacuum and the residue was partitioned between CH$_2$Cl$_2$ and water. The organic layer was dried and the residue was reconstituted in CH$_2$Cl$_2$ (20 mL) and TFA (20 mL) was added. After 2 h at room temperature, the reaction mixture was evaporated under vacuum to yield 4.2 g (90%) of {2-[3-cyclohexyl-6-(methoxycarbonyl)-1-methyl-1H-indol-2-yl]phenoxy}acetic acid 5: m/z=422 (M+H)$^+$.

Step 5

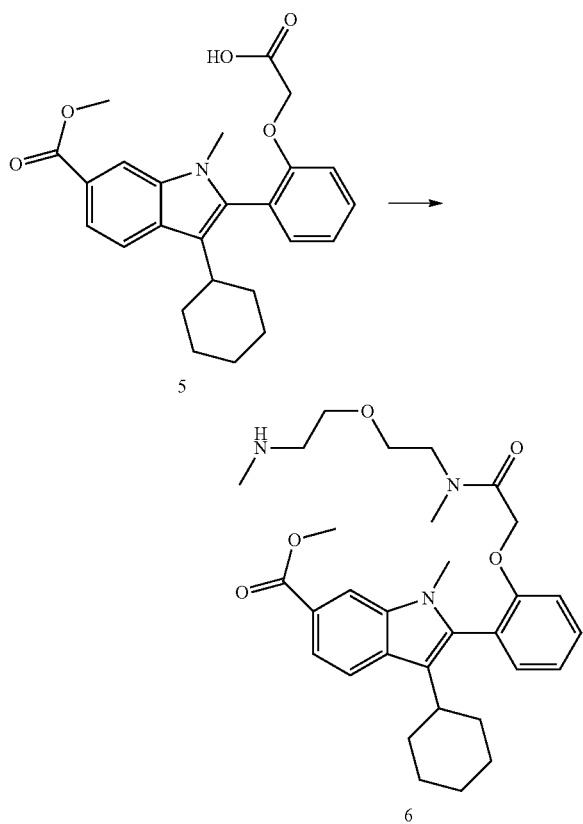

A solution of intermediate 5 (650 mg, 1.54 mmol), N-methyl-2-(methylaminoethyloxy)ethylamine (1.02 g, 7.71 mmol), diisopropylethylamine (808 µL, 4.63 mmol) and HATU (880 mg, 2.31 mmol) in dry THF (25 mL) was stirred at room temperature overnight. Then, the reaction mixture was concentrated under vacuum. The residue was partitioned between AcOEt and water. The organic layer was dried over anhydrous $Na_2SO_4$ and evaporated to yield 750 mg (91%) of methyl 3-cyclohexyl-1-methyl-2-{2-[2-(methyl {2-[2-(methylamino)ethoxy]ethyl}amino)-2-oxoethoxy]phenyl}-1H-indole-6-carboxylate 6: m/z=536 (M+H)$^+$.

Step 6

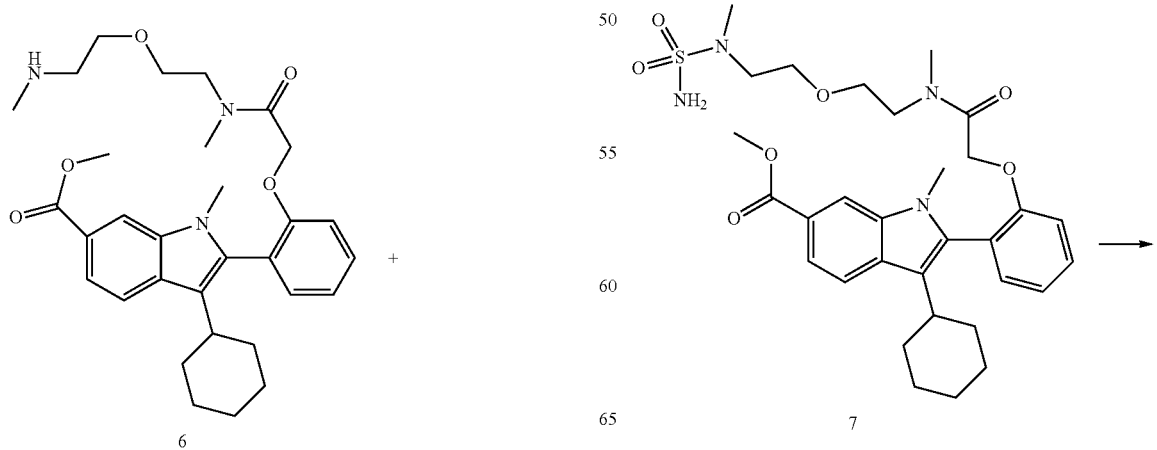

A solution of intermediate 6 (620 mg, 1.16 mmol) and sulfamide (900 mg, 9.36 mmol) in dioxane (10 mL) was heated at 100° C. in a microwave oven for 60 minutes. The reaction mixture was cooled down to room temperature, and then evaporated under vacuum. The residue was triturated in water, filtered and washed with water. The powder was reconstituted in AcOEt. The solution was dried over anhydrous $Na_2SO_4$, filtered and the filtrate evaporated to yield 610 mg (86%) of methyl 3-cyclohexyl-1-methyl-2-(2-{2-[methyl(2-{2-[methyl(sulfamoyl)amino]ethoxy}ethyl)amino]-2-oxoethoxy}phenyl)-1H-indole-6-carboxylate 7 as a yellowish powder: m/z=615 (M+H)$^+$.

Step 7

-continued

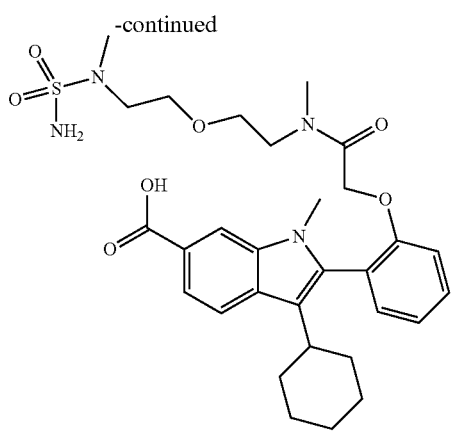

8

A solution of NaOH (1.00 g, 25 mmol) in water (5 mL) was added to a stirred solution of intermediate 7 (370 mg, 0.602 mmol) in MeOH (30 mL) and THF (10 mL). After 5 h, the solution was concentrated under vacuum. The pH was then adjusted to 5 with acetic acid (AcOH). Then, the reaction mixture was extracted with AcOEt, the organic layer dried over anhydrous $Na_2SO_4$, filtered and the filtrate evaporated to yield 300 mg (83%) of 3-cyclohexyl-1-methyl-2-(2-{2-[me-thyl(2-{2-[methyl(sulfamoyl)amino]ethoxy}ethyl)amino]-2-oxoethoxy}phenyl)-1H-indole-6-carboxylic acid 8 as a white powder: m/z=601 (M+H)$^+$.

Step 8

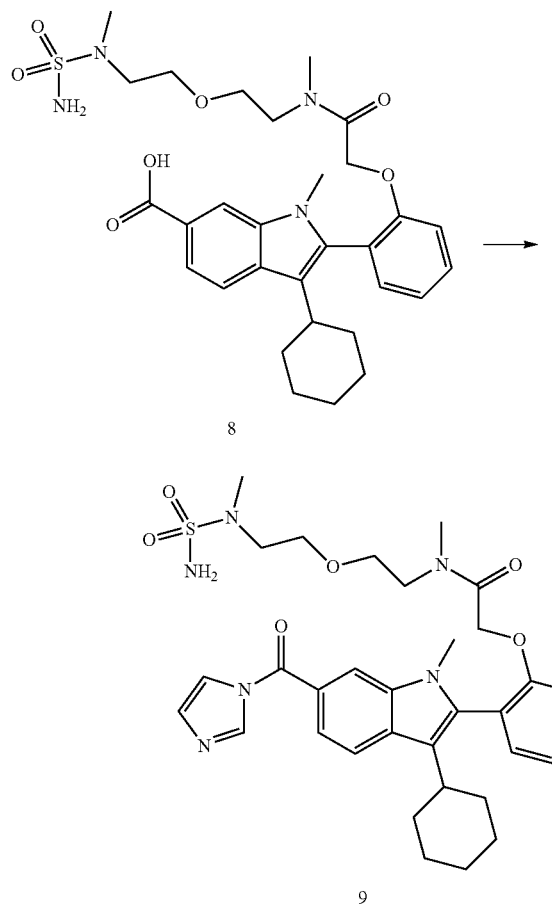

Carbonyldiimidazole (405 mg, 2.50 mmol) was added to a stirred solution of intermediate 8 (300 mg, 0.50 mmol) in dry acetonitrile ($CH_3CN$) (25 mL). The reaction mixture was stirred at room temperature for 1 h, upon which complete conversion was observed. The resulting solution was evaporated and the residue was purified by silica flash chromatography (gradient AcOEt/$CH_3CN$ 1:0 to 0:1) to yield 315 mg (97%) of 2-{2-[3-cyclohexyl-6-(1H-imidazol-1-ylcarbonyl)-1-methyl-1H-indol-2-yl]phenoxy}-N-methyl-N-(2-{2-[methyl(sulfamoyl)amino]ethoxy}ethyl)acetamide 9 as a white powder: m/z=651 (M+H)$^+$.

Step 9

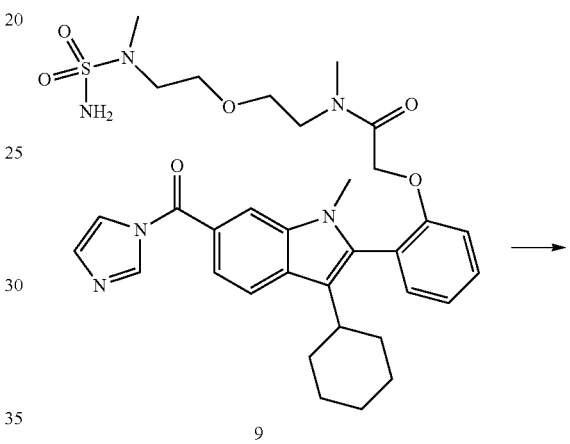

9

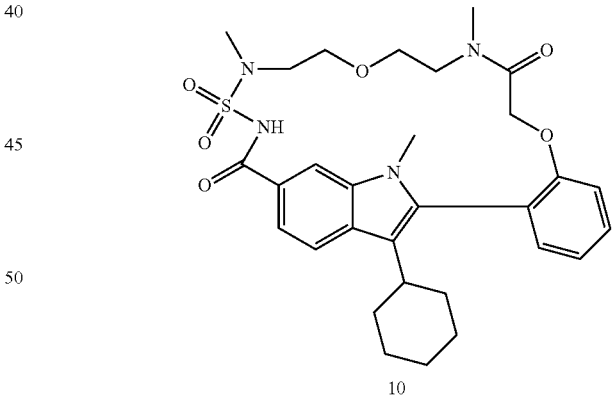

10

DBU (147 mg, 0.97 mmol) was added to a solution of 9 (315 mg, 0.48 mmol) in $CH_3CN$ (5 mL). The reaction mixture was stirred overnight at room temperature. Then, the pH of the reaction mixture was adjusted to 5 with AcOH. The solution was evaporated. The residue was purified first by silica column chromatography (gradient AcOEt/$CH_3CN$ 1:0 to 0:1), and then by preparative HPLC to yield the desired product 25-cyclohexyl-4,10,19-trimethyl-5,6,9,10-tetrahydro-2H,8H-14, 18:17,20-di(metheno)-1,7,11,4,10,12,19-benzo-dioxathiatetraazacyclodocosine-3,13(4H,12H,19H)-dione 11,11-dioxide 10: m/z=583 (M+H)$^+$, Rt=5.13 min.

Example 2

Synthesis of 24-cyclohexyl-4,9,18-trimethyl-4,5,6,7,8,9-hexahydro-13,17:16,19-di(metheno)-1,10,4,9,11,18-benzoxathiatetraazacyclohenicosine-3,12(2H,11H,18H)-dione 10,10-dioxide 15

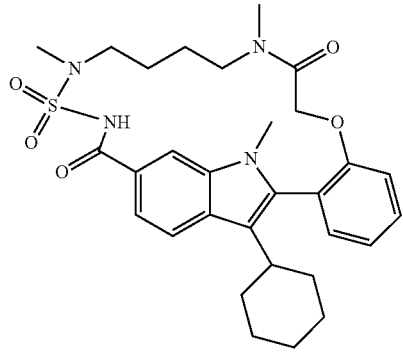

Step 1.

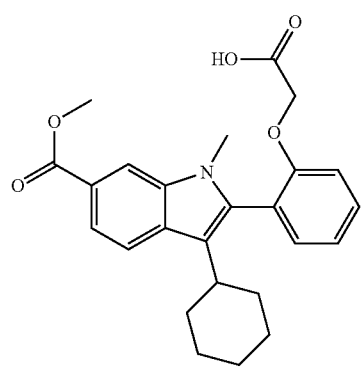

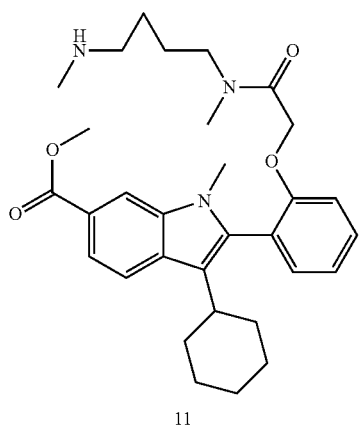

Compound 11 was synthesized in 88% yield from intermediate 5 and N,N'-dimethylbutylene diamine following the procedure reported for the synthesis of methyl 3-cyclohexyl-1-methyl-2-[2-(2-{methyl[4-(methylamino)butyl]amino}-2-oxoethoxy)phenyl]-1H-indole-6-carboxylate 6: m/z=520 (M+H)$^+$.

Step 2.

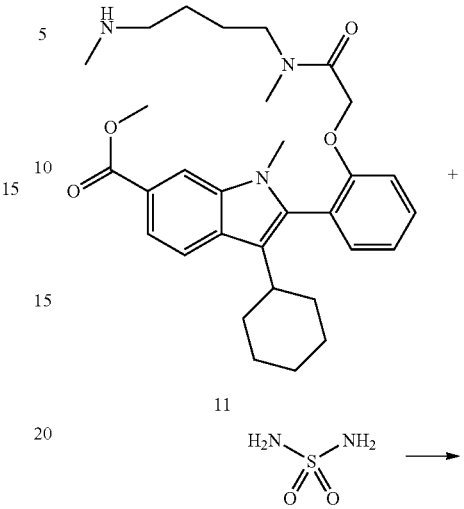

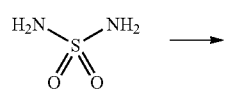

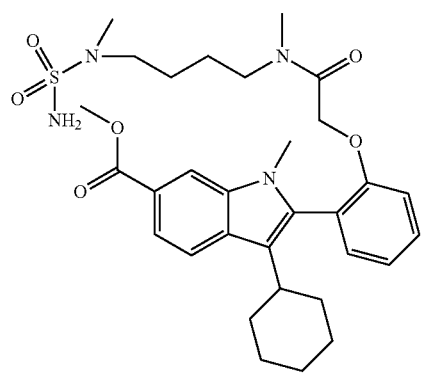

Methyl 3-cyclohexyl-1-methyl-2-{2-[2-(methyl {4-[methyl(sulfamoyl)amino]butyl}amino)-2-oxoethoxy]phenyl}-1H-indole-6-carboxylate 12 was synthesized in 68% yield from intermediate 11 following the procedure reported for the synthesis of intermediate 7: m/z=599 (M+H)$^+$.

Step 3.

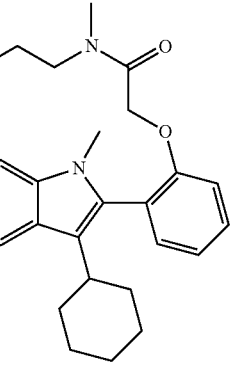

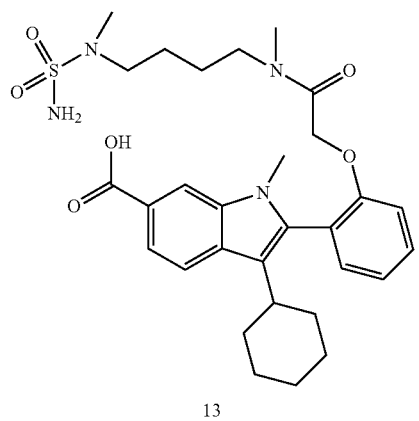

13

3-cyclohexyl-1-methyl-2-{2-[2-(methyl {4-[methyl(sulfamoyl)amino]butyl}amino)-2-oxoethoxy]phenyl}-1H-indole-6-carboxylic acid 13 was synthesized in 78% yield from intermediate 12 following the procedure reported for the synthesis of intermediate 8: m/z=585 (M+H)$^+$.

Step 4.

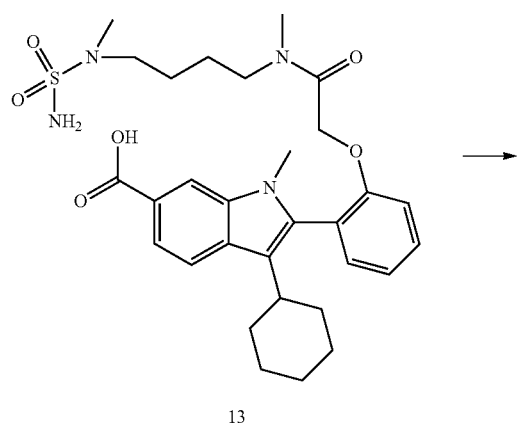

13

2-{2-[3-cyclohexyl-6-(1H-imidazol-1-ylcarbonyl)-1-methyl-1H-indol-2-yl]phenoxy}-N-methyl-N-{4-[methyl(sulfamoyl)amino]butyl}acetamide 14 was synthesized in 92% yield from intermediate 13 following the procedure reported for the synthesis of intermediate 9: m/z=635 (M+H)$^+$.

Step 5.

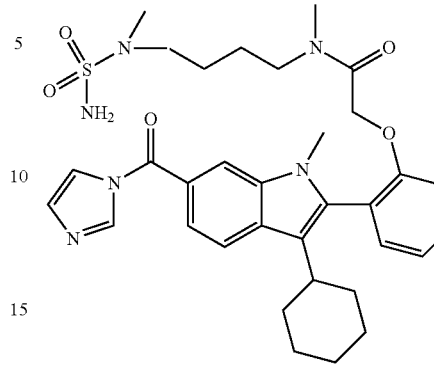

14

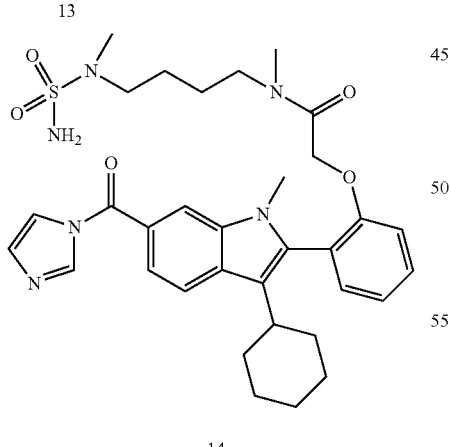

15

24-cyclohexyl-4,9,18-trimethyl-4,5,6,7,8,9-hexahydro-13,17:16,19-di(metheno)-1,10,4,9,11,18-benzoxathiatetraazacyclohenicosine-3,12(2H,11H,18H)-dione 10,10-dioxide 15 was synthesized in 12% yield from intermediate 14 following the procedure reported for the synthesis of product 10: m/z=567 (M+H)$^+$, Rt=5.07 min.

Example 3

Synthesis of 25-cyclohexyl-10,19-dimethyl-5,6,7,8,9,10-hexahydro-2H-14,18:17,20-di(metheno)-1,11,4,10,12,19-benzoxathiatetraazacyclodocosine-3,13(4H,12H,19H)-dione 11,11-dioxide 21

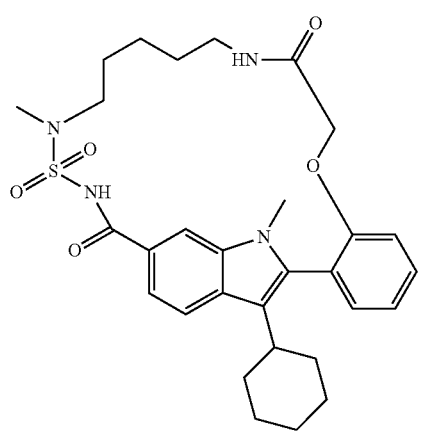

21

Step 1

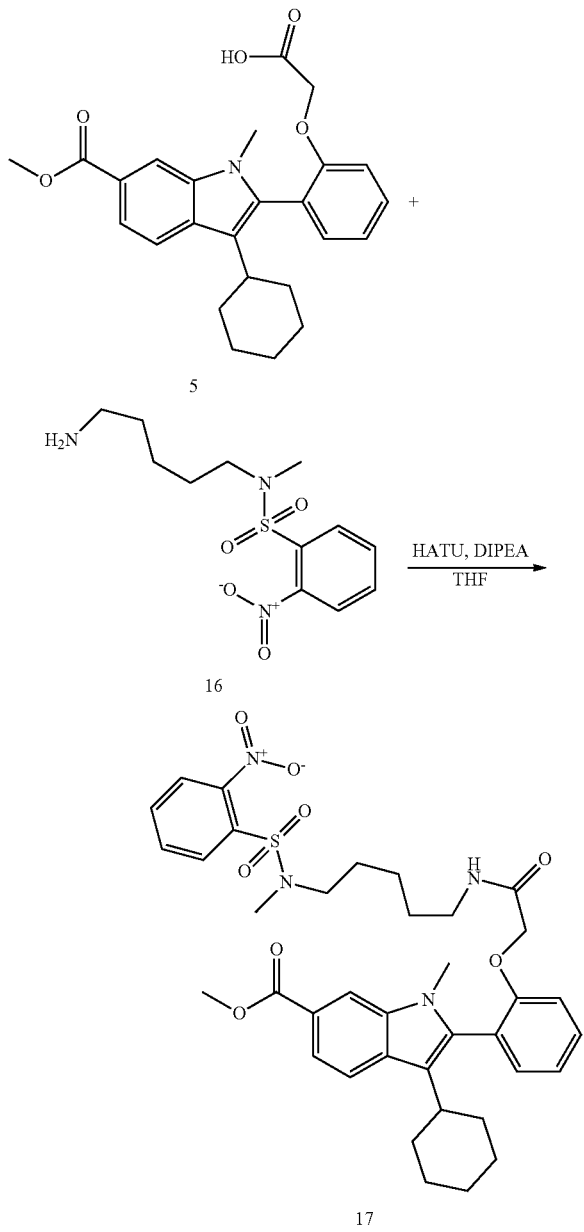

Step 2

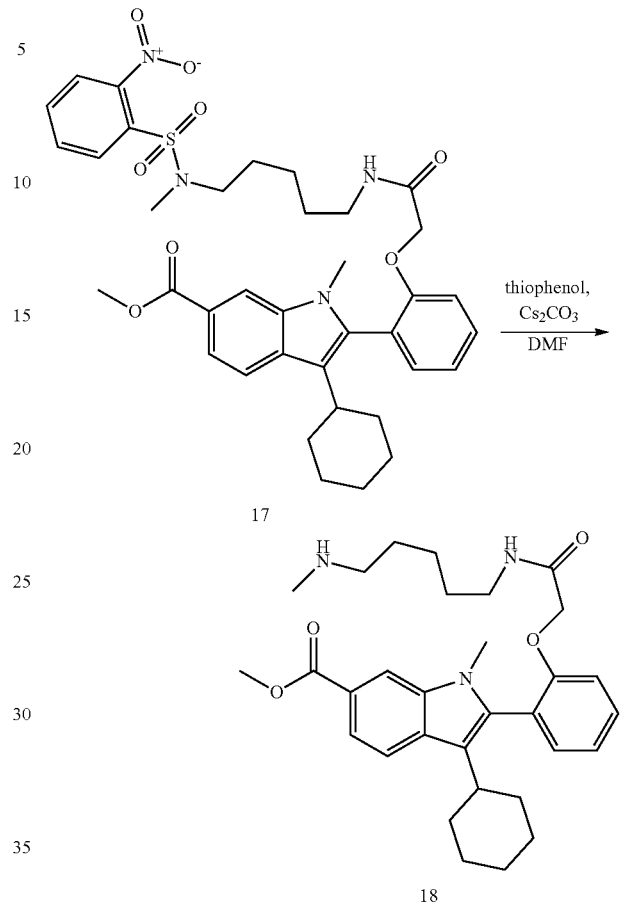

To a solution of methyl 3-cyclohexyl-1-methyl-2-(2-{2-[(5-{methyl[(2-nitrophenyl)sulfonyl]amino}pentyl)amino]-2-oxoethoxy}phenyl)-1H-indole-6-carboxylate 17 (1.27 g, 1.802 mmole) in dry DMF (50 mL) were added thiophenol (0.397 g, 2 eq) and cesium carbonate (1.174 g, 2 eq) at RT. The RM was stirred during 40 h, then was successively poured into an iced water solution, extracted with dichloromethane, dried over MgSO$_4$ and concentrated. The residue was purified by column chromatography using a gradient of ethyl acetate in DCM as eluent, to give 600 mg (64%) of the title product methyl 3-cyclohexyl-1-methyl-2-[2-(2-{[5-(methylamino)pentyl]amino}-2-oxoethoxy)phenyl]-1H-indole-6-carboxylate 18 as a white foam; m/z=520 (M+H)$^+$.

Step 3

A solution of 2-(2-(3-cyclohexyl-6-(methoxycarbonyl)-1-methyl-1H-indol-2-yl)phenoxy)acetic acid 5 (1 g, 2.373 mmol), N-(5-aminopentyl)-N-methyl-2-nitrobenzene-sulfonamide 16 (0.715 g, 1 eq), diisopropylethylamine (0.92 g, 3 eq) and HATU (1.353 g, 1.5 eq) in dry THF (25 mL) was stirred at room temperature overnight. Then, the reaction mixture was successively poured in water, extracted with dichloromethane, dried over MgSO$_4$ and concentrated. The resulting residue was purified by flash chromatography using a gradient of methanol in DCM as eluent, to give 1.27 g (76% yield) of the title product methyl 3-cyclohexyl-1-methyl-2-(2-{2-[(5-{methyl[(2-nitrophenyl)sulfonyl]amino}pentyl)amino]-2-oxoethoxy}phenyl)-1H-indole-6-carboxylate 17; m/z=705 (M+H)$^+$.

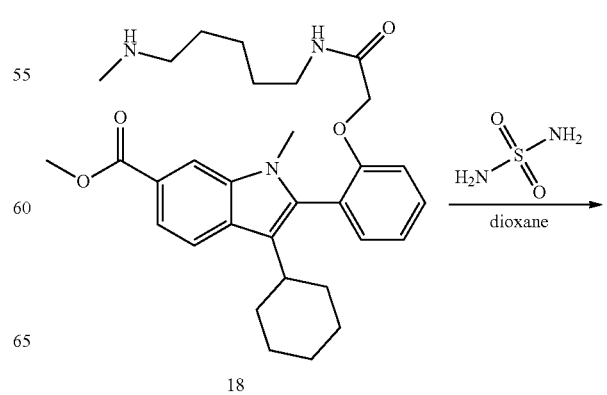

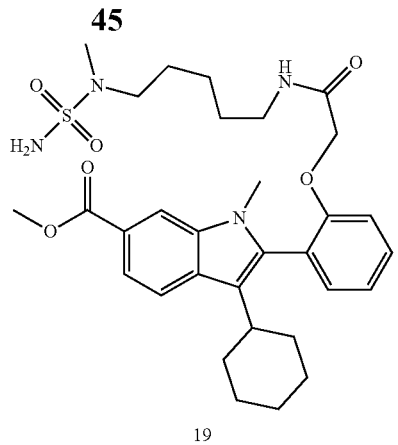

19

To a solution of methyl 3-cyclohexyl-1-methyl-2-[2-(2-{[5-(methylamino)pentyl]amino}-2-oxoethoxy)phenyl]-1H-indole-6-carboxylate 18 (0.460 g, 0.885 mmol) in dioxane (10 mL) was added sulfamide (0.851 g, 8.85 mmol). The resulting mixture was stirred at 100° C. in a microwave oven for 4 hours, then at 105° C. during 6 h. The reaction mixture was cooled down to room temperature then concentrated. The residue was triturated in dichloromethane and the resulting precipitate of excess sulfamide was filtered off. The solvent was then removed and the residue was purified by column chromatography using a gradient of methanol in dichloromethane to give 447 mg (84%) of the title product methyl 3-cyclohexyl-1-methyl-2-{2-[2-({5-[methyl(sulfamoyl)amino]pentyl}amino)-2-oxoethoxy]phenyl}-1H-indole-6-carboxylate 19; m/z=599 (M+H)⁺.

Step 4

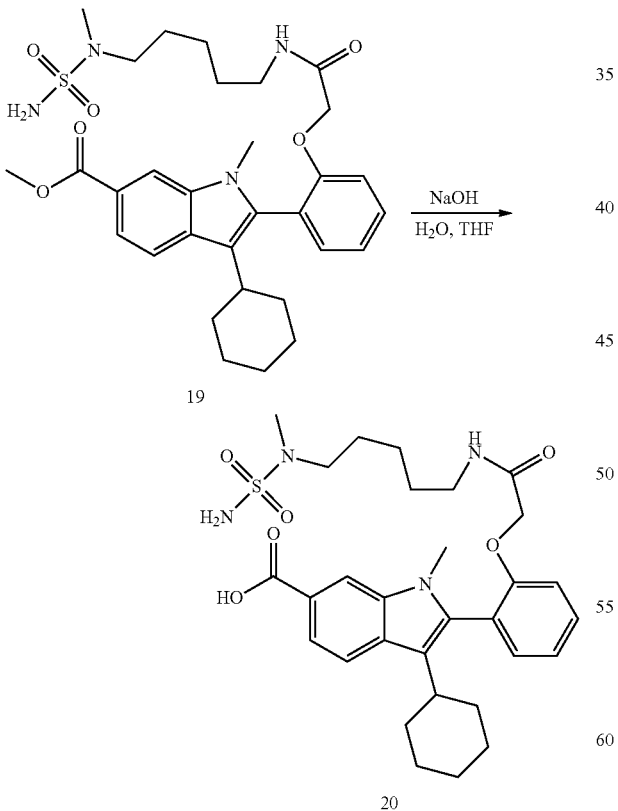

To a solution of methyl 3-cyclohexyl-1-methyl-2-{2-[2-({5-[methyl(sulfamoyl)amino]pentyl}amino)-2-oxoethoxy]phenyl}-1H-indole-6-carboxylate 19 (480 mg, 0.802 mmole) in THF (50 mL) was added a solution of sodium hydroxide (1.283 g, 40 eq) in water. The resulting mixture was stirred at RT overnight. The mixture was then successively poured in water, acidified until pH=5 with HCl, extracted with dichloromethane, dried over MgSO₄ and concentrated. The residue was purified by column chromatography using a gradient of methanol in DCM to give 330 mg (70%) of the title product 3-cyclohexyl-1-methyl-2-{2-[2-({5-[methyl(sulfamoyl)amino]pentyl}amino)-2-oxoethoxy]phenyl}-1H-indole-6-carboxylic acid 20 as a white solid; m/z=585 (M+H)⁺.

Step 5

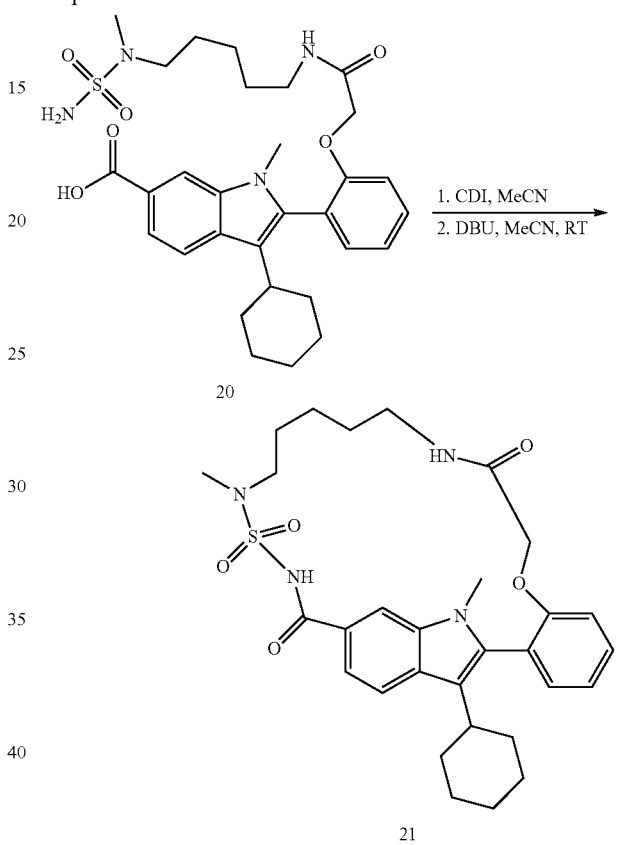

Carbonyldiimidazole (110 mg, 0.677 mmol) was added to a stirred solution of 3-cyclohexyl-1-methyl-2-{2-[2-({5-[methyl(sulfamoyl)amino]pentyl}amino)-2-oxoethoxy]phenyl}-1H-indole-6-carboxylic acid 20 (330 mg, 0.554 mmol) in dry acetonitrile (CH₃CN) (25 mL). The reaction mixture was stirred at room temperature for 2 h, upon which complete conversion was observed. The RM was then diluted with acetonitrile (25 mL) and DBU (172 mg, 2 eq) was added. The reaction mixture was stirred overnight at room temperature. The solvent was then removed under vacuum, and the resulting residue was successively dissolved in dichloromethane, washed with a solution of 2M HCl two times, then brine. The resulting organic layer was dried over sodium sulfate and concentrated. The residue was purified by column chromatography using a gradient of ethylacetate in dichloromethane to yield 220 mg (69%) of the title product 25-cyclohexyl-10,19-dimethyl-5,6,7,8,9,10-hexahydro-2H-14, 18:17,20-di(metheno)-1,11,4,10,12,19-benzoxathiatetraazacyclodocosine-3,13(4H,12H,19H)-dione 11,11-dioxide 21 as a white powder; m/z=567 (M+H)⁺.

¹H NMR (400 MHz, CDCl₃) δ ppm 0.85-0.9 (m, 1H), 1.00-1.40 (m, 7H), 1.4-1.5 (m, 2H), 1.75-1.85 (m, 7H), 2.2-

2.25 (m, 1H), 2.5-2.6 (m, 1H), 3.00-3.1 (m, 1H), 3.2-3.3 (m, 2H), 3.25 (s, 3H), 3.5 (s, 3H), 4.3 (d, J=14 Hz, 1H), 4.6 (d, J=14 Hz, 1H), 5.5 (m, 1H), 6.9 (d, J=7.84 Hz, 1H), 7.3 (dd, J=8.1 and J=7 Hz, 1H), 7.4 (d, J=7 Hz, 1H), 7.55 (dd, J=8.1 and J=7 Hz, 1H), 7.6 (d, J=8 Hz, 1H), 7.9 (d, J=8 Hz, 1H), 8 (s, 1H).

Example 4

Synthesis of 30-cyclohexyl-12,21-dimethyl-4-oxa-20-thia-1,12,19,21,24-pentaazapentacyclo [22.2.2.1$^{11,14}$.1$^{13,17}$.0$^{5,10}$]triaconta-5,7,9,11(30),13 (29),14,16-heptaene-2,18-dione 20,20-dioxide 22

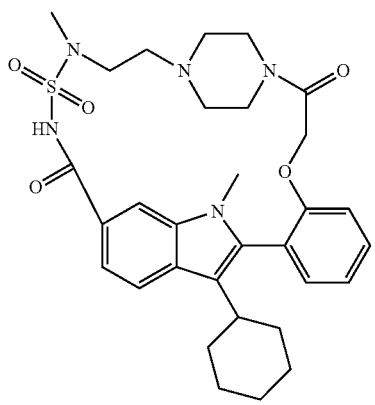

The synthesis of the title compound 22 was performed following the 5-step procedure reported for the synthesis of compound 21, using N-methyl-2-nitro-N-(2-(piperazin-1-yl) ethyl)benzenesulfonamide instead of N-(5-aminopentyl)-N-methyl-2-nitrobenzenesulfonamide 16 in the first step, and yielded 33 mg of a white solid; m/z 594 [M+H]$^+$.

$^1$H NMR (400 MHz, CDCl$_3$) δ ppm 0.5-0.8 (m, 1H), 1.1-1.3 (m, 8H), 1.5-1.8 (m, 7H), 2.05-2.1 (m, 1H), 2.45-2.5 (m, 2H), 2.6-2.65 (m, 1H), 2.75-3.00 (m, 2H), 2.95 (s, 3H), 3.47 (s, 3H), 3.48-3.5 (m, 1H), 3.95-4.00 (m, 1H), 4.4 (d, J=14 Hz, 1H), 4.75 (d, J=14 Hz, 1H), 7.05 (d, J=8.3 Hz, 1H), 7.2 (dd, J=7.4 and J=7.3 Hz, 1H), 7.4 (d, J=7.3 Hz, 1H), 7.5 (dd, J=8.3 and J=7.4 Hz, 1H), 7.6 (d, J=8.4 Hz, 1H), 7.85 (d, J=8.4 Hz, 1H), 7.95 (s, 1H).

Example 5

Synthesis of 24-cyclohexyl-9,18-dimethyl-4,5,6,7,8,9-hexahydro-13,17:16,19-di(metheno)-1,10,4,9,11,18-benzoxathiatetraazacyclohenicosine-3,12(2H,11H,18H)-dione 10,10-dioxide 32

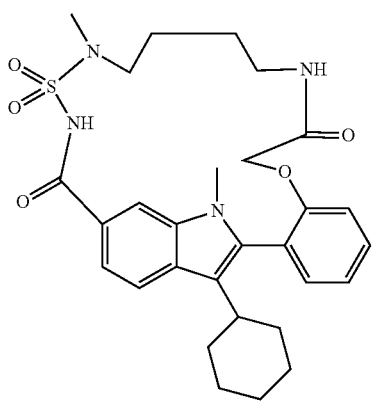

Step 1

Starting material synthesis (2-bromo-3-cyclohexyl-6-tert-butylester indole) 23 is described in US2007270406A1

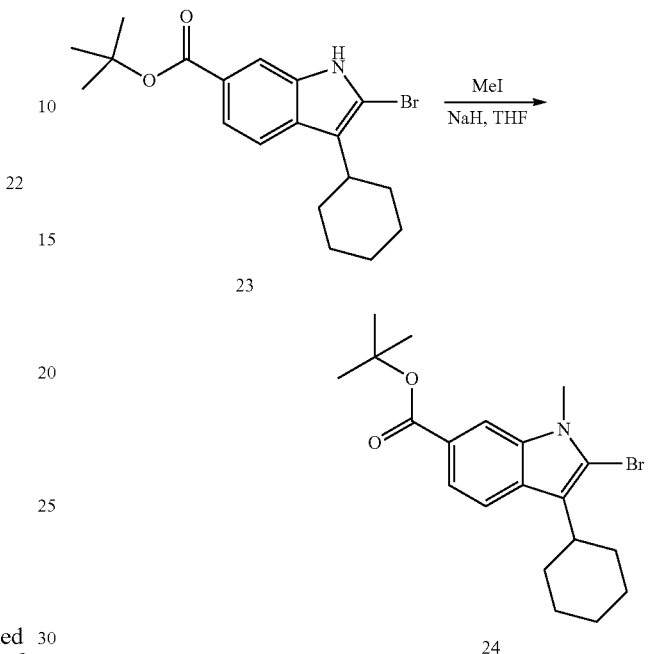

NaH (400 mg, 15.86 mmol) was added to a solution of intermediate 23 (4 g, 10.57 mmol) in dry THF. Then, iodomethane (3 g, 21.15 mmol) was added at room temperature. After 12 h, the reaction mixture was partitioned between water (pH 6) and AcOEt. Organic layer was dried over anhydrous Na$_2$SO$_4$, filtered and then evaporated. The residue was purified by silica column chromatography (gradient heptane/ EtOAc 1:0 to 80:20) to yield 3.8 g (92%) of tert-butyl 2-bromo-3-cyclohexyl-1-methyl-1H-indole-6-carboxylate 24: m/z=393 (M+H)$^+$.

Step 2

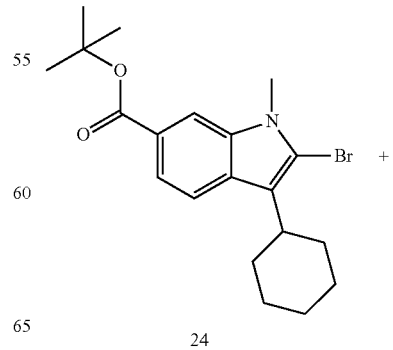

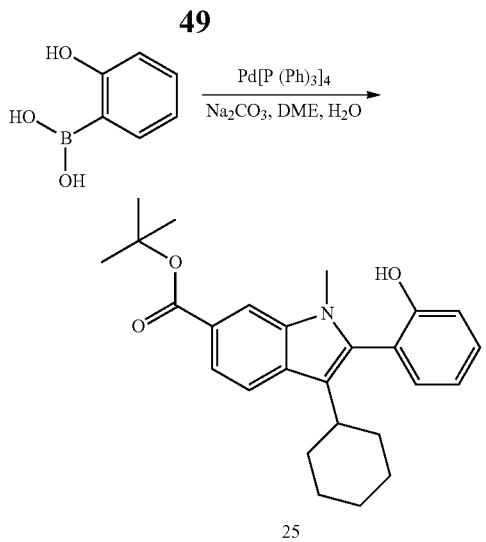

A solution of tert-butyl 2-bromo-3-cyclohexyl-1-methyl-1H-indole-6-carboxylate (24, 500 mg, 1.27 mmol), 2-hydroxy-phenylboronic acid (211 mg, 1.53 mmol) and potassium carbonate (1.35 g, 12.74 mmol) in 100 mL of 1,2-dimethoxyethane/water (4:1) was thoroughly flushed with argon. Then trans-bis(triphenylphosphine)palladium(II) chloride (0.147 g, 0.127 mmol) was added and the reaction was heated at 100° C. under argon for 12 h. The reaction mixture was cooled to room temperature, diluted with water and extracted with ethylacetate (EtOAc). Combined organic layers were washed with a saturated solution of NaHCO$_3$ and brine, dried over anhydrous Na$_2$SO$_4$ and filtered. The filtered solution was concentrated under vacuum to give tert-butyl 3-cyclohexyl-2-(2-hydroxyphenyl)-1-methyl-1H-indole-6-carboxylate 25: m/z=406 (M+H)$^+$.

Step 3

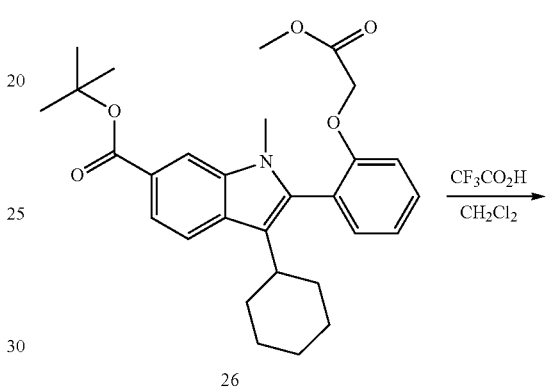

A solution of intermediate 25 (0.6 g, 1.5 mmol), methyl 2-bromoacetate (0.281 g, 1.83 mmol) and potassium carbonate (0.423 g, 3.06 mmol) in MeCN 50 mL was stirred at room temperature. After 12 h, the reaction mixture was concentrated under vacuum and the residue was partitioned between CH$_2$Cl$_2$ and water. The organic layer was dried and evaporated under vacuum to yield 0.7 g (96%) of tert-butyl 3-cyclohexyl-2-[2-(2-methoxy-2-oxoethoxy)phenyl]-1-methyl-1H-indole-6-carboxylate 26: m/z=478 (M+H)$^+$.

Step 4

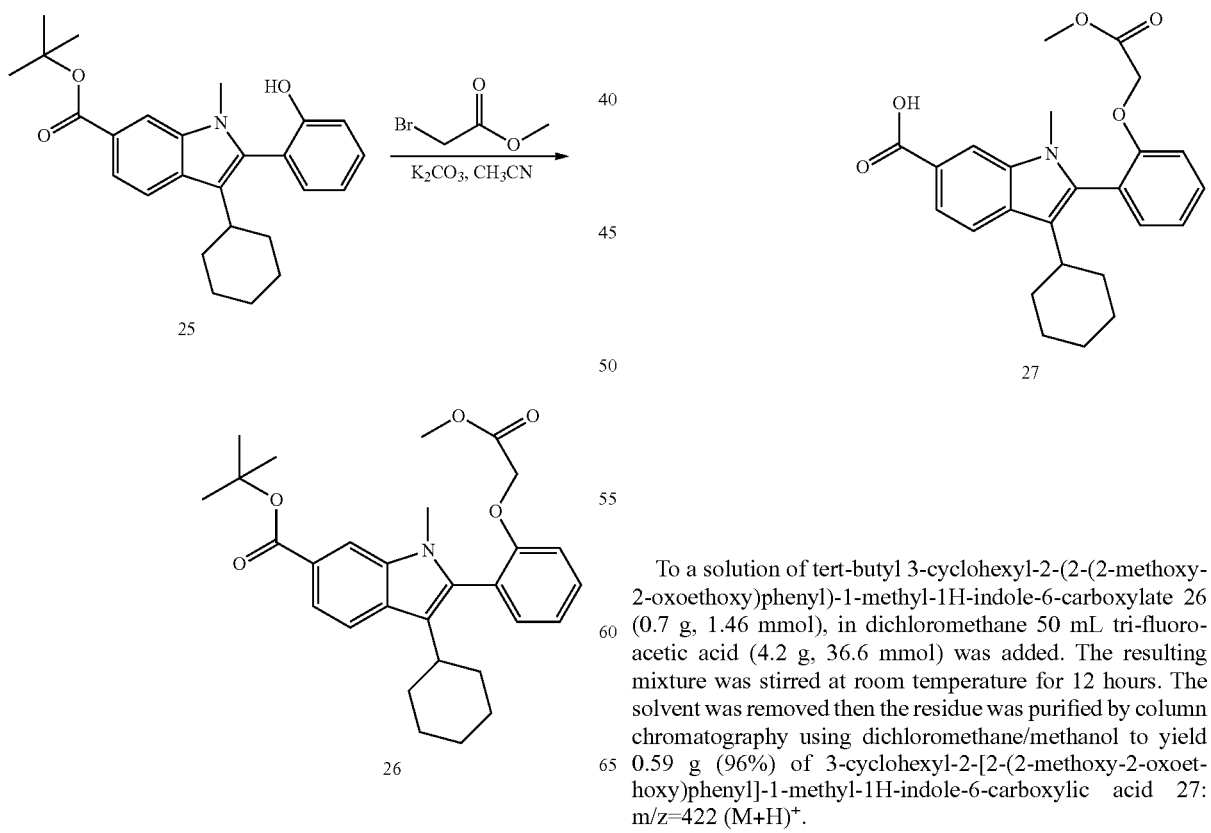

To a solution of tert-butyl 3-cyclohexyl-2-(2-(2-methoxy-2-oxoethoxy)phenyl)-1-methyl-1H-indole-6-carboxylate 26 (0.7 g, 1.46 mmol), in dichloromethane 50 mL tri-fluoroacetic acid (4.2 g, 36.6 mmol) was added. The resulting mixture was stirred at room temperature for 12 hours. The solvent was removed then the residue was purified by column chromatography using dichloromethane/methanol to yield 0.59 g (96%) of 3-cyclohexyl-2-[2-(2-methoxy-2-oxoethoxy)phenyl]-1-methyl-1H-indole-6-carboxylic acid 27: m/z=422 (M+H)$^+$.

Step 5

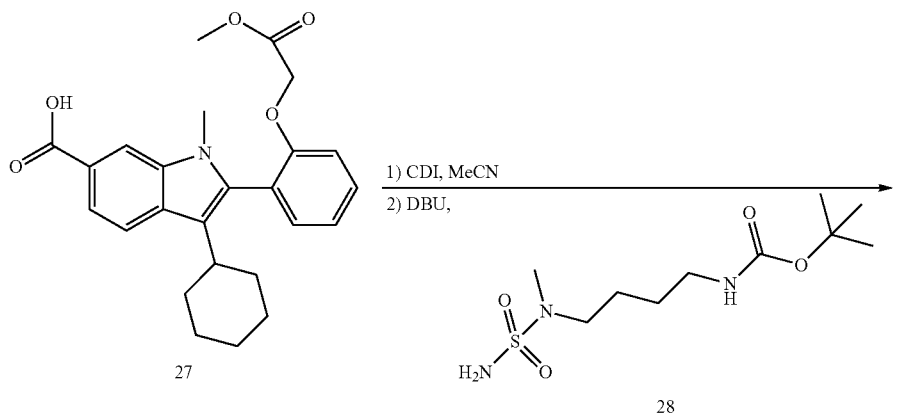

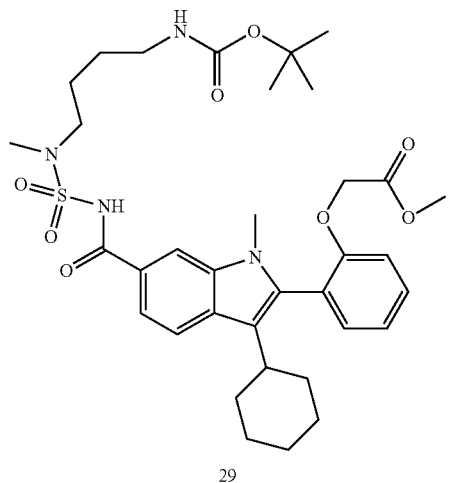

Carbonyldiimidazole (567 mg, 3.5 mmol) was added to a stirred solution of intermediate 27 (590 mg, 1.4 mmol) in dry acetonitrile (CH₃CN) (30 mL). The reaction mixture was stirred at room temperature for 2 h, upon which complete conversion was observed. The tent-butyl 4-(methyl(sulfamoyl)amino)butylcarbamate 28 (394 mg, 1.4 mmol) and DBU (426 mg, 2.8 mmol) was added. The reaction mixture was stirred overnight at room temperature. The solvent was then removed under vacuum, and the resulting residue was successively dissolved in dichloromethane, washed with a solution of 2M HCl two times, then brine. The resulting organic layer was dried over sodium sulfate and concentrated. The residue was purified by column chromatography using a gradient of ethylacetate in dichloromethane to yield 675 mg (70%) of the title methyl [2-(6-{[{4-[(tert-butoxycarbonyl)amino]butyl}(methyl)sulfamoyl]carbamoyl}-3-cyclohexyl-1-methyl-1H-indol-2-yl)phenoxy]acetate 29 as a white powder; m/z=685 (M+H)⁺.

Step 6

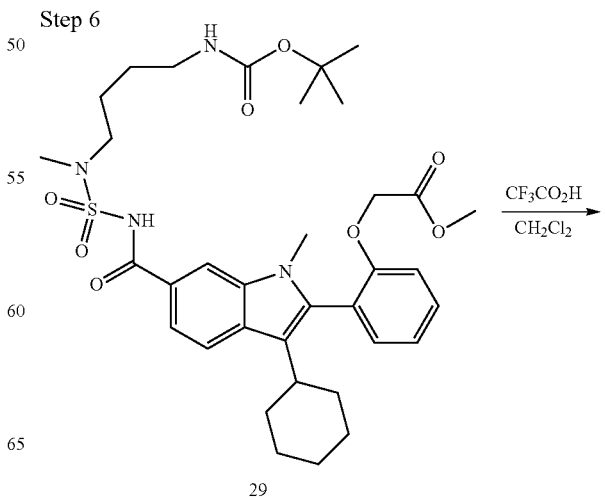

53

-continued

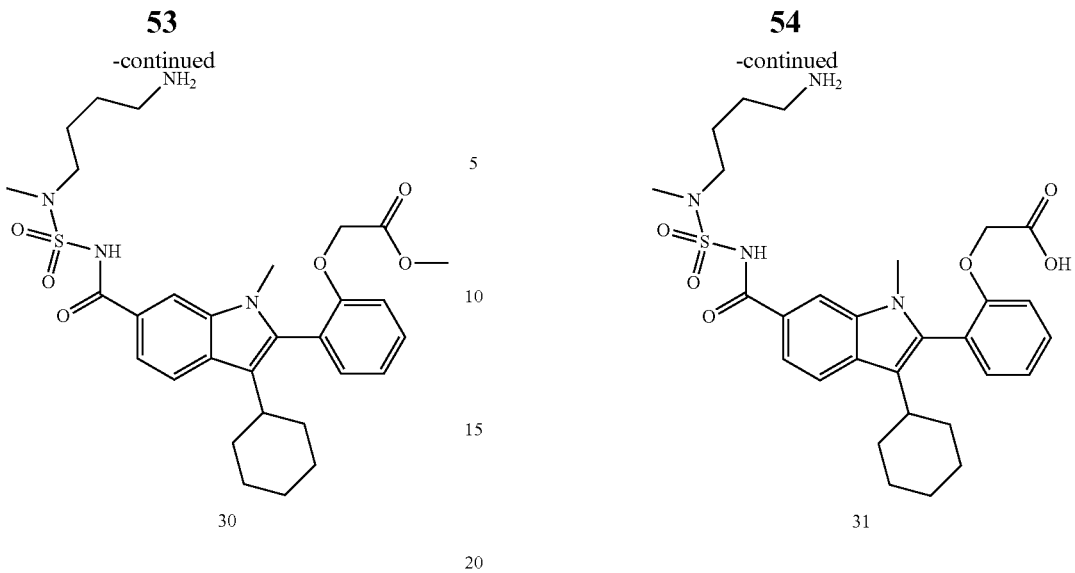

30

To a solution of intermediate 29 (0.675 g, 1 mmol), in dichloromethane 50 mL tri-fluoro-acetic acid (2.86 g, 20 mmol) was added. The resulting mixture was stirred at room temperature for 12 hours. The solvent was removed then the residue was purified by column chromatography using dichloromethane/methanol to yield 0.55 g (95%) of methyl [2-(6-{[(4-aminobutyl)(methyl)sulfamoyl]carbamoyl}-3-cyclohexyl-1-methyl-1H-indol-2-yl)phenoxy]acetate 30: m/z=585 (M+H)⁺.

Step 7

54

-continued

31

To a solution of intermediate 30 (550 mg, 0.941 mmol) in THF and methanol (4/1) (50 mL) was added a solution of lithium hydroxide (79 mg, 1.88 mmol) in water. The resulting mixture was stirred at RT for night. The mixture was then successively poured in water, acidified until pH=5 with HCl, extracted with dichloromethane, dried over MgSO₄ and concentrated. The residue was purified by column chromatography using a gradient of methanol in DCM to give 500 mg (93%) of the title product [2-(6-{[(4-aminobutyl)(methyl)sulfamoyl]carbamoyl}-3-cyclohexyl-1-methyl-1H-indol-2-yl)phenoxy]acetic acid 31 as a white solid; m/z=571 (M+H)⁺.

Step 8

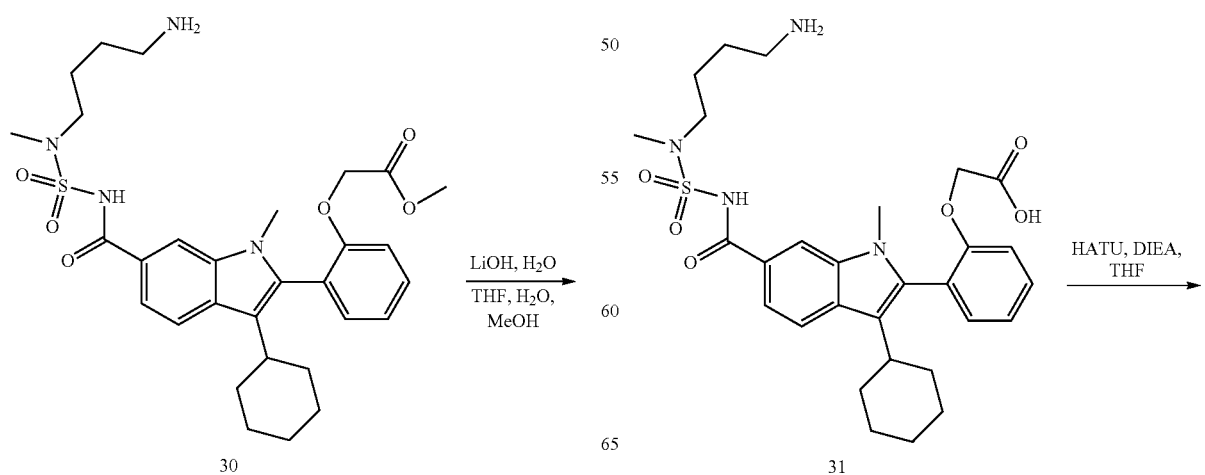

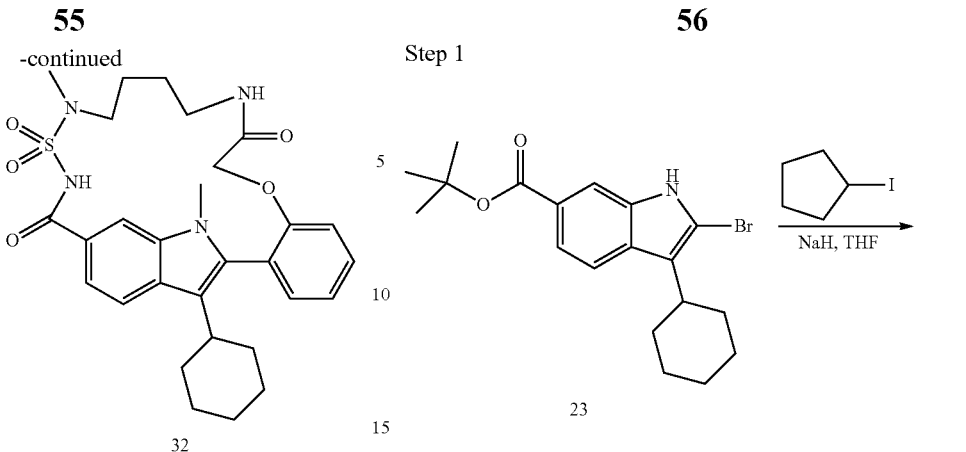

To a solution of 2-(2-(6-(N-(4-aminobutyl)-N-methylsulfamoylcarbaoyl)-3-cyclohexyl-1-methyl-1H-indol-2-yl)phenoxy)acetic acid 31 (40 mg, 0.07 mmol) in THF 50 mL, HATU (40 mg, 0.1 mmol) and diisopropylethylamine (27 mg, 02 mmol) were added. The resulting mixture was stirred at room temperature for night. Then, the reaction mixture was successively poured in water, extracted with dichloromethane, dried over MgSO₄ and concentrated. The resulting residue was purified by flash chromatography using a gradient of methanol in DCM as eluent, to give 5 mg (13% yield) of the title product 24-cyclohexyl-9,18-dimethyl-4,5,6,7,8,9-hexahydro-13,17:16,19-di(metheno)-1,10,4,9,11,18-benzoxathiatetraazacyclohenicosine-3,12(2H,11H,18H)-dione 10,10-dioxide 32; m/z=553 (M+H)⁺.

¹H NMR (400 MHz, CDCl₃) δ ppm 0.85-0.9 (m, 1H), 1.00-1.40 (m, 7H), 1.4-1.5 (m, 2H), 1.75-1.85 (m, 5H), 2.2-2.25 (m, 1H), 2.5-2.6 (m, 1H), 3.00-3.1 (m, 1H), 3.2-3.3 (m, 2H), 3.25 (s, 3H), 3.5 (s, 3H), 4.3 (d, J=14 Hz, 1H), 4.6 (d, J=14 Hz, 1H), 5.5 (m, 1H), 6.9 (d, J=7.84 Hz, 1H), 7.3 (dd, J=8.1 and J=7 Hz, 1H), 7.4 (d, J=7 Hz, 1H), 7.55 (dd, J=8.1 and J=7 Hz, 1H), 7.6 (d, J=8 Hz, 1H), 7.9 (d, J=8 Hz, 1H), 8 (s, 1H).

Example 6

Synthesis of 24-cyclohexyl-18-cyclopentyl-4,9-dimethyl-4,5,6,7,8,9-hexahydro-13,17:16,19-di(metheno)-1,10,4,9,11,18-benzoxathiatetraazacyclohenicosine-3,12(2H,11H,18H)-dione 10,10-dioxide 40

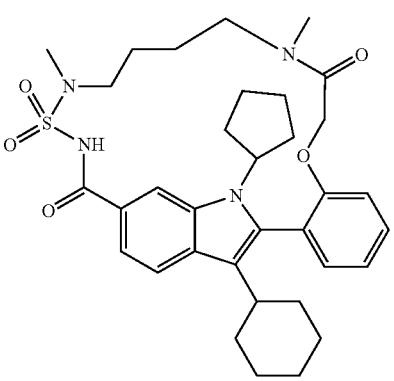

Step 1

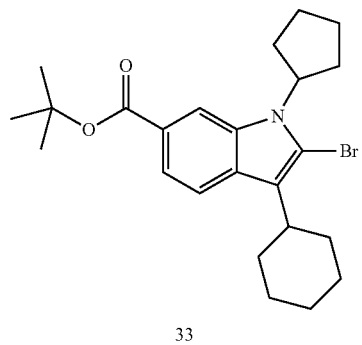

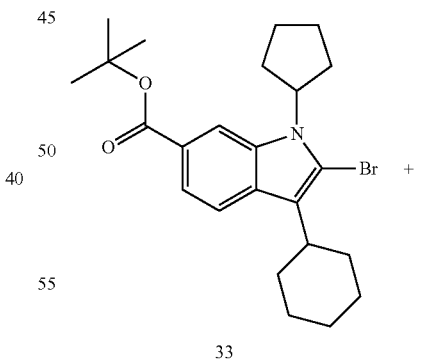

The same procedure as for the preparation of compound 24 is used for the preparation of 33 using 23 and iodocyclopentane as starting material, yielding 500 mg (15% yield) of tert-butyl 2-bromo-3-cyclohexyl-1-cyclopentyl-1H-indole-6-carboxylate 33; m/z=447 (M+H)⁺.

Step 2

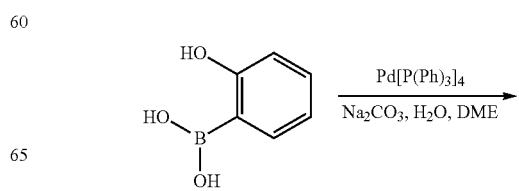

-continued

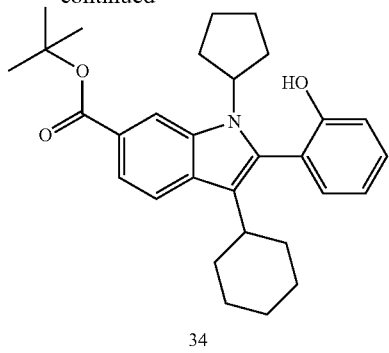

34

The same procedure as for the preparation of compound 25 is used for the preparation of 34 using intermediate 33 and 2-hydroxy-phenylboronic acid as starting material, yielding 400 mg (28% yield) of tert-butyl 3-cyclohexyl-1-cyclopentyl-2-(2-hydroxyphenyl)-1H-indole-6-carboxylate 34; m/z=460 (M+H)$^+$.

Step 3

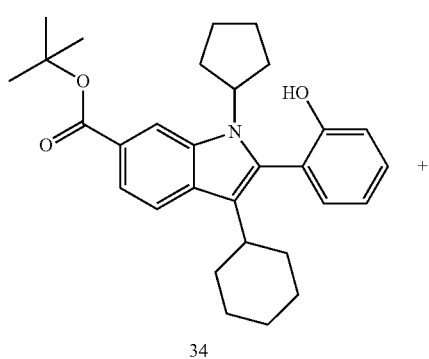

34

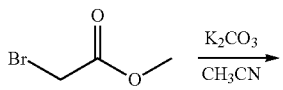

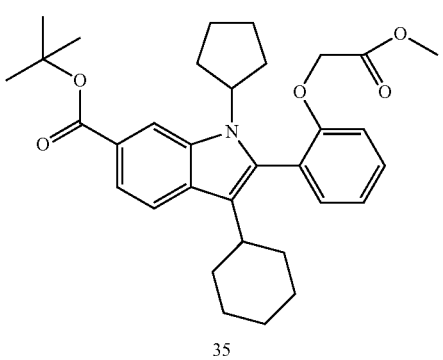

35

The same procedure as for the preparation of compound 26 is used for the preparation of 35 using intermediate 34 and methyl 2-bromoacetate as starting material, yielding 450 mg (97% yield) of tert-butyl 3-cyclohexyl-1-cyclopentyl-2-[2-(2-methoxy-2-oxoethoxy)phenyl]-1H-indole-6-carboxylate 35 was prepared; m/z=532 (M+H)$^+$ Step 4

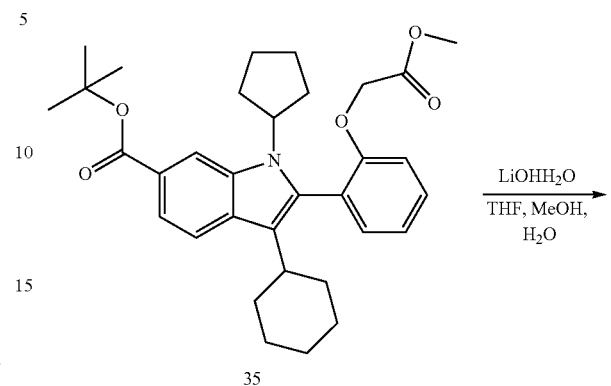

35

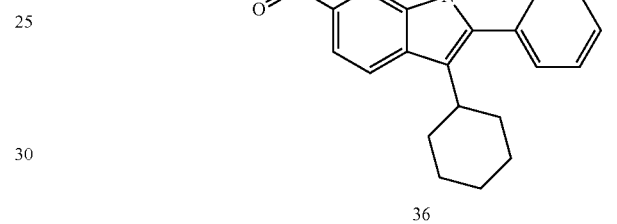

36

The same procedure as for the preparation of compound 31 is used for the preparation of 36 using intermediate 35 as starting material, yielding 410 mg (94% yield) of {2-[6-(tert-butoxycarbonyl)-3-cyclohexyl-1-cyclopentyl-1H-indol-2-yl]phenoxy}acetic acid 36; m/z=518 (M+H)$^+$ Step 5

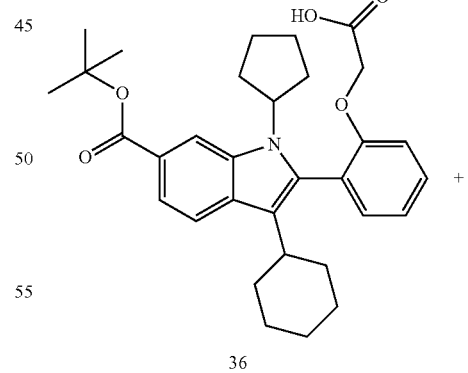

36

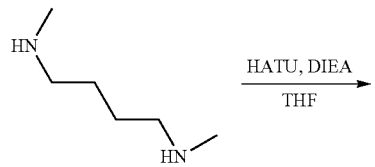

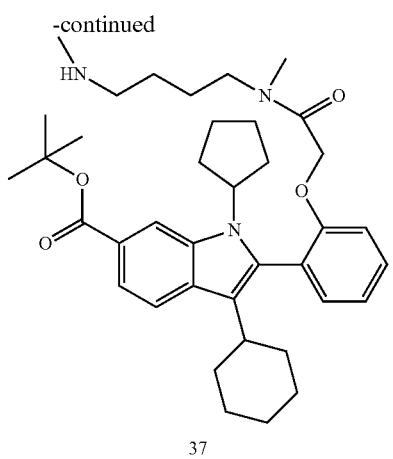

37

The same procedure as for the preparation of compound 6 is used for the preparation of 37 using intermediate 36 and N,N'-dimethylbutylene diamine as starting material, yielding 450 mg (92% yield) of tert-butyl 3-cyclohexyl-1-cyclopentyl-2-[2-(2-{methyl[4-(methylamino)butyl]amino}-2-oxoethoxy)phenyl]-1H-indole-6-carboxylate 37; m/z=617 (M+H)$^+$ Step 6

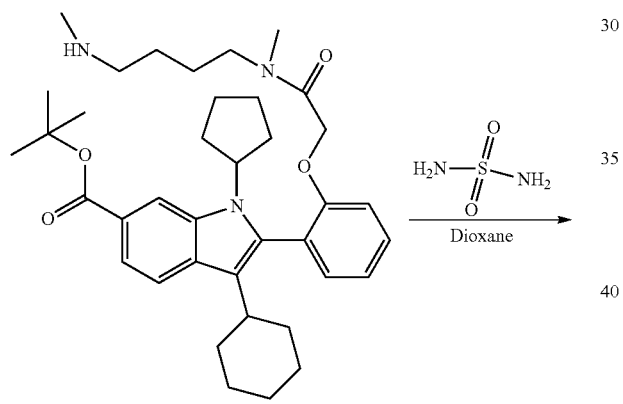

37

38

The same procedure as for the preparation of compound 19 is used for the preparation of 38 using intermediate 37 as starting material, yielding 400 mg (79% yield) of tert-butyl 3-cyclohexyl-1-cyclopentyl-2-{2-[2-(methyl{4-[methyl(sulfamoyl)amino]butyl}amino)-2-oxoethoxy]phenyl}-1H-indole-6-carboxylate 38; m/z=695 (M+H)$^+$ Step 7

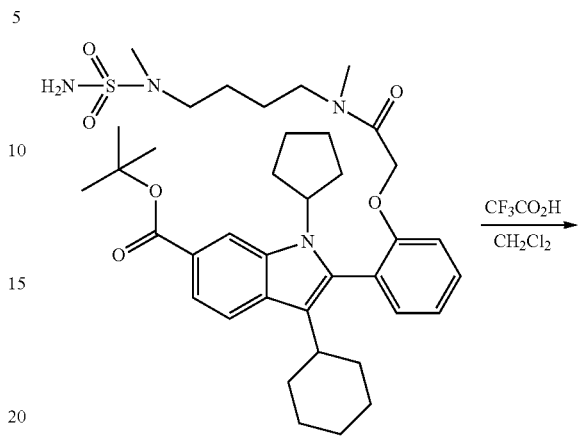

38

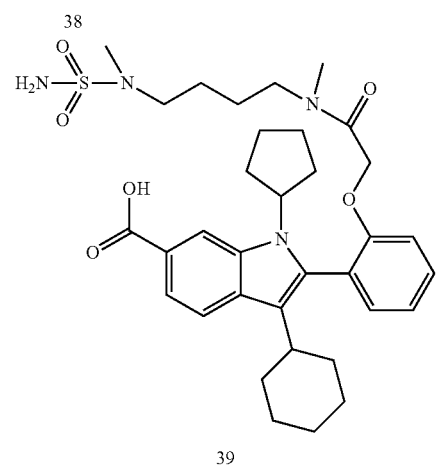

39

The same procedure as for the preparation of compound 27 is used for the preparation of 39 using intermediate 38 as starting material, yielding 150 mg (41% yield) of 3-cyclohexyl-1-cyclopentyl-2-{2-[2-(methyl{4-[methyl(sulfamoyl)amino]butyl}amino)-2-oxoethoxy]phenyl}-1H-indole-6-carboxylic acid 39; m/z=639 (M+H)$^+$ Step 8

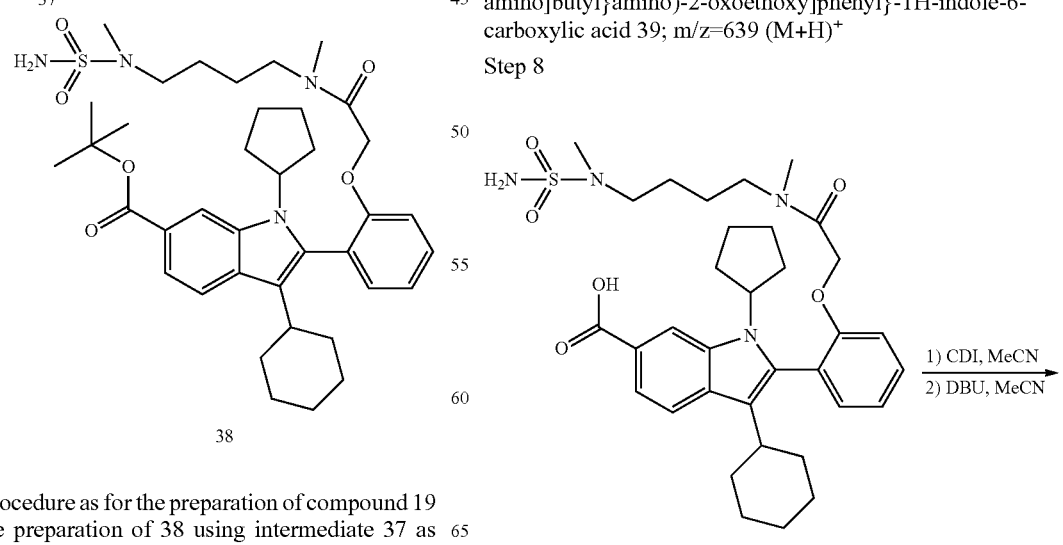

39

-continued

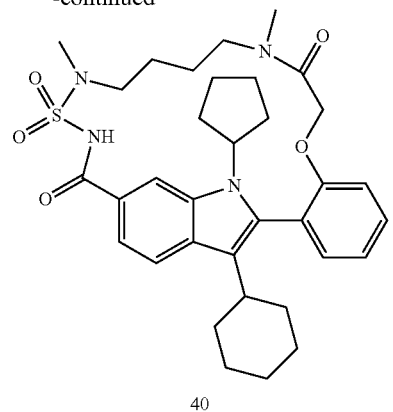

40

The same procedure as for the preparation of compound 21 is used for the preparation of 40 using intermediate 39 as starting material, yielding 30 mg (21% yield) of 24-cyclohexyl-18-cyclopentyl-4,9-dimethyl-4,5,6,7,8,9-hexahydro-13,17:16,19-di(metheno)-1,10,4,9,11,18-benzoxathiatetraazacyclohenicosine-3,12(2H,11H,18H)-dione 10,10-dioxide 40; m/z=621 (M+H)$^+$ $^1$H NMR (400 MHz, CDCl$_3$) δ ppm 0.85-0.9 (m, 1H), 1.00-1.40 (m, 7H), 1.5-1.6 (m, 5H), 1.75-1.85 (m, 6H), 2-2.3 (m, 6H), 2.35-2.5 (m, 2H), 2.6 (s, 3H), 2.9 (s, 3H), 3.25-3.35 (m, 1H), 3.9-3.95 (m, 1H), 4.2 (d, J=14 Hz, 1H), 4.4 (d, J=14 Hz, 1H), 7 (d, J=7.9 Hz, 1H), 7.25 (dd, J=8.1 and J=7 Hz, 1H), 7.4 (d, J=8.1 Hz, 1H), 7.5 (dd, J=7.9 and J=7 Hz, 1H), 7.55 (d, J=8.1 Hz, 1H), 7.85 (d, J=8.1 Hz, 1H), 7.9 (s, 1H).

Example 7

Synthesis of 25-cyclohexyl-23-fluoro-10,19-dimethyl-5,6,7,8,9,10-hexahydro-2H-14,18:17,20-di(metheno)-1,11,4,10,12,19-benzoxathiatetraazacyclodocosine-3,13(4H,12H,19H)-dione 11,11-dioxide 50

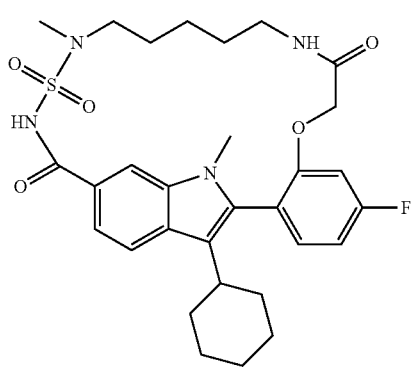

Step 1

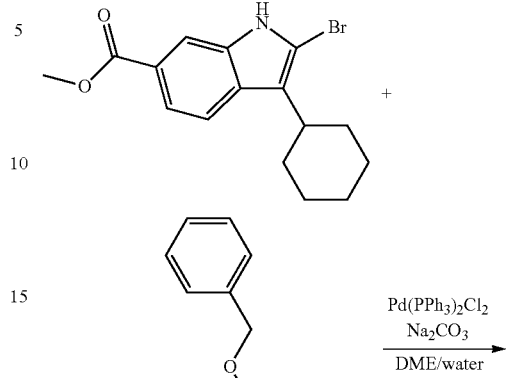

The same procedure as for the preparation of compound 25 is used for the preparation of 41 using methyl 2-bromo-3-cyclohexyl-1H-indole-6-carboxylate 1 and 2-(benzyloxy)-4-fluorophenylboronic acid as starting material, yielding 14.9 mg (87% yield) of methyl 2-[2-(benzyloxy)-4-fluorophenyl]-3-cyclohexyl-1H-indole-6-carboxylate 41; m/z=458 (M+H)$^+$ Step 2

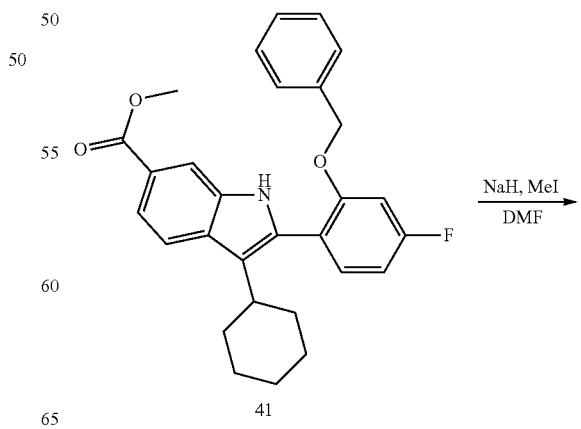

41

63
-continued

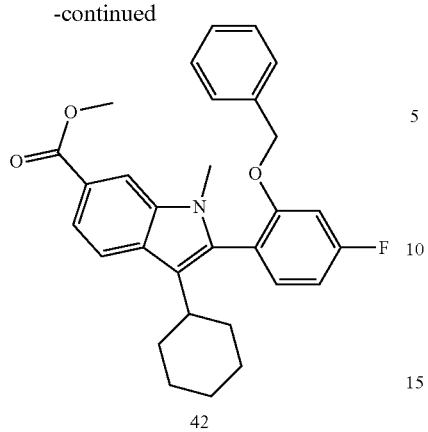

42

The same procedure as for the preparation of compound 3 is used for the preparation of 42 using intermediate 41 as starting material, to give methyl 2-[2-(benzyloxy)-4-fluorophenyl]-3-cyclohexyl-1-methyl-1H-indole-6-carboxylate 42 in quantitative yield: m/z=472 (M+H)+

Step 3

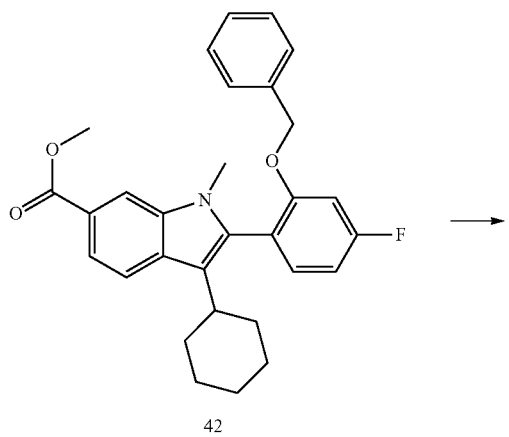

42

→

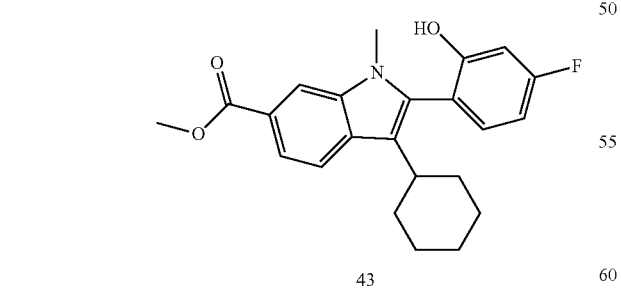

43

The same procedure as for the preparation of compound 4 is used for the preparation of 43 using intermediate 42 as starting material, to give methyl 3-cyclohexyl-2-(4-fluoro-2-hydroxyphenyl)-1-methyl-1H-indole-6-carboxylate 43 in 96% yield; m/z=382 (M+H)+

64

Step 4

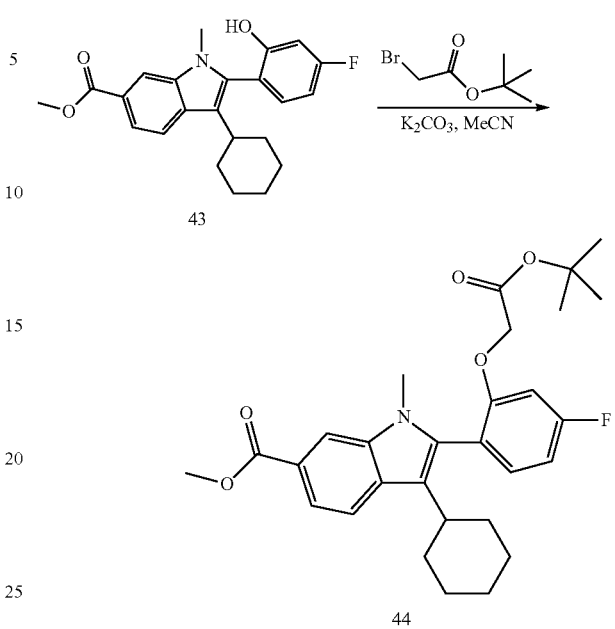

The same procedure as for the preparation of compound 26 is used for the preparation of 44 using intermediate 43 and tent-butyl 2-bromoacetate as starting material, to give methyl 2-[2-(2-tert-butoxy-2-oxoethoxy)-4-fluorophenyl]-3-cyclohexyl-1-methyl-1H-indole-6-carboxylate 44 in quantitative yield; m/z=496 (M+H)+

Step 5

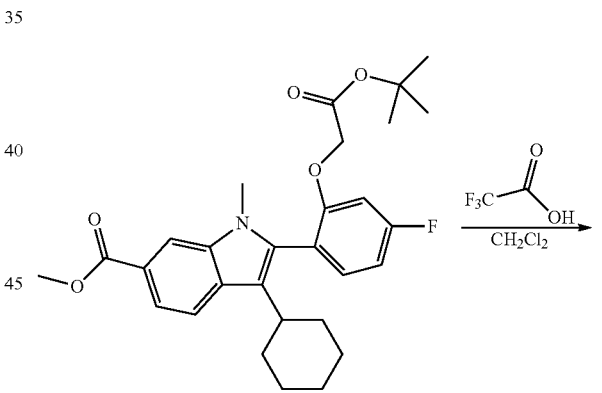

44

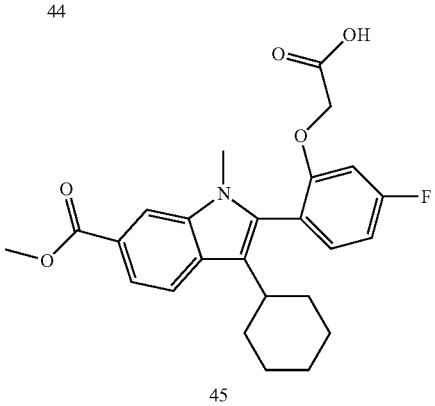

45

The same procedure as for the preparation of compound 27 is used for the preparation of 45 using intermediate 44 as starting material, to give {2-[3-cyclohexyl-6-(methoxycarbonyl)-1-methyl-1H-indol-2-yl]-5-fluorophenoxy}acetic acid 45 in quantitative yield; m/z=440 (M+H)⁺

Step 6

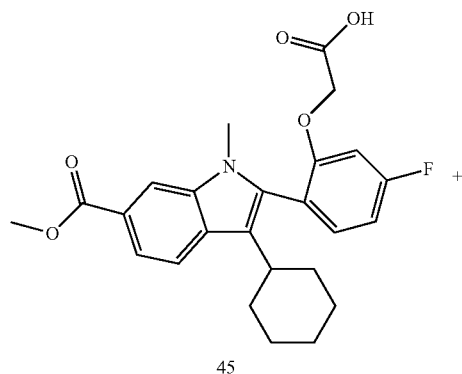

45

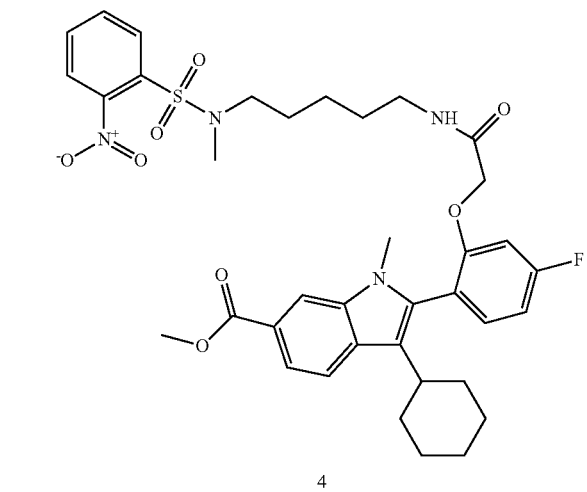

16

4

The same procedure as for the preparation of compound 17 is used for the preparation of 46 using intermediate 45 and N-(5-aminopentyl)-N-methyl-2-nitrobenzenesulfonamide 16 as starting material, yielding 891 mg (68% yield) of methyl 3-cyclohexyl-2-(4-fluoro-2-{2-[(5-{methyl[(2-nitrophenyl)sulfonyl]amino}pentyl)amino]-2-oxoethoxy}phenyl)-1-methyl-1H-indole-6-carboxylate 46; m/z=723 (M+H)⁺

Step 7

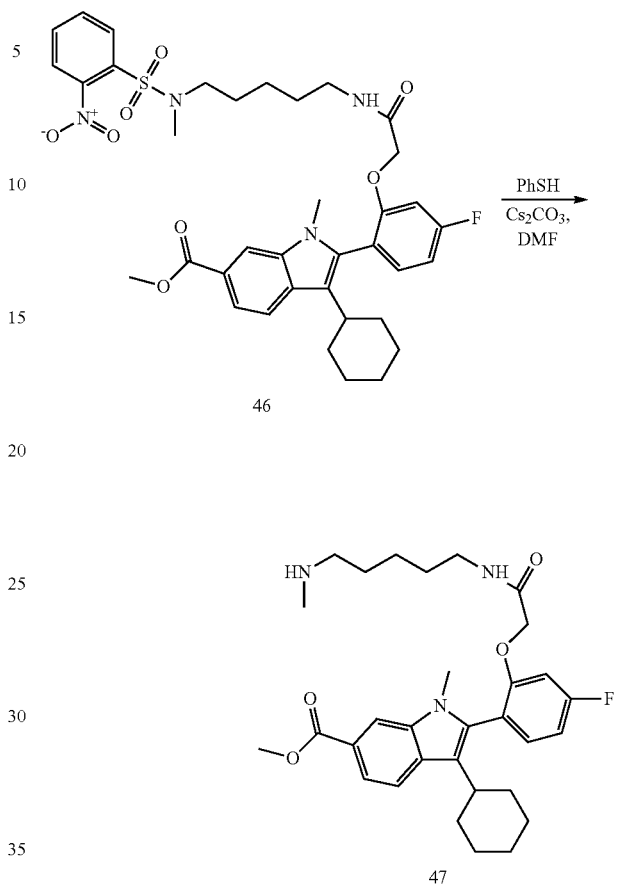

46

47

The same procedure as for the preparation of compound 18 is used for the preparation of 47 using intermediate 46 as starting material, to yield 520 mg (78% yield) of methyl 3-cyclohexyl-2-[4-fluoro-2-(2-{[5-(methylamino)pentyl]amino}-2-oxoethoxy)phenyl]-1-methyl-1H-indole-6-carboxylate 47; m/z=538 (M+H)⁺

Step 8

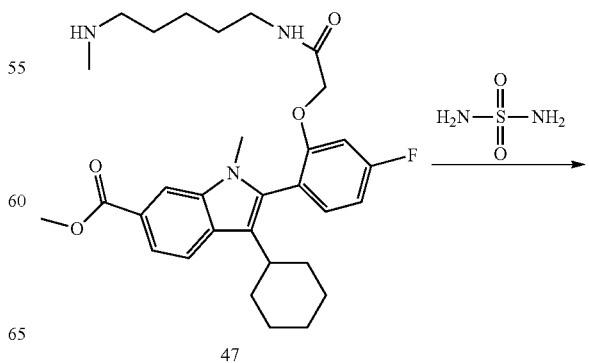

47

-continued

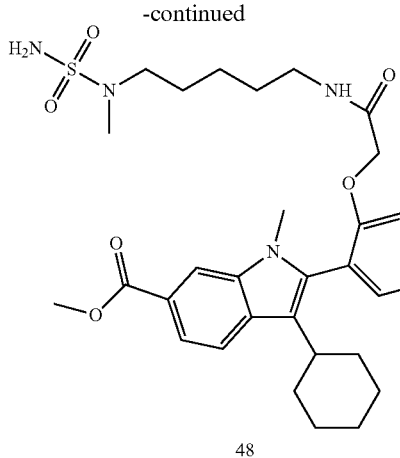

48

The same procedure as for the preparation of compound 19 is used for the preparation of 48 using intermediate 47 as starting material, to yield 590 mg (98% yield) of methyl 3-cyclohexyl-2-{4-fluoro-2-[2-({5-[methyl(sulfamoyl) amino]pentyl}amino)-2-oxoethoxy]phenyl}-1-methyl-1H-indole-6-carboxylate 48; m/z=617 (M+H)+ Step 9

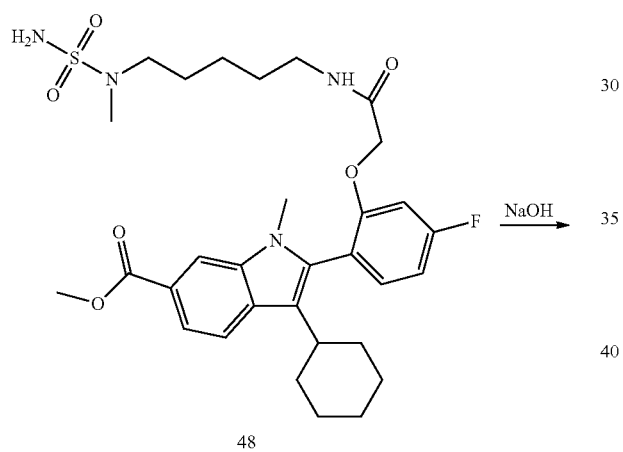

48

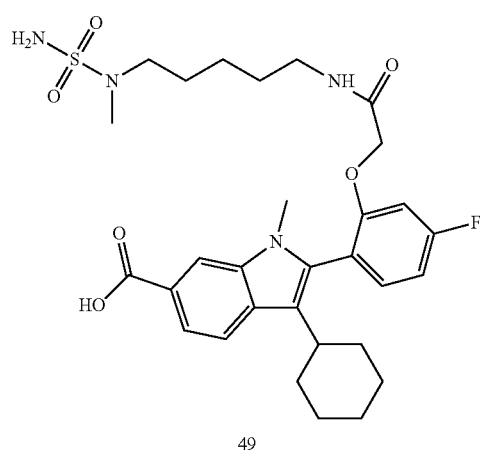

49

The same procedure as for the preparation of compound 8 is used for the preparation of 49 using intermediate 48 as starting material, to yield 399 mg (67% yield) of 3-cyclohexyl-2-{4-fluoro-2-[2-({5-[methyl(sulfamoyl)amino] pentyl}amino)-2-oxoethoxy]phenyl}-1-methyl-1H-indole-6-carboxylic acid 49; m/z=603 (M+H)+

Step 10

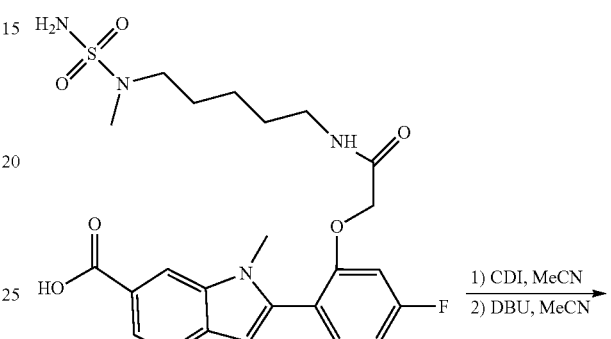

49

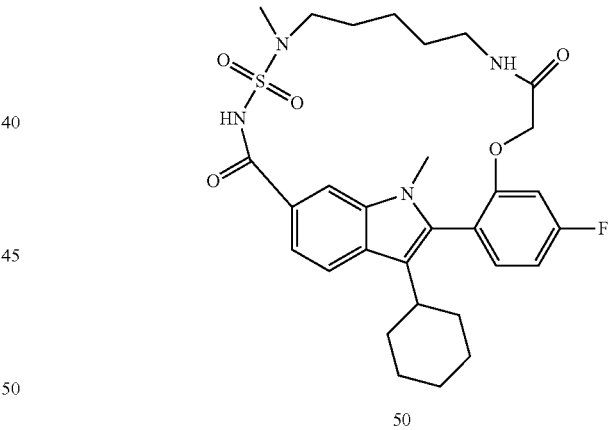

50

The same procedure as for the preparation of compound 21 is used for the preparation of 50 using intermediate 49 as starting material, to yield 220 mg (57% yield) of 25-cyclohexyl-23-fluoro-10,19-dimethyl-5,6,7,8,9,10-hexahydro-2H-14,18:17,20-di(metheno)-1,11,4,10,12,19-benzoxathiatetraazacyclodocosine-3,13(4H,12H,19H)-dione 11,11-dioxide 50; m/z=585 (M+H)+

¹H NMR (400 MHz, DMSO-d₆) δ ppm 0.55-0.65 (m, 1H), 1.00-1.10 (m, 2H), 1.12-1.27 (m, 5H), 1.52-1.58 (m, 2H), 1.64-1.78 (m, 6H), 2.25-2.29 (m, 1H), 2.95-3.05 (m, 5H), 3.28-3.38 (m, 2H), 3.47 (s, 3H), 4.40 (d, J=13.5 Hz, 1H), 4.49 (d, J=13.7 Hz, 1H), 5.88 (t, J=5.2 Hz, 1H), 7.03-7.08 (m, 1H), 7.18 (d, J=10.5 Hz, 1H), 7.42-7.47 (m, 1H), 7.62 (d, J=8.5 Hz, 1H), 7.84 (d, J=8.4 Hz, 1H), 8.39 (s, 1H), 11.62 (s, 1H).

Example 8

Synthesis of 25-cyclohexyl-22-fluoro-10,19-dimethyl-5,6,7,8,9,10-hexahydro-2H-14,18:17,20-di(metheno)-1,11,4,10,12,19-benzoxathiatetraazacyclodocosine-3,13(4H,12H,19H)-dione 11,11-dioxide 51

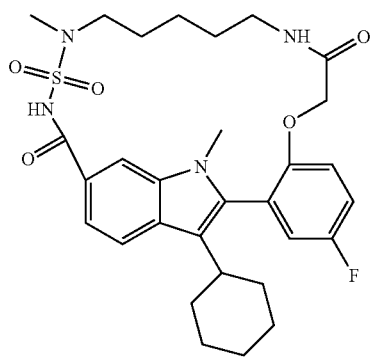

The synthesis of the title compound 51 was performed following the 10-step procedure reported for the synthesis of compound 50, using 2-(benzyloxy)-5-fluorophenylboronic acid in the first step, and yielded 431 mg of a white solid; m/z 585 [M+H]$^+$.

$^1$H NMR (400 MHz, CHCl$_3$-d$_6$) δ ppm 0.64-0.72 (m, 1H), 0.96-1.01 (m, 2H), 1.09-1.13 (m, 1H), 1.18-1.32 (m, 3H), 1.40-1.47 (m, 1H), 1.59 (br s, 4H), 1.70-1.85 (m, 6H), 2.15-2.22 (m, 1H), 2.52-2.65 (m, 1H), 3.05-3.09 (m, 1H), 3.22 (s, 3H), 3.24-3.31 (m, 1H), 3.53 (s, 3H), 4.33 (d, J=12.5 Hz, 1H), 4.41 (d, J=14 Hz, 1H), 5.36-5.40 (m, 1H), 6.94 (dd, J=8.1 and J=3.4 Hz, 1H), 7.14 (d, J=7.8 Hz, 1H), 7.22 (d, J=7.6 Hz, 1H), 7.56 (d, J=8.3 Hz, 1H), 7.91 (d, J=8.3 Hz, 1H), 7.99 (s, 1H), 8.93 (br s, 1H).

Example 9

Synthesis of 25-cyclohexyl-4,10-dimethyl-19-(1-methylethyl)-5,6,9,10-tetrahydro-2H,8H-14,18:17,20-di(metheno)-1,7,11,4,10,12,19-benzodioxathiatetraazacyclodocosine-3,13 (4H,12H,19H)-dione 11,11-dioxide 52

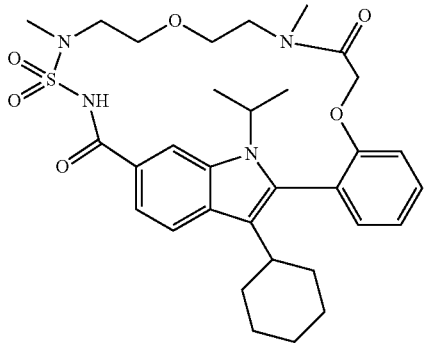

The synthesis of the title compound 52 was performed following the 8-step procedure reported for the synthesis of compound 40, using 2-iodopropane in the first step and N-methyl-2-(methylaminoethyloxy)ethylamine in step 5, yielded 300 mg of a white solid; m/z 611 [M+H]$^+$.

$^1$H NMR (400 MHz, CDCl$_3$) δ ppm 1.1-1.2 (m, 4H), 16-1.75 (m, 11H), 2.2 (s, 3H), 2.25-2.3 (m, 2H), 2.4-2.5 (m, 1H), 3.00-3.1 (m, 2H), 3.2 (s, 3H), 3.3-3.35 (m, 1H), 3.4-3.48 (m, 2H), 3.5-3.55 (m, 1H), 4.1-4.25 (m, 2H), 4.35-4.5 (m, 2H), 6.88 (d, J=8.1 Hz, 1H), 7.25 (dd, J=8.2 and J=7.5 Hz, 1H), 7.35-7.4 (m, 2H), 7.5 (dd, J=8.1 and J=7.5 Hz, 1H), 7.8 (d, J=8.3 Hz, 1H), 8.12 (s, 1H), 8.5 (br.s, 1H).

Example 10

Synthesis of 24-cyclohexyl-22-methoxy-4,9,18-trimethyl-4,5,6,7,8,9-hexahydro-13,17:16,19-di(metheno)-1,10,4,9,11,18-benzoxathiatetraazacyclohenicosine-3,12(2H,11H,18H)-dione 10,10-dioxide 53

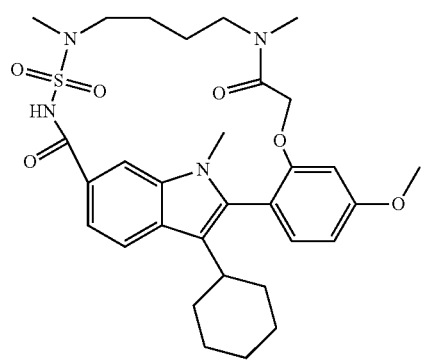

The synthesis of the title compound 53 was performed following the 9-step procedure reported for the synthesis of compound 10, using 2-(benzyloxy)-4-methoxyphenylboronic acid in the first step and N,N'-dimethylbutylene diamine in step 5, yielding 57 mg of a white solid; m/z 597 [M+H]$^+$.

$^1$H NMR (400 MHz, CHCl$_3$-d$_6$) δ ppm 1.04-1.08 (m, 1H), 1.20-1.36 (m, 4H), 1.37-1.46 (m, 4H), 1.69 (s, 3H), 1.73-1.76 (m, 2H), 1.78-1.98 (m, 4H), 2.06-2.15 (m, 1H), 2.65-2.71 (m, 1H), 3.12 (s, 3H), 3.25-3.30 (m, 1H), 3.58 (s, 3H), 3.72 (d, J=13.1 Hz, 1H), 3.87 (s, 3H), 3.92-4.01 (m, 1H), 4.07 (d, J=13.1 Hz, 1H), 6.76 (d, J=2.1 Hz, 1H), 6.80 (dd, J=8.5 and 2.4 Hz, 1H), 7.32 (d, J=8.3 Hz, 1H), 7.58 (d, J=8.7 Hz, 1H), 7.72 (s, 1H), 7.85 (d, J=8.5 Hz, 1H), 8.36 (br s, 1H).

Example 11

Synthesis of 25-cyclohexyl-23-methoxy-4,10,19-trimethyl-5,6,9,10-tetrahydro-2H,8H-14,18:17,20-di(metheno)-1,7,11,4,10,12,19-benzodioxathiatetraazacyclodocosine-3,13 (4H,12H,19H)-dione 11,11-dioxide 54

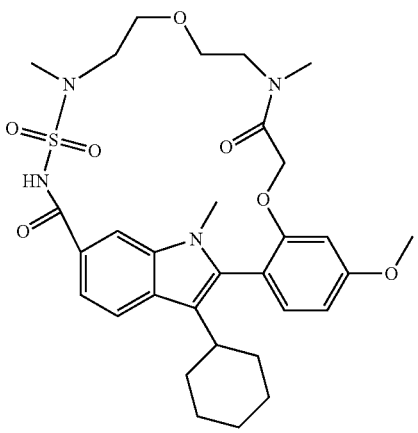

54

The synthesis of the title compound 54 was performed following the 9-step procedure reported for the synthesis of compound 10, using 2-(benzyloxy)-4-methoxyphenylboronic acid in the first step, yielded 9 mg of a white solid; m/z 613 [M+H]$^+$.

$^1$H NMR (400 MHz, CHCl$_3$-d$_6$) δ ppm 1.15-1.38 (m, 4H), 1.70-1.75 (m, 2H), 1.78-1.90 (m, 4H), 2.17 (s, 3H), 2.30-2.38 (m, 1H), 2.45-2.51 (m, 1H), 2.52-2.63 (m, 1H), 3.02-3.09 (m, 1H), 3.22 (s, 3H), 3.26-3.33 (m, 1H), 3.47 (s, 3H), 3.52-3.56 (m, 2H), 3.70-3.78 (m, 1H), 3.90 (s, 3H), 4.07-4.15 (m, 1H), 4.41 (s, 2H), 6.51 (d, J=2.1 Hz, 1H), 6.72 (dd, J=8.2 and J=2.2 Hz, 1H), 7.31 (d, J=8.3 Hz, 1H), 7.45 (d, J=8.0 Hz, 1H), 7.74 (s, 1H), 7.82 (d, J=8.3 Hz, 1H), 8.75 (br s, 1H).

Example 12

Synthesis of N-(5-aminopentyl)-N-methyl-2-nitrobenzenesulfonamide 16

Step 1

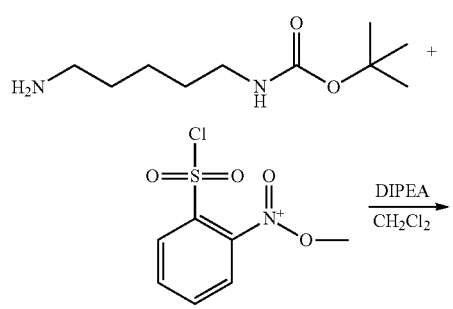

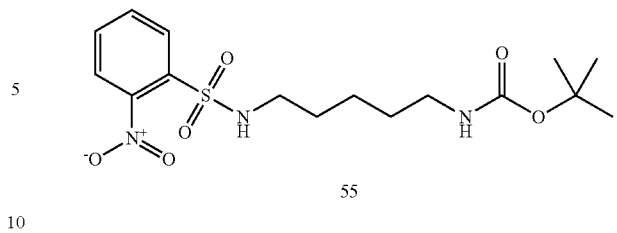

55

To a cooled solution of tent-butyl (5-aminopentyl)carbamate (20 g, 99 mmol) in dichloromethane 250 mL 2-nitrobenzene-1-sulfonyl chloride (23 g, 104 mmol) was added. The resulting mixture was stirred at 0° C. then diisopropylethylamine (19.7 g, 144 mmol) was added drop wise. The resulting mixture was stirred at room temperature overnight. The reaction mixture was poured in water and citric acid the organic layer was separated and successively dried over MgSO$_4$ filtered and concentrated to yield 32.6 g (85%) of tent-butyl (5-{[(2-nitrophenyl)sulfonyl]amino}pentyl)carbamate 55 as white needles m/z 388 [M+H]$^+$.

Step 2

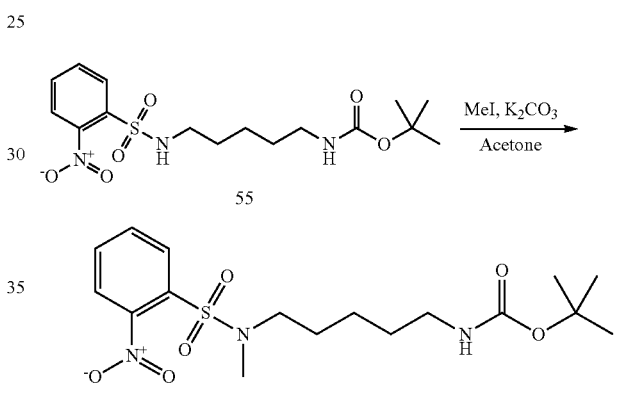

To a solution of tent-butyl (5-{[(2-nitrophenyl)sulfonyl]amino}pentyl)carbamate 55 (32.6 g, 84 mmol) in acetone (300 mL) was added potassium carbonate (23.2 g, 168 mmol). The resulting mixture was stirred at room temperature for 30 minutes then methyl iodide (17.88 g, 126 mmol) was added drop wise. The resulting mixture was stirred at room temperature overnight. The reaction mixture was poured in water and dichloromethane was added. The organic layer was separated and successively dried over MgSO$_4$ filtered and concentrated. The residue was triturated with di-isopropyl ether to yield 31.6 g 93% of tent-butyl (5-{methyl[(2-nitrophenyl)sulfonyl]amino}pentyl)carbamate 56 as a white powder m/z 402 [M+H]$^+$.

Step 3

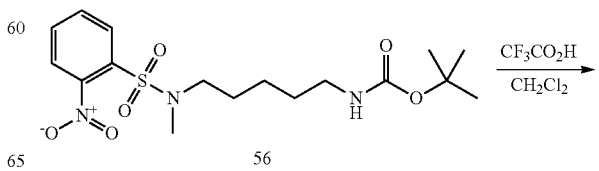

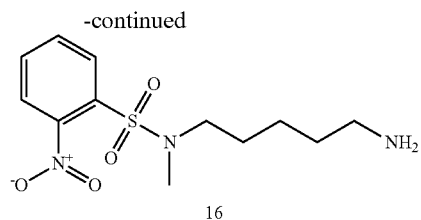

16

The same procedure as for the preparation of compound 27 is used for the preparation of 16 using intermediate 56 as starting material, to afford N-(5-aminopentyl)-N-methyl-2-nitrobenzenesulfonamide 16 in quantitative yield; m/z=302 (M+H)$^+$ Example 13

Activity of Compounds of Formula (I)

Cellular Assay

The compounds of formula (I) were examined for activity in the inhibition of HCV RNA replication in (a) cellular assay(s). The assay demonstrated that the compounds of formula (I) inhibited a HCV functional cellular replicating cell line, also known as HCV replicons. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. Two HCV cellular assays are described herein: the replicon assay (for which the result is expressed as $EC_{50}$) and the transient replicon assay (for which the result is expressed as $EC_{50}$-T).

Replicon Assay

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type Ib translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type Ib. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound was monitored on the Huh-Luc cells, enabling a dose-response curve to be generated for each test compound. $EC_{50}$ values were then calculated, which value represents the amount of the compound required to decrease by 50% the level of detected luciferase activity, or more specifically, the ability of the genetically linked HCV replicon RNA to replicate.

Transient Replicon Assay

The assay utilizes a bicistronic expression construct comprising the wild type NS3-NS5B regions of HCV type 1b (con1b) with cell culture adaptive mutations of the ET clone (E1202G, T1280I, K1846T). translated from an Internal Ribosome Entry Site (IRES) derived from encephalomyocarditis virus (EMCV), preceded by a Polio virus IRES driven reporter portion (FfL-luciferase). The construct is bordered by 5' and 3' NTRs (non-translated regions) from HCV type Ib. RNA is generated from this construct and transfected in to Huh7 cure cells (Koutsoudakis G, Herrmann E, Kallis S, Bartenschlager R, Pietschmann T. The level of CD81 cell surface expression is a key determinant for productive entry of hepatitis C virus into host cells. J. Virol. 2007; 81 (2): 588-598). The transfected HCV RNA replicates autonomously, transiently and to high levels, encoding inter alia luciferase, and are used for testing the antiviral compounds.

Design of shuttle vector. The vector cassette designed to shuttle NS5B was generated from plasmid pFKi341Luc_NS3-3'-ET (20). The replicon derived from this plasmid consists of the NS3 to 3'-UTR sequence of the HCV genotype 1b Con1 strain and carries two cell culture adaptive mutations in NS3 (E1202G and T1280I) and one in NS4B (K1846T). Two AflII restriction sites were generated with the QuickChange site-directed mutagenesis kit from Stratagene (La Jolla, Calif.) using the pFKi341Luc_NS3-3'-ET plasmid, the first into the 3' NCR directly after the stop codon of NS5B, and the second 8 amino acids upstream of the NS5A/NS5B cleavage site. Because the ScaI site necessary for linearization of the plasmid prior to in vitro transcription, was found to be present in the polymerase sequence of some clinical isolates, we mutated it to XbaI. The endogenous XbaI site of the firefly luciferase gene was removed by introduction of a silent mutation.

Construction of NS5B chimeric replicons. The cDNA encoding the C-terminus of NS5A (residues 440-447) and NS5B full length (residues 1-591) was amplified from clinical isolates using subtype-specific primers with a 5' part (16 nucleotides) complementary to the shuttle vector and a 3' part (13-19 nucleotides) designed to be complementary to clinical isolate sequences. The amplicons were cloned in the NS5B shuttle vector by using the In-Fusion cloning method (In-Fusion Dry Down PCR Cloning Kit, Clontech). Individual clones or pools of all clones obtained after transformation were used for in vitro transcription and tested in the transient replicon assay. Data were generated for compounds of the present invention using two chimeric replicons from two clinical isolates of HCV genotype 1a, 1a_H77 and 1a_6 (Genbank accession no. AF011751 and EF523592 resp.).

Transient replicon assay. Ten microgram of in vitro transcribed linear replicon RNA was transfected into Huh7-cure cells and replicon replication was quantitated after 48 h of incubation (37° C., 5% $CO_2$) by measurement of luminescence after addition of luciferase substrate (Steady Lite Plus; Perkin Elmer). Compound activity against these replicons, i.e. inhibitory activity, was measured in a nine-point dilution series enabling a dose-response curve to be generated for each test compound. $EC_{50}$ values were then calculated, which value represents the amount of the compound required to decrease by 50% the level of detected luciferase activity, or more specifically, the ability of the genetically linked HCV replicon RNA to replicate. The resulting $EC_{50}$ values measured are listed in Table 1. $EC_{50}$-T Con1b were obtained with the wild type replicon of genotype 1b, $EC_{50}$-T $Cl_1$ and $EC_{50}$-T Cl2 were obtained with the chimeric replicons of clinical isolates 1a_H77 and 1a_6 respectively.

Enzyme Inhibition Assay
a) Cloning, Expression and Purification of NS5B

The coding sequence for NS5B (genotype 1b consensus strain Con1) lacking 21 C-terminal residues was amplified from plasmid pFKI$_{389}$/ns3-3' (Genbank accession no. AJ242654), plasmid pCV-H77C (Genbank accession no. AF 011751.1) and subcloned into the pET21b plasmid as described previously (Pauwels et al. J. Virol., 2007). The NS5BΔC21 expression constructs were transformed into *E. coli* Rosetta 2 (DE3) (Novagen, Madison, Wis.). One hundred milliliters of LB-medium supplemented with carbenicillin (50 μg/mL) and chloramphenicol (34 μg/mL) was inoculated with one colony, grown overnight, and transferred to fresh LB-medium supplemented with 3% ethanol, carbenicillin and chloramphenicol, at a ratio of 1:200. Cells were grown to an optical density at 600 nm of 0.6, after which the expression cultures were shifted to a growth temperature of 20° C. following induction with ispopropyl-1-thio-β-D-galactopyranoside and MgCl$_2$ at a final concentration of 0.4 mM and 10 μM, respectively. After 18 h of induction, cells were harvested by centrifugation and resuspended in 20 mM Tris-HCl, pH 7.5, 300 mM NaCl, 10% glycerol, 0.1% NP40, 4 mM MgCl$_2$, 5 mM DTT supplemented with EDTA-free Complete Protease Inhibitor (Roche, Basel, Switzerland). Cell suspensions were disrupted by sonication and incubated with 10-15 mg/L of DNase I (Roche, Basel, Switzerland) for 30 min. Cell debris was removed through ultracentrifugation at 30,000×g for 1 hour and clarified cell lysate was flash frozen and stored at −80° C. prior to purification.

Clarified cell lysate was thawed and subsequently loaded onto a 5 mL pre-packed HisTrap FF column equilibrated with 25 mM HEPES, pH 7.5, 500 mM NaCl, 10% glycerol and 5 mM DTT. Proteins were eluted with 500 mM imidazole at a flow rate of 1 mL/min. Fractions containing the protein of interest were applied onto a pre-packed 26/10 HiPrep Desalting Column equilibrated with 25 mM HEPES, pH 7.5, 250 mM NaCl, 10% glycerol and 5 mM DTT. The buffer-exchanged NS5B peak was then applied onto a 6 ml Resource S column. Protein was eluted with an increasing salt gradient and fractions collected. Protein purity was assessed on Nu-PAGE pre-cast gels (Invitrogen, Carlsbad, Calif.). Purified NS5B samples were concentrated using Centri-Prep concentrators (Millipore, Billerica, Mass., USA) and protein concentrations were determined by spectrofotometry with the Nanodrop (Nanodrop Technologies, Wilmington, Del., USA).

b) RNA-Dependent RNA Polymerase Assay

Measurement of HCV NS5B polymerization activity was performed by evaluating the amount of radio labeled GTP incorporated by the enzyme in a newly synthesized RNA using heteropolymeric RNA template/primer. The RdRp assay was carried out in 384-well plates. 2.5 nM of purified NS5B enzyme was pre-incubated for 10 min with 150 nM 5'-biotinylated oligo(rG$_{13}$) primer, 15 nM poly(rC) template, in 18 mM Tris-HCl, pH 7.5, 5 mM MgCl$_2$, 20.5 mM KCl, 17 mM NaCl and 2.5 mM of DTT. The test compounds were the added to the preformed polymerase-template complex, and incubated at room temperature for 15 min before the addition 600 nM of GTP, and 0.13 μCi of [$^3$H]GTP. 30 μL reaction mixture was incubated at room temperature for 2 h before stopping the reaction by adding 30 μL of streptavidin coated SPA-beads (GE Healthcare, Uppsala, Sweden) in 0.5 M EDTA. The 30 μL reaction was terminated after 2 hours at 25° C. upon addition of 30 μl streptavidin-coated SPA beads (GE Healthcare, Uppsala, Sweden 5 mg/ml in 0.5 M EDTA). After incubation at 25° C. for 30 min, the plate was counted using a Packard TopCount microplate reader (30 sec/well, 1 min count delay) and IC$_{50}$ values were calculated. IC$_{50}$ values represent the concentration of compound required to decrease by 50% the amount of RNA produced which is measured by the detection of incorporated radiolabeled GTP. The IC$_{50}$ values obtained are listed in Table 1.

The following Table 1 lists compounds according to any one of the above examples for which activity has been determined according to example 3.

TABLE 1

| Cpd. Nr. | EC$_{50}$-T CI1 (μM) | EC$_{50}$-T CI2 (μM) | EC$_{50}$-T Con1b (μM) | IC$_{50}$ at 5 nM (μM) |
|---|---|---|---|---|
| 10 | 0.121 | 0.088 | 0.075 | 0.161 |
| 15 | 0.102 | 0.099 | 0.169 | 0.124 |
| 21 | 0.055 | 0.095 | 0.123 | 0.148 |
| 22 | 0.156 | 0.201 | 0.164 | 0.181 |
| 32 | 1.600 | 2.952 | 3.608 | 1.823 |
| 40 | 5.152 | 5.271 | 7.344 | 1.090 |
| 50 | 0.117 | 0.156 | 0.254 | 0.109 |
| 51 |  |  |  | 0.088 |
| 52 | 7.139 | 7.959 | 7.664 | 1.656 |
| 53 | 0.044 | 0.066 | 0.083 |  |
| 54 | 0.067 | 0.081 | 0.103 |  |

Enzyme Binding Assay

The compounds of formula (I) were examined for their enzymatic binding kinetics or affinity using a Surface Plasmon Resonance (SPR)-based method, i.e. Biacore. A slow dissociation of the inhibiting compound from its viral target (low k$_{off}$, low K$_d$) is believed to potentially reduce the development of drug resistance against anti-viral drugs (Dierynck et al. 2007. Journal of Virology, vol. 81, No. 24, 13845-13851). All measurements were performed on a Biacore T100 instrument (GE Healthcare). The purified HIS$_6$-tagged NS5BΔC21 polymerases were immobilized using non-covalent capturing to an NTA sensor chip (GE Healthcare) in immobilization buffer (20 mM MOPS pH 7.4, 500 mM NaCl, 0.005% Tween-P20, 1 mM DTT, 50 μM EDTA). Interaction studies were all performed at 25° C. Inhibitors were serially diluted in running buffer (20 mM Tris-HCl pH 7.4, 150 mM NaCl, 50 μM EDTA, 1 mM DTT, 0.005% Tween-P20) containing 5% dimethyl sulfoxide (DMSO). Single-cycle kinetics were used, in which 5 increasing concentrations of compound were injected for a period of 300 s each in 1 single cycle, and dissociation was monitored for a period of 1200 s. The sensor surface was completely regenerated in between the cycles. Data were analyzed using simultaneous nonlinear regression analysis (global fitting) adapted for single-cycle kinetics with Biacore T100 BiaEval evaluation software 2.0 (GE Healthcare). The individual rate constants k$_{on}$ and k$_{off}$ and a derived affinity constant, K$_d$=k$_{off}$/k$_{on}$, were determined by a kinetic evaluation of the sensorgrams. The kinetic models accounted for bulk and limited mass transport effects. Every analysis was performed at least in two independent experiments. The dissociation rate of a kinetic interaction can be translated into a compound residence time (dissociative half-life t$_{1/2}$=ln(2)/k$_{off}$) representative for the interaction time between the polymerase and its inhibitor.

The observed association rate constants (k$_{on}$), dissociation rate constants (k$_{off}$), derived affinity constant (K$_d$) and dissociative half-life (t$_{1/2}$) measured for compounds of formula (I) or subgroups thereof on NS5B wild-type enzyme genotypes 1a, 1b and 4a are given in Table 2.

TABLE 2

| Genotype | Cpd. Nr. | $k_{on}$ (1/MS) | $k_{off}$ (1/s) | $K_D$ (M) | $t_{1/2}$ (s) |
|---|---|---|---|---|---|
| 1a | 32 | 3.0E+03 | 8.9E−03 | 3.3E−06 | 78 |
|  | 50 | 1.7E+05 | 6.7E−03 | 4.0E−08 | 103 |
|  | 51 | 9.5E+04 | 3.5E−03 | 3.9E−08 | 198 |
| 4a | 32 | 1.9E+04 | 8.7E−03 | 4.5E−07 | 80 |
|  | 50 | 2.2E+05 | 2.0E−03 | 9.1E−09 | 343 |
|  | 51 | 1.9E+05 | 2.2E−03 | 1.1E−08 | 320 |
| 1b | 32 | 1.3E+04 | 1.5E−02 | 1.2E−06 | 47 |
|  | 50 | 2.3E+04 | 6.0E−04 | 2.5E−08 | 1163 |
|  | 51 | 2.0E+04 | 3.1E−04 | 1.6E−08 | 2243 |

Example 14

Pharmaceutical Compositions of Compounds of Formula (I)

Formulation

Active ingredient, in casu a compound of formula (I), is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa·s, are dissolved in organic solvents such as ethanol, methanol methylene chloride. Suitably the polymer is dissolved in ethanol. The polymer and compound solutions is mixed and subsequently spray dried. The ratio of compound/polymer was selected from 1/1 to 1/6. Intermediate ranges were 1/1.5 and 1/3. A suitable ratio was 1/6. The spray-dried powder, a solid dispersion, is subsequently filled in capsules for administration. The drug load in one capsule ranges between 50 and 100 mg depending on the capsule size used.

Film-Coated Tablets
Preparation of Tablet Core

A mixture of 100 g of active ingredient, in casu a compound of formula (I), 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenated. The tablet cores are coated with the thus obtained mixture in a coating apparatus.

Example 15

Pharmacokinetic Analysis after Single Oral Administration

Three male Sprague-Dawley rats were given a single oral dose of 10 mg/kg of the studied compounds. The compounds were administered by gavage as a solution in PEG400/2% Vitamine E Tocopherol polyethyleneglycol succinate (Vitamin E-TPGS). 7 hours after administration, the animals were sacrificed and plasma and liver samples taken. The samples were analyzed using a qualified research LC-MS/MS method to determine the concentration of the compound in the liver and the liver-to-plasma ratio at 7 h post dosing. The obtained results are summarized in table 3. It was found that Sprague-Dawley rat liver concentrations 7 hours after oral dosing of the studied compounds was high, and that the studied compounds exhibited a very high liver-to-plasma ratio.

TABLE 3

| Cpd. Nr. | Concentration Liver | Lever/plasma ratio |
|---|---|---|
| 10 | 1717 ng/g | 64 |
| 15 | 1524 ng/g | 99 |

The invention claimed is:

1. A compound of formula (I),

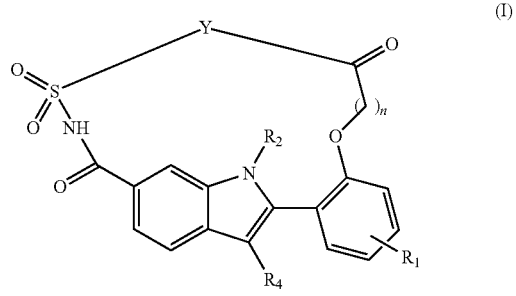

or a stereochemically isomeric form, or a pharmaceutically acceptable salts, thereof, wherein:
$R_1$ is selected from hydrogen, halo and $C_{1-4}$alkoxy;
$R_2$ is selected from $C_{1-4}$alkyl and $C_{3-6}$cycloalkyl;
$R_4$ is $C_{3-7}$cycloalkyl optionally substituted with halo;
n is 1 or 2;
Y is selected from

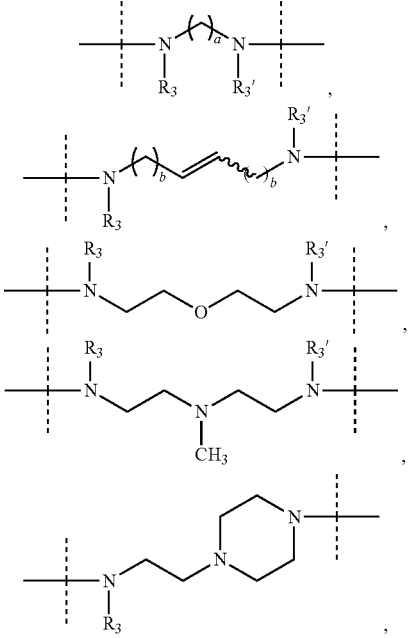

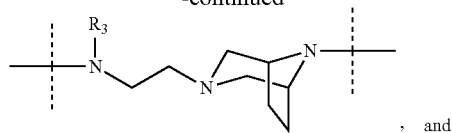

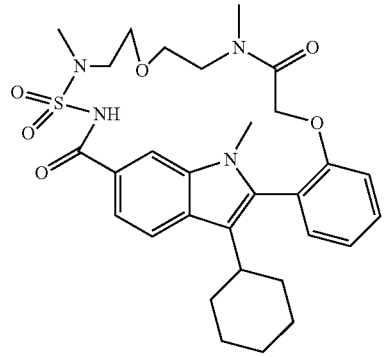

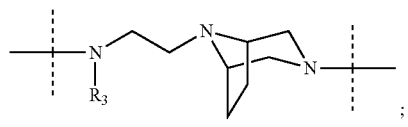

a is 2, 3, 4 or 5;
each b is independently 1 or 2;
R₃ and R₃' are independently selected from hydrogen, C₁₋₆alkyl and C₃₋₆cycloalkyl.

2. A compound according to claim 1 wherein Y is selected from —N(CH₃)—(CH₂)₄—N(CH₃)—,

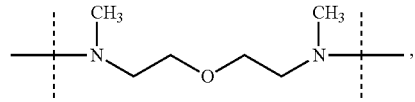

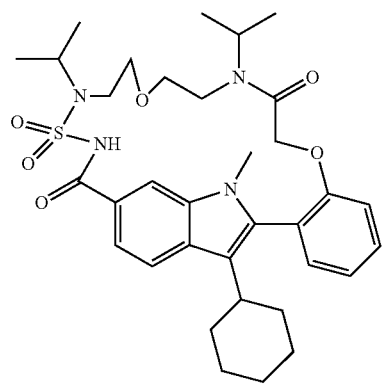

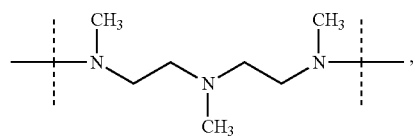

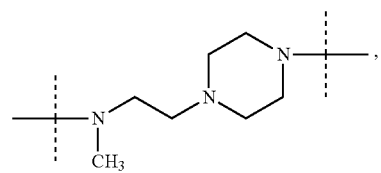

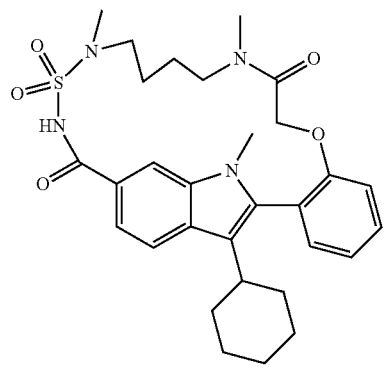

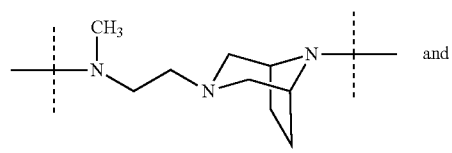

and

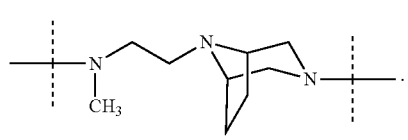

3. A compound according to claim 1 wherein R₁ is hydrogen or methoxy or fluoro.
4. A compound according to claim 1 wherein R₂ is selected from methyl, ethyl, iso-propyl and cyclopropyl.
5. A compound according to claim 1 wherein R₄ is selected from cyclohexyl and 2-fluorocyclohexyl.
6. A compound according to claim 1 wherein n is 1.
7. A compound according to claim 1 selected from

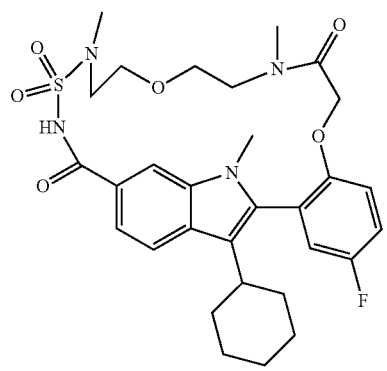

81
-continued
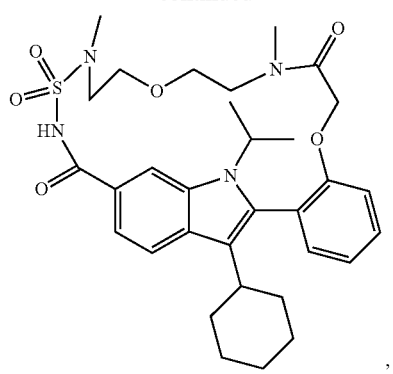 [SMILES: CN1CCN(C)C(=O)COc2ccccc2-c2c(C3CCCCC3)c3ccc(cc3n2C)C(=O)NS(=O)(=O)N(C)CC1]
,
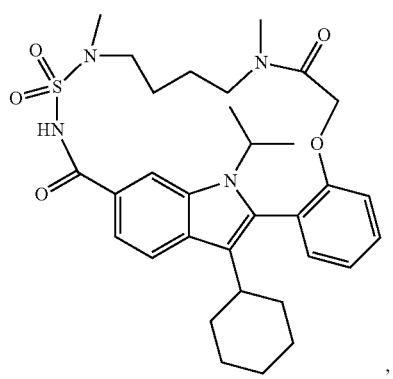
,
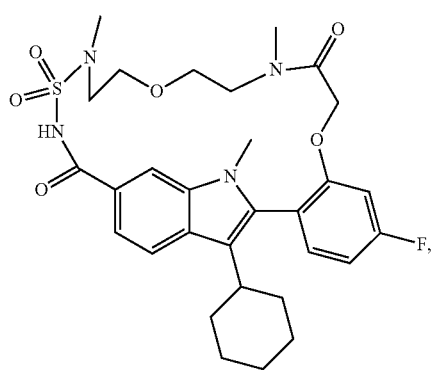
,
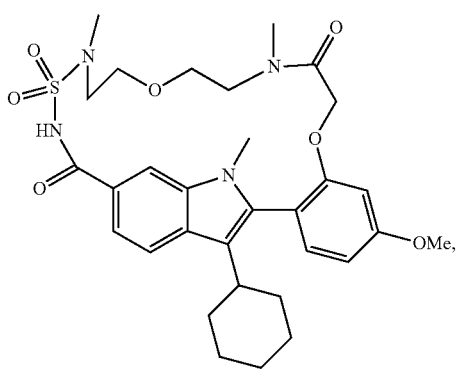
,
82
-continued
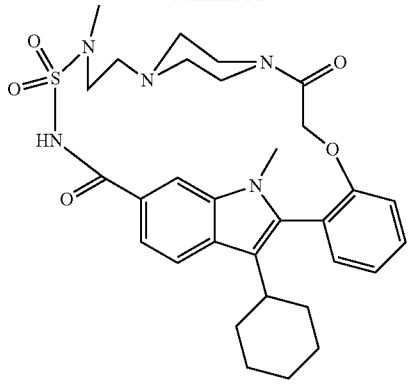
,
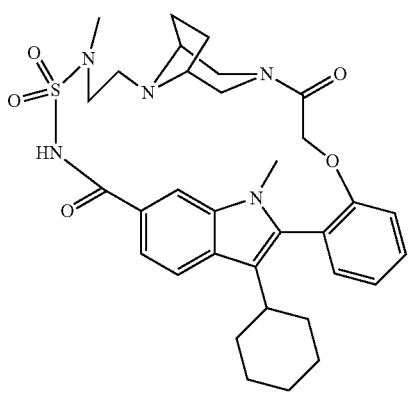
,
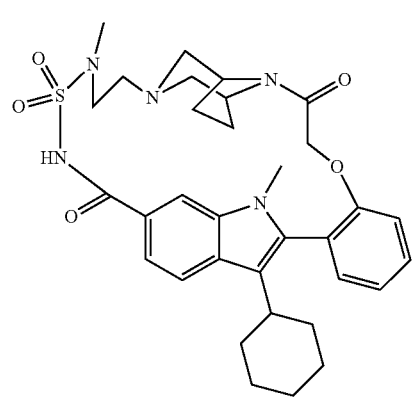
,
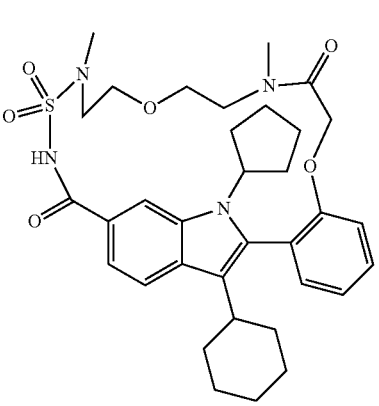
and -continued

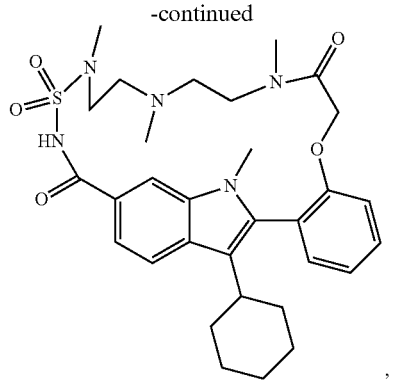

, or a stereochemically isomeric form, or a pharmaceutically acceptable salt, thereof.

8. A pharmaceutical composition comprising a carrier, and as active ingredient an anti-virally effective amount of a compound as claimed in claim 1.

9. A pharmaceutical composition according to claim 8, further comprising at least one other anti-HCV compound.

10. A pharmaceutical composition according to claim 8, further comprising at least one anti HIV compound.

* * * * *